(12) United States Patent
Corgie et al.

(10) Patent No.: US 10,792,649 B2
(45) Date of Patent: Oct. 6, 2020

(54) AUTOMATED BIONANOCATALYST PRODUCTION

(71) Applicant: ZYMtronix, LLC, Ithaca, NY (US)

(72) Inventors: Stephane Corgie, Ithaca, NY (US); Matthew Chun, Ithaca, NY (US); Ricki Chairil, El Monte, CA (US); Rani Talal Brooks, Jefferson, LA (US)

(73) Assignee: Zymtronix, LLC, Ithaca, NY (US)

( * ) Notice: Subject to any disclaimer, the term of this patent is extended or adjusted under 35 U.S.C. 154(b) by 221 days.

(21) Appl. No.: 15/743,999

(22) PCT Filed: Jul. 8, 2016

(86) PCT No.: PCT/US2016/041461
§ 371 (c)(1),
(2) Date: Jan. 11, 2018

(87) PCT Pub. No.: WO2017/011292
PCT Pub. Date: Jan. 19, 2017

(65) Prior Publication Data
US 2018/0200701 A1 Jul. 19, 2018

Related U.S. Application Data

(60) Provisional application No. 62/193,041, filed on Jul. 15, 2015.

(51) Int. Cl.
| | | |
|---|---|---|
| *B01J 31/02* | (2006.01) |
| *B82Y 25/00* | (2011.01) |
| *B01J 35/00* | (2006.01) |
| *C12N 11/14* | (2006.01) |
| *B01J 31/00* | (2006.01) |
| *C12N 11/04* | (2006.01) |
| *B82Y 5/00* | (2011.01) |
| *B82Y 15/00* | (2011.01) |
| *B82Y 40/00* | (2011.01) |
| *B01J 37/02* | (2006.01) |

(52) U.S. Cl.
CPC .......... *B01J 31/02* (2013.01); *B01J 31/003* (2013.01); *B01J 35/0033* (2013.01); *B82Y 25/00* (2013.01); *C12N 11/04* (2013.01); *C12N 11/14* (2013.01); *B01J 37/0215* (2013.01); *B82Y 5/00* (2013.01); *B82Y 15/00* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 4,152,210 A | 5/1979 | Robinson et al. | |
| 5,460,830 A * | 10/1995 | Kossovsky | A61K 9/0019 |
| | | | 424/490 |
| 5,965,418 A | 10/1999 | Fuglsang et al. | |
| 6,440,711 B1 | 8/2002 | Dave et al. | |
| 6,447,811 B1 | 9/2002 | Ravensberg et al. | |
| 7,241,883 B2 | 7/2007 | Lugade et al. | |
| 7,385,053 B2 | 6/2008 | Lugade et al. | |
| 7,459,145 B2 | 12/2008 | Bao et al. | |
| 7,485,367 B2 | 2/2009 | Chen et al. | |
| 7,731,954 B2 | 6/2010 | Davis et al. | |
| 8,075,793 B2 | 12/2011 | Moreira et al. | |
| 8,188,269 B1 | 5/2012 | Lugade et al. | |
| 8,841,105 B2 | 9/2014 | Sakai et al. | |
| 8,940,179 B2 | 1/2015 | Suh et al. | |
| 9,035,003 B2 | 5/2015 | Hanson et al. | |
| 9,597,672 B2 | 3/2017 | Corgie et al. | |
| 9,765,324 B2 * | 9/2017 | Corgie | C12N 11/08 |
| 10,260,061 B2 | 4/2019 | Corgie | |
| 10,316,313 B2 | 6/2019 | Corgie | |
| 10,351,841 B2 | 7/2019 | Corgie | |
| 2003/0138490 A1 | 7/2003 | Hu et al. | |
| 2003/0146529 A1 | 8/2003 | Chen et al. | |
| 2003/0203056 A1 | 10/2003 | Tumbers | |
| 2004/0039201 A1 | 2/2004 | Lugade et al. | |
| 2004/0043135 A1 | 3/2004 | Han et al. | |
| 2004/0166547 A1 | 8/2004 | Sullivan et al. | |
| 2006/0165910 A1 | 7/2006 | Kodas et al. | |
| 2006/0286379 A1 | 12/2006 | Gao et al. | |
| 2006/0289354 A1 | 12/2006 | Zhou et al. | |
| 2007/0135312 A1 | 6/2007 | Melbouci | |
| 2007/0154565 A1 | 7/2007 | Zaghmout | |

(Continued)

FOREIGN PATENT DOCUMENTS

| | | |
|---|---|---|
| CN | 1580233 A | 2/2005 |
| CN | 101109016 A | 1/2008 |

(Continued)

OTHER PUBLICATIONS

Pecova, M. et al Nanotechnol. 2013 vol. 2013 125102 pp. 1-11.*

(Continued)

*Primary Examiner* — Heidi Reese
(74) *Attorney, Agent, or Firm* — Kaplan IP Law, P.C.; Jonathan M. Kaplan

(57) ABSTRACT

The present invention provides machines, compositions and methods for producing bionanocatalysts (BNCs) comprising one or more enzymes selected from a broad spectrum of industrially and medically important enzymes. The BNCs are self-assembled and magnetically immobilized enzymes. The machines, compositions, and methods are fully scalable from bench top to industrial manufacturing volumes.

37 Claims, 6 Drawing Sheets

(56) References Cited

U.S. PATENT DOCUMENTS

| | | |
|---|---|---|
| 2008/0103061 A1 | 5/2008 | Lugade et al. |
| 2008/0287288 A1 | 11/2008 | Ying et al. |
| 2008/0305048 A1 | 12/2008 | Josephson et al. |
| 2009/0053512 A1 | 2/2009 | Pyun et al. |
| 2009/0142281 A1 | 6/2009 | Rand et al. |
| 2009/0214885 A1 | 8/2009 | Her et al. |
| 2009/0238811 A1 | 9/2009 | McDaniel et al. |
| 2009/0285890 A1 | 11/2009 | Plas et al. |
| 2010/0056360 A1 | 3/2010 | Lee |
| 2010/0056816 A1 | 3/2010 | Wallin et al. |
| 2010/0152326 A1 | 6/2010 | Kurz |
| 2010/0226856 A1 | 9/2010 | Vitaliano et al. |
| 2010/0285376 A1 | 11/2010 | Hsueh et al. |
| 2011/0203756 A1 | 8/2011 | Nordin et al. |
| 2011/0300201 A1 | 12/2011 | Becker et al. |
| 2011/0312497 A1 | 12/2011 | Barg et al. |
| 2012/0039799 A1 | 2/2012 | Franzen et al. |
| 2012/0058074 A1 | 3/2012 | Braig et al. |
| 2012/0108491 A1 | 5/2012 | Simonsen |
| 2012/0123026 A1 | 5/2012 | Lugade et al. |
| 2012/0214218 A1 | 8/2012 | Xing et al. |
| 2012/0270031 A1 | 10/2012 | Guan et al. |
| 2013/0196407 A1 | 8/2013 | Sheldon et al. |
| 2014/0004583 A1 | 1/2014 | Corgie et al. |
| 2014/0046023 A1 | 2/2014 | Gottschall et al. |
| 2014/0296507 A1 | 10/2014 | Sannino et al. |
| 2014/0377789 A1 | 12/2014 | Moerman |
| 2015/0056145 A1 | 2/2015 | Chae et al. |
| 2015/0252352 A1 | 9/2015 | Corgie et al. |
| 2017/0096658 A1 | 4/2017 | Corgie et al. |
| 2017/0175101 A1 | 6/2017 | Corgie et al. |
| 2017/0189960 A1 | 7/2017 | Ibe |
| 2018/0087043 A1 | 3/2018 | Corgie |
| 2018/0146663 A1 | 5/2018 | Corgie et al. |
| 2018/0200701 A1 | 7/2018 | Corgie et al. |
| 2019/0174745 A1 | 6/2019 | Corgie |
| 2019/0174746 A1 | 6/2019 | Corgie |
| 2019/0309282 A1 | 10/2019 | Corgie |

FOREIGN PATENT DOCUMENTS

| | | |
|---|---|---|
| CN | 101198255 A | 6/2008 |
| CN | 102329008 A | 1/2012 |
| CN | 102329008 B | 1/2013 |
| CN | 103675115 A | 3/2014 |
| CN | 104624166 A | 5/2015 |
| CN | 104624166 B | 6/2017 |
| EP | 1028628 A1 | 8/2000 |
| EP | 1028628 B1 | 2/2003 |
| EP | 2110175 A1 | 10/2009 |
| EP | 2593544 A2 | 5/2013 |
| EP | 1476753 B1 | 8/2013 |
| GB | 2211504 A | 7/1989 |
| JP | 2005532533 A | 10/2005 |
| JP | 4598403B2 B2 | 12/2010 |
| KR | 2011/033575 A | 3/2011 |
| SU | 1000098 | 2/1983 |
| WO | 8802600 A1 | 4/1988 |
| WO | 9111105 A1 | 8/1991 |
| WO | 95/012392 A1 | 5/1995 |
| WO | 199715664 A1 | 5/1997 |
| WO | 9922597 A1 | 5/1999 |
| WO | WO9922597 A1 | 5/1999 |
| WO | 0158267 A1 | 8/2001 |
| WO | WO-03/084982 A2 | 10/2003 |
| WO | WO03080796 A2 | 10/2003 |
| WO | WO2006004557 A1 | 1/2006 |
| WO | 2008156948 A2 | 12/2008 |
| WO | WO2009115335 A1 | 9/2009 |
| WO | 2011161261 A1 | 12/2011 |
| WO | 2012010295 A1 | 1/2012 |
| WO | WO-2012/023847 A2 | 2/2012 |
| WO | 2012122437 A2 | 9/2012 |
| WO | WO2012122437 A2 | 9/2012 |
| WO | WO2012122437 A3 | 9/2012 |
| WO | 2013046165 A1 | 4/2013 |
| WO | WO2013109057 A1 | 7/2013 |
| WO | 2013170050 A1 | 11/2013 |
| WO | 2014055853 A1 | 4/2014 |
| WO | WO2015078241 A1 | 6/2015 |
| WO | 2015100432 A2 | 7/2015 |
| WO | WO2015111030 A2 | 7/2015 |
| WO | WO2015113047 A2 | 7/2015 |
| WO | WO2015145222 A2 | 10/2015 |
| WO | WO2015157530 A2 | 10/2015 |
| WO | 2016138477 A1 | 9/2016 |
| WO | 2016186879 A1 | 11/2016 |
| WO | 2017011292 A1 | 1/2017 |
| WO | 2017180383 A1 | 10/2017 |
| WO | 2018034877 A1 | 2/2018 |
| WO | 2018102319 A1 | 6/2018 |
| WO | 2020051159 A1 | 3/2020 |
| WO | 2020069227 A1 | 4/2020 |

OTHER PUBLICATIONS

Hydrolase Nomenclature excerpt from Enzyme Nomenclature Recommendations Nomenclature Committee of the International Union of Biochemistry and Molecular Biology download from https://www.qmul.ac.uk/sbcs/iubmb/enzyme/EC3/ on Nov. 22, 2019.*

Demirel, D. et al. Preparation and characterization of magnetic duolite-polystyrene composite particles for enzyme immobilization, Journal of Food Engineering, 62(2004)203-208.

European Search Report for European application No. 17782855.5 dated Nov. 11, 2019.

PCT Search Report and Written Opinion dated Dec. 23, 2019 for PCT/US19/49397.

PCT Search Report and Written Opinion dated Dec. 11, 2019 for PCT/US19/53307.

Zheng, M. et al. "Magnetic field intensified bi-enzyme system with in situ cofactor regeneration . . . " Journal of Biotechnology vol. 168 No. 2 (Oct. 2013).

Ahmad et al., Physico-Chemical Processes. Water Environment Research, vol. 77, No. 6, Literature Reviews [CD-ROM content}, pp. 982-1156 (2005).

Adams et al. Specificity of Glucose Oxidase. Archives of Biochemistry and Biophysics 91 (1960) 230-234.

Ansari et al. Potential applications of enzymes immobilized on/in nano materials: A review. Biotechnology Advances 30 (2012) 512-523.

Anthon et al. Colorimetric Method for the Determination of Lipoxygenase Activity. J. Agric. Food Chem. 49 (2001) 32-37.

Banerjee et al. A High-Throughput Colorimetric Assay for Enantioselective Screening of Nitrilase-Producing Microorganisms Using pH Sensitive Indicators. Journal of Biomolecular Screening 8(5); 2003, pp. 559-565.

Baskar et al., Magnetic immobilization and characterization of beta-amylase as nanobiocatalyst for hydrolysis of sweet potato starch. Biochemical Engineering Journal 102 (2015) 18-23.

Cassimjee. ѡ-Transaminase in Biocatalysis Methods. ractions and Engineering. Doctoral Thesis KTH Royal Institute of Technology, School of Biotechnology Stockholm (2012).

Dong et al. Efficient biosynthesis of uridine diphosphate glucose from maltodextrin by multiple enzymes immoblized on magnetic nanoparticles. Carbohydrate Research 345, (2010) 1622-1626.

Errede et al. Oxidation of ferrocytochrome c by mitochondrial cytochrome c oxidase. Proc. Nat. Acad. Sci. USA, vol. 73, No. 1, pp. 113-117, Jan. 1976.

Gebreyohannes et al. Nanoscale tuning of enzyme localization for enhanced reactor performance in a novel magnetic-responsive biocatalytic membrane reactor. Journal of Membrane Science 487 (2015) 209-220.

Illanes et al. Recent trends in biocatalysis engineering. Bioresource Technology 115 (2012) 48-57.

Karn et al. Nanotechnology and in Situ Remediation: A Review of the Benefits and Potential Risks. Environmental Health Perspectives, vol. 117, No. 12 (Dec. 2009), pp. 1823-1831.

(56) References Cited

OTHER PUBLICATIONS

Khan et al. Hazardous Waste Treatment Technologies. Water Environment Research, vol. 79, No. 10, Literature Reviews [CD-ROM content] (2007), pp. 1858-1902.
Kim et al. Hazardous Waste Treatment Technologies. Water Environment Research, vol. 64, No. 4, 1992: Literature Review (Jun. 1992), pp. 469-479.
Kim et al. Single enzyme nanoparticles in nanoporous silica: A hierarchical approach to enzyme stabilization and immobilization. Enzyme and Microbial Technology 39 (2006) 272-480.
Kim et al. Nanobiocatalysis and its potential applications. Trends in Biotechnology vol. 26, No. 11 (2008) 639-646.
Neto. Process Considerations for the Asymmetric Synthesis of Chiral Amines using w-Transaminase. Thesis, center for Process Engineering and Technology Department of Chemical and Biochemical Engineering Technical University of Denmark, Aug. 2013, pp. 1-108 and 109-117.
Rai et al. Optimization for production of liquid nitrogen fertilizer from the degradation of chicken feather by iron-oxide (Fe3O4) magnetic nanoparticles couples β-keratinase. Biocatalysis and Agricultural Biotechnology, vol. 4, Issue 4, Oct. 2015, pp. 1-13.
Sanders et al., Self-Assembly Using Dynamic Combinatorial Chemistry. Philosophical Transactions: Mathematical, Physical and Engineering Sciences, vol. 362, No. 1819, Organizing Atoms: Manipulation of Matter on the Sub-10 nm Scale (Jun. 15, 2004) pp. 1239-1245.
Sheldon et al. Enzyme immobilisation in biocatalysis: why, what and how. Chem. Soc. Rev. 2013, vol. 42, 6223-6225.
Tappel et al. E. Lipoxidase. H. F. Linskens et al. (eds.) Modern Methods of Plant Analysis/Moderne Methoden der Pflanzenanalyse Springer-Verlag OHG. Berlin-Goettingen-Heidelberg 1964—pp. 469-471.
Tundo et al. methods and Reagents for Green Chemistry: An Introduction. 2007. A John Wiley & Sons Inc. Publication, pp. 1-312 (333 pages total).
Villaverde et al. Hydroperoxide production from linoleic acid by heterologous Gaeumannomyces graminis tritici poxygenase: Optimization and scale-up. Chemical Engineering Journal 214 (2013) 82-90.
Villaverde et al. Analysis of linoleic acid hydroperoxides generated by biomimetic and enzymatic systems through an integrated methodology. Industrial Crops and Products 34 (2011) 1474-1481.
Wang et al. Enhanced phenol degradation in coking wastewater by immobilized laccase on magnetic mesoporous silica nanoparticles in a magnetically stabilized fluidized bed. Bioresource Technology 110 (2012) 120-124.
Wilson et al. Glucose oxidase: an ideal enzyme. Biosensors and Bioelectronics 7 (1992) 165-185.
Zheng et al. Effect of molecular mobility on coupled enzymatic reactions involving cofactor regeneration using nanoparticle-attached enzymes Journal of Biotechnology 154 (2011) 274-280.
The Journal Record News Briefs: Feb. 15, 2010, the Journal Record (Oklahoma City, OK) Feb. 15, 2010 Monday, pp. 1-5.
Three better ways to upcycle waste oil; NUS researchers offer cheaper, greener methods to produce biodiesel the Straits Times (Singapore), Apr. 18, 2015 Saturday, pp. 1-2.
English abstract only of International Application No. WO 03/084982.
Chinese Office Action dated Apr. 28, 2015 received from Application No. 201280022702.9, together with an English-language translation.
Azevedo A.M. et al., "Horseradish Peroxidase: A Valuable Tool in Biotechnology", Biotechnology Annual Review 9:199-247 (2003).
Chalkias N.G. et al., "Activity Increase of Horseradish Peroxidase in the Presence of Magnetic Particles", J. Am. Chem. Soc. 130:2910-2911 (2008).
Corgie S.C. et al., Self-Assembled Complexes of Horseradish Peroxidase with Magnetic Nanoparticles Showing Enhanced Peroxidase Activity, Advanced Functional Materials 22:1940-1951 (Feb. 15, 2012).

Corvini P.F.X. et al., "LANCE: Laccase-Nanoparticle Conjugates for the Elimination of Micropollutants (Endocrine Disrupting Chemicals) from Wastewater in Bioreactors", Rev Environ Sci Biotechnol 9:23-27 (2010).
Huang J. et al., "Zinc Tetraaminophthalocyanine-Fe3O4 Nanoparticle Composite for Laccase Immobilization", International Journal of Nanomedicine 2(4): 775-784 (2007).
Luo X-L et al., "Electrochemically Deposited Chitosan Hydrogel for Horseradish Peroxidase Immobilization Through Gold Nanoparticles Self-Assembly", Biosensors and Bioelectronics 21:190-196 (2005).
Tang D. et al., "Direct Electrochemical Immunoassay Based on Immobilization of Protein-Magnetic Nanoparticle Composites on to Magnetic Electrode Surfaces by Sterically Enhanced Magnetic Field Force", Biotechnology Letters 28:559-565 (2006).
Wang F. et al., "Magnetic Mesoporous Silica Nanoparticles: Fabrication and Their Laccase Immobilization Perforamnce", Bioresource Technology 101:8931-8935 (2010).
Yang H-H et al., "Magnetite-Containing Spherical Silica Nanoparticles for Biocatalysis and Bioseparations", Analytical Chemistry 76(5): 1316-1321 (Mar. 1, 2004).
International Search Report dated Oct. 10, 2012 received from the Korean Intellectual Property Office from related Application No. PCT/US2012/028392.
International Search Report dated Feb. 20, 2014 received from the Russian Patent Office from related Application No. PCT/US2013/063441.
Morrison et al. Peroxidase-catalyzed halogenation. Annual Review of Biochemistry, vol. 45, 861-888, 1976.
Aguila, Sergio et al. "Stereoselective oxidation of R-(+)-limonene by chloroperoxidase from Caldariomyces fumago," Green Chemistry 10(52):647-653 (2008).
Altschul, Stephen F. et al. "Basic Local Alignment Search Tool," J. Mol. Biol. 215:403-410 (1990).
Banerjee, Anirban et al. "A rapid and sensitive fluorometric assay method for the determination of nitrilase activity," Biotechnol. Appl. Biochem. 37(3):289-293 (2003).
Betancor, Lorena et al. "Preparation of a Stable Biocatalyst of Bovine Liver Catalase Using Immobilization and Postimmobilization Techniques," Biotechnology Progress 19(3):763-767 (2003).
Chau, Yat-Pang et al. "Differential permeability of blood microvasculatures in various sympathetic ganglia of rodents," Anatomy and Embryology, 194(3):259-269 (1996).
Corgie, Stephane et al. "Universal enzyme immobilisation within hierarchically-assembled magnetic scaffolds," Chem. Today 34(5):15-20 (2016).
Dadashipour, Mohammad et al. "Hydroxynitrile Lyases: Insights into Biochemistry, Discovery, and Engineering," ACS Catal. 1:1121-49 (2011).
Denisov, Llia et al. "Structure and Chemistry of Cytochrome P450," Chem. Rev. 105(6):2253-77 (2005).
Dresser, George K. et al. "Pharmacokinetic-Pharmacodynamic Consequences and Clinical Relevance of Cytochrome P450 3A4 Inhibition," Clinical Pharmacokinetics 38(1):41-57 (2012).
Duan, Xiaonan et al. "Hierarchical Hybrid Peroxidase Catalysts for Remediation of Phenol Wastewater," ChemPhysChem, 15(5):974-980 (2014).
Fiers, W. et al., "Complete nucleotide sequence of SV40 DNA," Nature 273: 113-120 (1978).
Glieder, Anton et al. "Comprehensive Step-by-Step Engineering of an (R)-Hydroxynitrile Lyase for Large-Scale Asymmetric Synthesist**," Angew. Chem. Int. Ed. 42:4815 (2003).
Greenaway, P.J. et al. "Human cytomegalovirus DNA: BumHI, EcoRI and Pst I restriction endonuclease cleavage maps," Gene 18: 355-360 (1982).
Gupta, Namita et al. "Simplified para-nitrophenyl palmitate assay for lipases and esterases," Analytical Biochemistry 311:98-99 (2002).
Hess, B. et al. "Cooperation of Glycolytic Enzymes," J. Adv. Enzyme Res. 7:149 (1968).
Hitzeman, Ronald A. et al. "Isolation and Characterization of the Yeast 3-Phosphoglycerokinase Gene (PGK) by an Immunological Screening Technique," J. Biol. Chem. 255:2073 (1980).

(56) References Cited

OTHER PUBLICATIONS

Holland, Michael J. et al., "Isolation and Identification of Yeast Messenger Ribonucleic Acids Coding for Enolase, Glyceraldehyde-3-phosphate Dehydrogenase, and Phosphoglycerate Kinase," Biochemistry 17:4900 (1978).
Iribarne, Christelle et al. "Involvement of Cytochrome P450 3A4 Enzyme in the N-Demethylation of Methadone in Human Liver Microsomes," Chem. Res. Tox. 9(2): p. 365-373 (1996).
Jones, G.M. et al. "Environmental Streptococcal and Coliform Mastitis," Virgina Cooperative Extension, Publ. 404-234, 2009.
Jones, G.M. "Understanding the Basics of Mastitis," Virgina Cooperative Extension, Publ. 404-233, 2009.
Joo, Hyun et al. "Laboratory evolution of peroxide-mediated cytochrome P450 hydroxylation," Nature, 399(6737):670-673 (1999).
Kim, H. et al. "Cytochrome P450 isozymes responsible for the metabolism of toluene and styrene in human liver microsomes," Xenobiotica 27(7):657-665 (1997).
Kusumoto, I. "Industrial Production of L-Glutamine," American Society for Nutritional Sciences, 131:2552S-2555S (2001).
Lindskog et al. The catalytic mechanism of mammalian carbonic anhydrases New Horizons 7:175-95 (2000).
Lucas, John A. et al. "The Evolution of Fungicide Resistance," Advances in Applied Microbiology, vol. 90, 2015.
Mathew, Sam et al. "ω-Transaminases for the Production of Optically Pure Amines and Unnatural Amino Acids," ACS Catalysis 2(6):993-1001 (2012).
Moses, Marion. "Pesticide-Related Health Problems and Farmworkers," AAOHN J., 37(3):115-30 (1989).
Needleman, Saul B. et al. "A General Method Applicable to the Search for Similarities in the Amino Acid Sequence of Two Proteins," J. Mol. Biol. 48:443 (1970).
Pearson, William R. et al. "Improved tools for biological sequence comparison," Proc. Natl. Acad. Sci. vol. 85, pp. 2444-2448, Apr. 1988.
Ritter, L. et al. "Addressing the Linkage between Exposure to Pesticides and Human Health Effects—Research Trends and Priorities for Research," J. Tox. Environ. Health 9(6):441-56 (2006).
Sawayama, Andrew M. et al. "A Panel of Cytochrome P450 BM3 Variants to Produce Drug Metabolites and Diversify Lead Compounds," Chemistry 15(43):11723-9 (2009).
Schätzle, Sebastian et al. "Rapid and Sensitive Kinetic Assay for Characterization of ω-Transaminases," Analytical chemistry 81(19):8244-8248 (2009).
Shaw, Nicholas M. et al. "Lonza: 20 Years of Biotransformations," Adv. Synth. and Catalysis 345(4): 425-435 (2003).
Shingles, Richard et al. "Direct Measurement of ATP-Dependent Proton Concentration Changes and Characterization of a K+-Stimulated ATPase in Pea Chloroplast Inner Envelope Vesicles," Plant Physiol. 106(2):731-737 (1994).
Shingles, Richard et al. "Measurement of Carbonic Anhydrase Activity Using a Sensitive Fluorometric Assay," Analytical Biochemistry 252(1):190-197 (1997).
Sorouraddin, M.H. et al. "Spectrophotometric determination of some catecholamine drugs using sodium bismutha," Journal of Pharmaceutical and Biomedical Analysis 18:877-881 (1998).
Tsotsou, Georgia E. et al. "High throughput assay for cytochrome P450 BM3 for screening libraries of substrates and combinatorial mutants," Biosensors & Bioelectronics, 17:119-131 (2002).
Wan, Feng-Yi et al. "The influence of oxidation of membrane thiol groups on lysosomal proton permeability," Biochemistry Journal, 360, 355-362 (2001).
Welk, A. et al. "Microbicidal efficacy of thiocyanate hydrogen peroxide after adding lactoperoxidase under saliva loading in the quantitative suspension test," Archives of Oral Biology, 56:1576-1582 (2011).
Wells, Andrew. "What Is in a Biocatalyst?," Organic Process Res. Dev. 10:678-681 (2006).
Wrighton, Steven A. et al. "The Human Hepatic Cytochromes P450 Involved in Drug Metabolism," Cult. Rev. Tox. 22(1):1-21 (1992).
Yamazaki, Hiroshi et al., "Roles of Cytochromes P450 1A2 and 3A4 in the Oxidation of Estradiol and Estrone in Human Liver Microsomes," Chem. Res. Tox. 11(6): p. 659-665 (1998).
U.S. Appl. No. 62/163,032, filed May 18, 2015.
U.S. Appl. No. 62/193,041, filed Jul. 15, 2015.
U.S. Appl. No. 62/323,663, filed Apr. 16, 2016.
Bhosale, S. et al., "Molecular and Industrial Aspects of Glucose Isomerase," Microbiol. Rev. 60(2):280-300 (1996).
Bosch, E.H. et al., "The lactoperoxidase system: the influence of iodide and the chemical and antimicrobial stability over the period of about 18 months," J. Applied Microbiol., 89(2), 215-24 (2000).
Alexander et al. "Cytochrome P450 (E.C. 1.14.-.-)bph_506_108a 215," Br. J. Pharmacol. 158(Suppl 1): S215-S217 (2009).
Bradford, Marion M. "A Rapid and Sensitive Method for the Quantitation of Microgram Quantities of Protein Utilizing the Principle of Protein-Dye Binding," Analytical Biochemistry, 72(1-2):248-254 (1976).
Corgie et al. "Self-Assemblies of Magnetic Nanoparticles (MNPs) and Peroxidase Enzymes: Mesoporous Structures and Nanoscale Magnetic Field Effects (nano-MFEs) for Enhanced Activity BioNanoCatalysts (BNCs)"; Cleantech, www.ct-si.org; Dec. 2012.
Hielscher, Thomas. "Ultrasonic production of nano-size dispersions and emulsions," ENS 05, Paris, France, XP-002788816, Dec. 2005.
Lee et al. "Microfluidic continuous magnetophoretic protein separation using nanoparticle aggregates," Microfluidics and Nanofluidics, Springer, Berlin, DE, vol. 11, No. 4, May 2011.
Merriam-Webster, "Matrix", <https://www.merriam-webster.com/dictionary/matrix>, Copyright 2020 Merriam-Webster, Incorporated.
Boone, Christopher D. et al. "Carbonic Anhydrase: An Efficient Enzyme with Possible Global Implications," International Journal of Chemical Engineering, vol. 2013, Article ID 813931, 2013.
Caswell, Jill M. et al. "From P450 Discovery to Scale-Up for Delivery of Chiral Intermediates," Department of Biocatalysisand Isotope Chemistry, Almac Sciences, UK, downloaded from https://www.almacgroup.com in 2015.
Duong, The-Phong et al. "Characterization of Mechanical Properties of Magnetite-polymer Composite Films," Proceedings of the XIth International Congress and Exposition, Jun. 2-5, 2008 Orlando, Florida USA.
Hoffmann, Sandra et al. "Annual Cost of Illness and Quality-Adjusted Life Year Losses in the United States Due to 14 Foodborne Pathogens," Journal of Food Protection, vol. 75, No. 7, pp. 1292-1302, 2012.
Kim, J. et al. A magnetically separable, highly stable enzyme system based on nanocomposites of enzymes and magnetic nanopartides shipped in hierarchically ordered, mesocellular, mesoporous silica. Small. 2005. vol. 1. No. 12. pp. 1203-1207.
Kirkman, Henry N. et al. "Catalase: A tetrameric enzyme with four tightly bound molecules of NADPH," Proc. Natl. Acad. Sci. USA, vol. 81, pp. 4343-4347, Jul. 1984.
McCall, Keith A. et al. "Function and Mechanism of Zinc Metalloenzymes," American Society for Nutritional Sciences, 1437S-1446S, 2000.
Mix, Stefan. "Shortening the Path—Pharmaceutical Materials from Enzymatic Reactions," Almac Group, Organic Process Research & Development Prague, Oct. 17-19, 2016.
PCT International Preliminary Report on Patentability dated Jul. 31, 2017 for PCT/US2016/041461 filed on Jul. 8, 2016, 10 pages.
PCT International Preliminary Report on Patentability dated Nov. 21, 2017 for PCT/US2016/031419 filed on May 9, 2016, 8 pages.
PCT Search Report and Written Opinion dated Jul. 27, 2016 for PCT/US2016/031419 filed on May 9, 2016, 16 pages.
PCT Search Report and Written Opinion dated Jul. 3, 2017 for PCT/US2017/026086 filed on Apr. 5, 2017, 22 pages.
PCT Search Report and Written Opinion dated Oct. 25, 2017 for PCT/US2017/045655 filed on Aug. 6, 2017, 12 pages.
PCT Search Report and Written Opinion dated Sep. 16, 2016 for PCT/US2016/041461 filed on Jul. 8, 2016, 11 pages.
Porter, Michael M. et al. "Biomimetic Materials by Freeze Casting," JOM: the journal of the Minerals, Metals, and Materials Society, 65(6), Apr. 2013.

(56) References Cited

OTHER PUBLICATIONS

Sawayama, Andrew M. et al. "A Panel of Cytochrome P450 BM3 Variants to Produce Drug Metabolites and Diversify Lead Compounds," Chem. Eur. J. 2009.
Wainaina, James et al. "Synthesis of Magnetite/Amphiphilic Polymer Composite Nanoparticles as Potential Theragnostic Agents," Journal of Nanoscience and Nanotechnology, vol. 12, 5920-5924, 2012.
Yamagata, Mika et al. "Magnetite/Polymer Composite Particles Prepared by Molecular Assembling Followed by in-Situ Magnetite Formation," Macromol. Symp., 245-246, 363-370, 2006.
PCT Search Report and Written Opinion dated Feb. 12, 2018 for PCT/US2017/063542 filed on Nov. 28, 2017, 9 pages.
El-Zahab et al. "Enabling multienzyme biocatalysis using nanoporous materials," Biotechnol Bioeng, vol. 87, No. 2, pp. 178-183, Jul. 20, 2004.
Liu et al. "Nanopartide-supported multi-enzyme biocatalysis with in situ cofactor regeneration," J Biotechnol, vol. 139, No. 1, pp. 102-107, Oct. 19, 2008.
Petkova et al. "Synthesis of silica particles and their application as supports for alcohol dehydrogenases and cofactor immobilizations: conformational changes that lead to switch in enzyme stereoselectivity," Biochim Biophys Acta, vol. 1824, No. 6, pp. 792-801, Mar. 26, 2012.
Zheng et al. "Magnetic field intensified bi-enzyme system with in situ cofactor regeneration supported by magnetic nanoparticles," J Biotechnol, vol. 168, No. 2, pp. 212-217, Jun. 10, 2013.
Carozza, Susan E. et al. "Risk of Childhood Cancers Associated with Residence in Agriculturally Intense Areas in the United States," Environ. Health Perspect. 116(4):559-65 (2008).
Corning, Website at https://www.corning.com/worldwide/en/products/life-sciences/products/adme-tox-research/recombinant-metabolic-enzymes.html. Downloaded Mar. 4, 2018.
Cypex, Website located at http://www.cypex.co.uk/ ezcypbuf.htm. Dowloaded on Mar. 4, 2018.
Cytochrome c Oxidase Assay Kit, Sigma-Aldrich 2014:1-4; website located at https://www.ncbi.nlm.nih.gov/pmc/articles/PMC2884625/. Downloaded on Mar. 4, 2018.
Gong, Jin-Song et al., "Nitrilases in nitrile biocatalysis: recent progress and forthcoming research," Microbial Cell Factories 11(1):142 (2012).
Kerr, Susan. "Drying-Off Lactating Livestock," Small Farms vol. V, No. 3 (2010).
Kirkman, Henry N. et al. "Catalase: A tetrameric enzyme with four tightly bound molecules of NADPH," Proc. Natl. Acad. Sci. USA. 81(14):4343-7 (1984).
Li, Yi et al. "Rapid Kinetic Microassay for Catalase Activity," J. Biomolecular Techniques 18(4):185-187 (2007).
Mark, Genevieve L. et al. "Molecular-based strategies to exploitPseudomonas biocontrol strains forenvironmental biotechnologyapplications," FEMS Microbiol. Ecol. 56(2):167-77 (2006).
Newsholme, Philip et al. "Glutamine and glutamate—their central role in cell metabolism and function," Cell Biochem. and Function, 21:1-9 (2003).
Nielsen, Christel. "Economic Impact of Mastitis in Dairy Cows," Department of Animal Breeding and Genetics, Uppsala, Sweden, Swedish University of Agricultural Sciences (2009).
Purdy, Michael A. et al. "Effect of Growth Phase and Cell Envelope Structure on Susceptibility of *Salmonella typhimurium* to the Lactoperoxidase-Thiocyanate-Hydrogen Peroxide System," Infection and Immunity, 39(3), 1187-1195 (1983).
Reeves, Margaret et al. "Greater Risks, Fewer Rights: U.S. Farmworkers and Pesticides," Int'l J., Occup. Environ. Health 9(1):30-39 (2003).
Reiter, Bruno et al. "Nonspecific Bactericidal Activity of the Lactoperoxidase-Thiocyanate-Hydrogen Peroxide System of Milk Against *Escherichia coli* and Some Gram-Negative Pathogens," Infection and Immunity, 13(3), 800-807 (1976).

Sigma Chemical Corporation and Kessey, J. (1994) Enzymatic Assay of Choline Oxidase (EC 1.1.3.17). https://www.sigmaaldrich.com/content/dam/sigma-aldrich/docs/Sigma/Enzyme_Assay/c5896enz.pdf.
Smith, Temple F. et al. "Comparison of Biosequences," Adv. Appl. Math. 2:482-489 (1981).
Tang, Cuyue et al. "Major Role of Human Liver Microsomal Cytochrome P450 2C9 (CYP2C9) in the Oxidative Metabolism of Celecoxib, a Novel Cyclooxygenase-II Inhibitor," J. Pharm. Exp. Therap., 293(2):453-459 (2000).
Trefzer, Axel et al. "Biocatalytic Conversion of Avermectin to 4"-Oxo-Avermectin: Improvement of Cytochrome P450 Monooxygenase Specificity by Directed Evolution," Appl. Environ. Microbiol. 73(13):4317-4325 (2007).
Wilbur, Karl M. et al. "Electrometric and Colorimetric Determination of Carbonic Anhydrase," J. Biol. Chem. 176:147-154 (1948).
Xia, Menghang et al. "Compound Cytotoxicity Profiling Using Quantitative High-Throughput Screening," Environmental Health Perspectives, 116(3):284-291 (2008).
Zhu, Mingshe et al. "Cytochrome P450 3A-Mediated Metabolism of Buspirone in Human Liver Microsomes," Drug Metabolism and Disposition 33(4):500-507 (2005).
World Health Day, Combat Drug Resistance: No Action Today Means No Cure Tomorrow, Statement by WHO Director-General, Dr. Margaret Chan, Apr. 6, 2011, http://www.who.int/mediacentre/news/statements/2011/whd_20110407/en/. Downloaded Mar. 4, 2018.
Antibiotic Resistance Threats in the United States, 2013, Centers for Disease Control and Prevention: Atlanta, GA, http://www.cdc.gov/drugresistance/threat-report-2013/. Downloaded Mar. 4, 2018.
Roberts, Rebecca R. et al. "Hospital and Societal Costs of Antimicrobial-Resistant Infections in a Chicago Teaching Hospital: Implications for Antibiotic Stewardship," Clin. Infect. Dis. 49(8):1175-84 (2009).
Hoffmann, S. et al. Making Sense of Recent Cost-of-Foodborne-Illness Estimates, United States Department of Agriculture, Economic Research Service, 2013, http://www.ers.usda.gov/publications/eib-economic-information-bulletin/eib118.aspx. Downloaded Mar. 4, 2018.
U.S. Department of Health and Human Services Food and Drug Administration Center for Drug Evaluation and Research (CDER)"Safety Testing of Drug Metabolites Guidance for Industry", Nov. 2016.
Supplementary European Search Report dated Sep. 29, 2016 issued in EP 13 84 4083.9.
Supplementary Partial European Search Report dated Apr. 29, 2016 issued in EP 13844083.9.
Ping, Z. et al., "Research and application of magnetic fluidized bed", Chemical Industry and Engineering Progress, (Apr. 25, 2006), pp. 371-377, with English absttract.
Chinese Office Action dated Mar. 23, 2016 issued in corresponding Chinese Patent Application No. 201380063389.8 with English-language translation.
Abdullah M. et al., "Preparation of Oxide Particles with Ordered Macropores by Colloidal Templating and Spray Pyrolysis", Acta Materialia 52:5151-5156 (2004).
Davis, M. et al., "Formation of Three-Dimensional Ordered Hierarchically Porous Metal Oxides Vi Hybridized Epoxide Assisted/Colloidal Templating Approach", ACS Applied Materials & Interfaces 5:7786-7792 (2013).
Niu T. et al., "Preparation of Meso-Macroporous alpha-Alumina Using Carbon Nanotube as the Template for the Mesopore and Their Application to the Preferential Oxidation of CO in H2-Rich Gases", J Porous Mater 20:789-798 (2013).
Seelan S. et al., "Macroporous Ceramics Coated With Mesoporous Layer for Enzyme Encapsulation", Key Engineering Materials 317-318: 717-722 (2006).
Veitch N.C., "Horseradish Peroxidase: A Modern View of a Classic Enzyme", Phytochemistry 65:249-259 (2004).
Yang L. et al., "Robust Macroporous Materials of Chiral Polyaniline Composites", Chem. Mater. 18(2): 297-300 (2006).
Kim, M. et al., Colorimetric Quantification of Galactose Using a Nanostructured Multicatalyst System . . . Analyst 137(5) 1137-1143, 2012.

(56) References Cited

OTHER PUBLICATIONS

Lee J. et al., Magnetically Separable and Highly Stable Enzyme System Based on Crosslinked Enzyme Aggregates Shipped in Magnetite Coated Mesoporous Silica J of Materials Chemistry 19(42)864-70, 2009.

MeSH Lactoperoxidase information downloaded Oct. 1, 2018 at https:/lwww.ncbi.nlm.nih.gov/mesh/?term=lactoperoxidase.

\* cited by examiner

AUTOMATED BIONANOCATALYST PRODUCTION

CROSS REFERENCE TO RELATED APPLICATIONS

This application is the National Phase Application of PCT/US2016/041461 filed Jul. 8, 2016 and claims the benefit of U.S. Provisional Application No. 62/193,041, filed on Jul. 15, 2015 which is incorporated herein by reference in its entirety.

This invention was made with Government support under SBIR Grant Nos. 1345963 and 145627 awarded by the National Science Foundation. The Government has certain rights in this invention.

FIELD OF THE INVENTION

The present invention provides machines, compositions and methods for producing bionanocatalysts (BNCs) comprising one or more enzymes selected from a broad spectrum of industrially and medically important enzymes.

BACKGROUND OF THE INVENTION

Magnetic enzyme immobilization involves the entrapment of enzymes in mesoporous magnetic clusters that self-assemble around the enzymes. The immobilization efficiency depends on a number of factors that include the initial concentrations of enzymes and nanoparticles, the nature of the enzyme surface, the electrostatic potential of the enzyme, the nanoparticle surface, and the time of contact. Enzymes used for industrial purposes in biocatalytic processes should be highly efficient, stable before and during the process, reusable over several biocatalytic cycles, and economical.

SUMMARY OF THE INVENTION

The present invention provides machines, compositions and methods for producing bionanocatalysts (BNCs) comprising one or more enzymes selected from a broad spectrum of industrially and medically important enzymes. The BNCs are self-assembled and magnetically immobilize enzymes in magnetic nanoparticles. The methods may prevent loss of enzyme activity upon immobilization and maximize enzyme loading. The machines, compositions, and methods are fully scalable from bench top to industrial manufacturing volumes and quantities.

Thus, the invention provides a machine for the automated production of bionanocatalysts (BNC), comprising: an enzyme container; a magnetic nanoparticle (MNP) container; an enzyme pump; an MNP pump; an MNP disruptor; and a BNC mixer; wherein the enzyme container is operable to hold an enzyme preparation; wherein the enzyme preparation catalyzes the conversion of a diffusible substrate to a diffusible product; wherein the MNP container is operable to hold an MNP preparation; wherein said MNP pump is operable to send the MNP preparation to the MNP disruptor; wherein the MNP pump is operable to send a plurality of disrupted MNPs from the MNP disruptor to said BNC mixer; wherein the enzyme pump is operable to send an enzyme preparation to the BNC mixer; wherein the mixer is operable to mix the disrupted MNPs and enzyme preparation to form said BNCs.

In one embodiment, the MNP disruptor is a sonicator. In a preferred embodiment, the sonicator further comprises a sonicator coil and a sonication container, wherein the sonicator coil is operable to sonicate the MNPs within said sonication container. In other embodiments, the sonicator is an in-line sonicator.

In another embodiment, the machine comprises a cooling system operable for cooling said sonicator. In a preferred embodiment, the cooling system is a water cooling system.

In another embodiment, the MNP disruptor is operable to mechanically disrupt the MNPs. In another embodiment, the MNP disruptor is operable to magnetically disrupt the MNPs. In another embodiment, the MNP disruptor is operable to thermally disrupt the MNPs.

In another embodiment the BNC mixer comprises a mixing tee. In another embodiment, the BNC mixer comprises a mixing coil.

In another embodiment, the enzyme pump sends the enzyme preparation to the BNC mixer via mechanical or gravitational force. In another embodiment, the MNP pump sends the MNP preparation to the MNP disruptor via mechanical or gravitational force.

In another embodiment, the machine further comprises a magnetic scaffolding container operable for mixing a magnetic scaffolding preparation with the BNCs in the scaffolding container to produce BNCs in a level 2 assembly. In a preferred embodiment, the magnetic scaffolding container is operable to mix the BNCs and the Scaffolding mechanically. In another preferred embodiment, the magnetic scaffolding container is operable to mix the BNCs and the scaffolding magnetically.

In another embodiment, the machine further comprises a templator for assembling the BNCs into a stabilizing level 2 assembly. In a preferred embodiment, the level 2 assembly is magnetic. In a more preferred embodiment, the magnetic level 2 assembly is a Magnetic Microparticle (MMP).

The invention provides a method of producing BNCs, comprising combining the MNP preparation with the enzyme preparation using the machines described herein, wherein the enzyme preparation comprises an enzyme selected from the group consisting of hydrolases, hydroxylases, hydrogen peroxide producing enzymes (HPP), nitrilases, hydratases, isomerases, synthetases, dehydrogenases, catalases, transaminases, ene reductases (EREDS), imine reductases (IREDS), oxidases, oxidoreductases, peroxidases, oxynitrilases, and isomerases.

In on embodiment, the BNCs are produced in a volume of less than about 1 ml. In a preferred embodiment, the BNCs are produced in a volume of between about 1 ml and 10 ml. In another preferred embodiment, the said BNCs are produced in a volume of between about 10 ml and 100 ml. In another preferred embodiment, the BNCs are produced in a volume of between about 100 ml and 1 liter. In another preferred embodiment, the BNCs are produced in a volume of between about 1 liter and 10 liters. In another preferred embodiment, the BNCs are produced in a volume of between about 10 liters and 100 liters. In another preferred embodiment, the BNCs are produced in a volume of between about 100 liters and 1000 liters. In another preferred embodiment, the BNCs are produced in a volume of between about 1 kiloliter and 10 kiloliters. In another preferred embodiment, the BNCs are produced in a volume of between about 10 kiloliters and 20 kiloliters. In another preferred embodiment, the BNCs are produced in a volume of between about 20 kiloliters and 50 kiloliters. In another preferred embodiment, the BNCs are produced in a volume of greater than about 50 kiloliters.

In another embodiment, the methods provided herein further comprise the step of templating said BNC into a stabilizing level 2 assembly.

The invention provides a self-assembled bionanocatalyst (BNC) composition, comprising magnetic nanoparticles (MNPs) and an enzyme selected from the group consisting of hydrolases, hydroxylases, nitrilases, hydratases, transaminases, ene reductases (EREDS), imine reductases (IREDS), oxynitrilases, and isomerases; wherein the enzyme preparation catalyzes the conversion of a diffusible substrate to a diffusible product.

In some embodiments of the BNC composition, the enzyme is at a concentration of about 5-2,000 μg per ml of total solution and the MNPs are at a concentration of about 50-20,000 μg per ml of total solution. In a preferred embodiment, the enzyme is at a concentration of about 5-15,000 μg per ml of total solution. In another preferred embodiment, the enzyme is at a concentration of about 5-10,000 μg per ml of total solution. In another preferred embodiment, the enzyme is at a concentration of about 5-5,000 μg per ml of total solution. In another preferred embodiment, the enzyme is at a concentration of about 100-20,000 μg per ml of total solution. In another preferred embodiment, the MNPs are at a concentration of about 500-20,000 μg per ml of total solution. In another preferred embodiment, the MNPs are at a concentration of about 1,000-20,000 μg per ml of total solution. In another preferred embodiment, the MNPs are at a concentration of about 5,000-20,000 μg per ml of total solution. In another preferred embodiment, the MNPs are at a concentration of about 10,000-20,000 μg per ml of total solution. In another preferred embodiment, the MNPs are at a concentration of about 5,000-10,000 μg per ml of total solution.

In another embodiment, the BNC composition further comprises a stabilizing level 2 assembly. In a preferred embodiment, the level 2 assembly is magnetic. In a more preferred embodiment, the magnetic level 2 assembly is a Magnetic Microparticle (MMP).

The invention provides a method of using the BNC compositions described herein comprising contacting BNCs with diffusible substrates and collecting diffusible products.

DETAILED DESCRIPTION OF THE INVENTION

Figure 1:
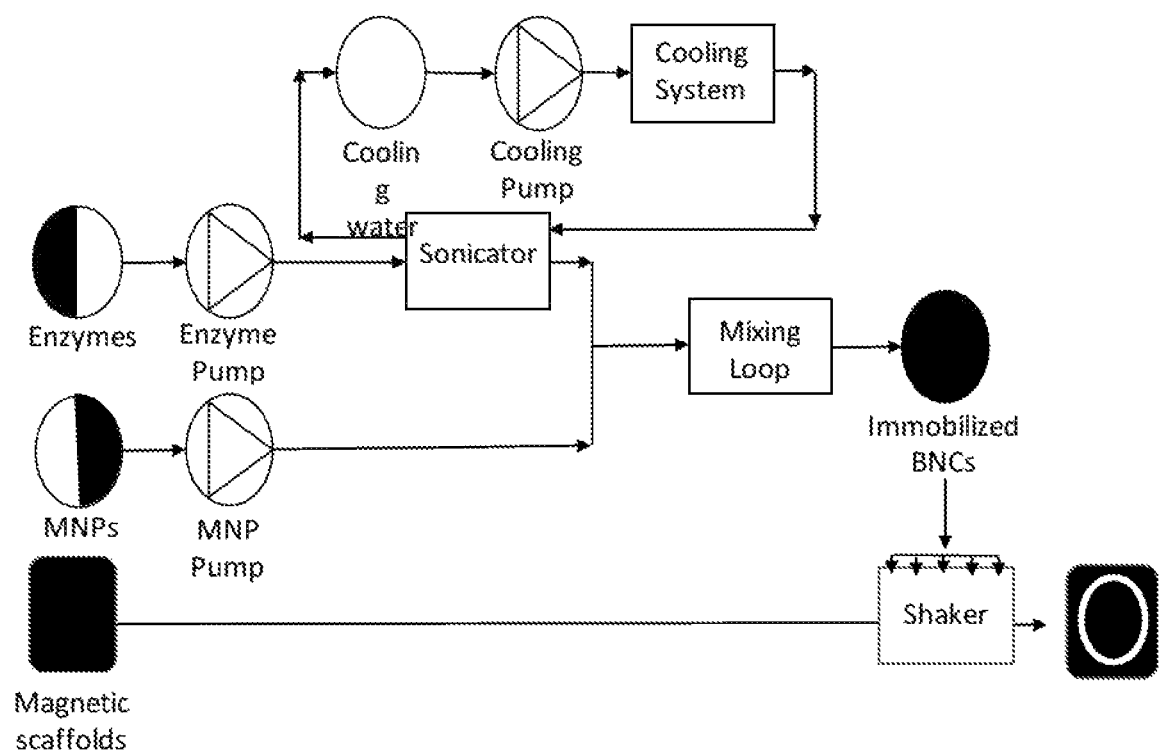
FIG. 1: Schematic diagram of an exemplary machine for the automated production of BNCs.

The present invention provides compositions and methods for producing nanoclusters with very high levels of magnetically-immobilized enzymes. The nanoclusters form by self-assembly and contain 5-20,000 micrograms of enzymes per gram of nanoparticles. The compositions and methods have reduced method steps and chemical reagents and are ideal for scale-up for industrial purposes.

The present invention provides self-assembled mesoporous nanoclusters comprising magnetically-immobilized enzymes that are highly active and stable prior to and during use. The technology is a blend of biochemistry, nanotechnology, and bioengineering at three integrated levels of organization: Level 1 is the self-assembly of enzymes with magnetic nanoparticles (MNP) for the synthesis of magnetic mesoporous nanoclusters. This level uses a mechanism of molecular self-entrapment to immobilize enzymes. An enzyme immobilized in self-assembled magnetic nanoparticles is herein referred to as a "bionanocatalyst" (BNC). Level 2 is the stabilization of the BNCs into other assemblies such as magnetic matrices. In certain embodiments, the BNCs are "templated" onto or into micro or macro structures for commercial or other applications. In one embodiment, the level 2 template is a Magnetic Microparticle (MMP). Level 3 is product conditioning for using the Level 1+2 immobilized enzymes.

The MNPs allow for a broader range of operating conditions for using enzymes in biocatalytic processes such as temperature, ionic strength, pH, and solvents. The size and magnetization of the MNPs affect the formation and structure of the BNCs. This has a significant impact on the activity of the entrapped enzymes. By virtue of their surprising resilience under various reaction conditions, self-assembled MNP clusters can be used as a superior immobilization material for enzymes that replaces polymeric resins, cross-linked gels, cross-linked enzyme aggregates (CLEAs), cross-linked magnetic beads and the like. Furthermore, they can be used in any application of enzymes on diffusible substrates.

BNC's contain mesopores that are interstitial spaces between the clustered magnetic nanoparticles. Enzymes are immobilized within at least a portion of the mesopores of the magnetic BNCs. As used herein, the term "magnetic" encompasses all types of useful magnetic characteristics, including permanent magnetic, superparamagnetic, paramagnetic, and ferromagnetic behaviors.

BNC sizes are in the nanoscale, i.e., generally no more than 500 nm. As used herein, the term "size" can refer to a diameter of the magnetic nanoparticle when the magnetic nanoparticle is approximately or substantially spherical. In a case where the magnetic nanoparticle is not approximately or substantially spherical (e.g., substantially ovoid or irregular), the term "size" can refer to either the longest dimension or an average of the three dimensions of the magnetic nanoparticle. The term "size" may also refer to the calculated average size in a population of magnetic nanoparticles.

In different embodiments, the magnetic nanoparticle has a size of precisely, about, up to, or less than, for example, 500 nm, 400 nm, 300 nm, 200 nm, 100 nm, 50 nm, 40 nm, 30 nm, 25 nm, 20 nm, 15 nm, 10 nm, 5 nm, 4 nm, 3 nm, 2 nm, or 1 nm, or a size within a range bounded by any two of the foregoing exemplary sizes.

Within BNCs, the individual magnetic nanoparticles may be primary nanoparticles (i.e., primary crystallites) having any of the sizes provided above. The aggregates of nanoparticles in a BNC are larger in size than the nanoparticles and generally have a size (i.e., secondary size) of at least about 5 nm. In different embodiments, the aggregates have a size of precisely, about, at least, above, up to, or less than, for example, 5 nm, 8 nm, 10 nm, 12 nm, 15 nm, 20 nm, 25 nm, 30 nm, 35 nm, 40 nm, 45 nm, 50 nm, 60 nm, 70 nm, 80 nm, 90 nm, 100 nm, 150 nm, 200 nm, 300 nm, 400 nm, 500 nm, 600 nm, 700 nm, or 800 nm, or a size within a range bounded by any two of the foregoing exemplary sizes.

Typically, the primary and/or aggregated magnetic nanoparticles or BNCs thereof have a distribution of sizes, i.e., they are generally dispersed in size, either narrowly or broadly dispersed. In different embodiments, any range of primary or aggregate sizes can constitute a major or minor proportion of the total range of primary or aggregate sizes. For example, in some embodiments, a particular range of primary particle sizes (for example, at least about 1, 2, 3, 5, or 10 nm and up to about 15, 20, 25, 30, 35, 40, 45, or 50 nm) or a particular range of aggregate particle sizes (for example, at least about 5, 10, 15, or 20 nm and up to about 50, 100, 150, 200, 250, or 300 nm) constitutes at least or above about 50%, 60%, 70%, 80%, 90%, 95%, 98%, 99%, or 100% of the total range of primary particle sizes. In other embodiments, a particular range of primary particle sizes (for example, less than about 1, 2, 3, 5, or 10 nm, or above about 15, 20, 25, 30, 35, 40, 45, or 50 nm) or a particular range of aggregate particle sizes (for example, less than about 20, 10, or 5 nm, or above about 25, 50, 100, 150, 200, 250, or 300 nm) constitutes no more than or less than about 50%, 40%, 30%, 20%, 10%, 5%, 2%, 1%, 0.5%, or 0.1% of the total range of primary particle sizes.

The aggregates of magnetic nanoparticles (i.e., "aggregates") or BNCs thereof can have any degree of porosity, including a substantial lack of porosity depending upon the quantity of individual primary crystallites they are made of. In particular embodiments, the aggregates are mesoporous by containing interstitial mesopores (i.e., mesopores located between primary magnetic nanoparticles, formed by packing arrangements). The mesopores are generally at least 2 nm and up to 50 nm in size. In different embodiments, the mesopores can have a pore size of precisely or about, for example, 2, 3, 4, 5, 10, 12, 15, 20, 25, 30, 35, 40, 45, or 50 nm, or a pore size within a range bounded by any two of the foregoing exemplary pore sizes. Similar to the case of particle sizes, the mesopores typically have a distribution of sizes, i.e., they are generally dispersed in size, either narrowly or broadly dispersed. In different embodiments, any range of mesopore sizes can constitute a major or minor proportion of the total range of mesopore sizes or of the total pore volume. For example, in some embodiments, a particular range of mesopore sizes (for example, at least about 2, 3, or 5, and up to 8, 10, 15, 20, 25, or 30 nm) constitutes at least or above about 50%, 60%, 70%, 80%, 90%, 95%, 98%, 99%, or 100% of the total range of mesopore sizes or of the total pore volume. In other embodiments, a particular range of mesopore sizes (for example, less than about 2, 3, 4, or 5 nm, or above about 10, 15, 20, 25, 30, 35, 40, 45, or 50 nm) constitutes no more than or less than about 50%, 40%, 30%, 20%, 10%, 5%, 2%, 1%, 0.5%, or 0.1% of the total range of mesopore sizes or of the total pore volume.

The magnetic nanoparticles can have any of the compositions known in the art. In some embodiments, the magnetic nanoparticles are or include a zerovalent metallic portion that is magnetic. Some examples of such zerovalent metals include cobalt, nickel, and iron, and their mixtures and alloys. In other embodiments, the magnetic nanoparticles are or include an oxide of a magnetic metal, such as an oxide of cobalt, nickel, or iron, or a mixture thereof. In some embodiments, the magnetic nanoparticles possess distinct core and surface portions. For example, the magnetic nanoparticles may have a core portion composed of elemental iron, cobalt, or nickel and a surface portion composed of a passivating layer, such as a metal oxide or a noble metal coating, such as a layer of gold, platinum, palladium, or silver. In other embodiments, metal oxide magnetic nanoparticles or aggregates thereof are coated with a layer of a noble metal coating. The noble metal coating may, for example, reduce the number of charges on the magnetic nanoparticle surface, which may beneficially increase dispersibility in solution and better control the size of the BNCs. The noble metal coating protects the magnetic nanoparticles against oxidation, solubilization by leaching or by chelation when chelating organic acids, such as citrate, malonate, or tartrate, are used in the biochemical reactions or processes. The passivating layer can have any suitable thickness, and particularly, at least, up to, or less than, about for example, 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, or 10 nm, or a thickness in a range bounded by any two of these values.

Magnetic materials useful for the invention are well-known in the art. Non-limiting examples comprise ferromagnetic and ferromagnetic materials including ores such as iron ore (magnetite or lodestone), cobalt, and nickel. In other embodiments, rare earth magnets are used. Non-limiting examples include neodymium, gadolinium, sysprosium, samarium-cobalt, neodymium-iron-boron, and the like. In yet further embodiments, the magnets comprise composite materials. Non-limiting examples include ceramic, ferrite, and alnico magnets. In preferred embodiments, the magnetic nanoparticles have an iron oxide composition. The iron oxide composition can be any of the magnetic or superparamagnetic iron oxide compositions known in the art, e.g., magnetite ($FesO/O$, hematite ($\alpha$-$Fe2\theta$ 3), maghemite ($\gamma$-$Fe2C>3$), or a spinel ferrite according to the formula $AB_2O_4$, wherein A is a divalent metal (e.g., $Xn^{2+}$, $Ni^{2+}$, $Mn^{2+}$, $Co^{2+}$, $Ba^{2+}$, $Sr^{2+}$, or combination thereof) and B is a trivalent metal (e.g., $Fe^{3+}$, $Cr^+$, or combination thereof).

In particular embodiments, the above mesoporous aggregates of magnetic nanoparticles (BNCs) are incorporated into a continuous macroporous scaffold to form a hierarchical catalyst assembly with first and second levels of assembly. The first level of assembly is found in the BNCs. The second level of assembly is found in the incorporation of the BNCs into the continuous macroporous scaffold. In some embodiments, the level 2 assembly is magnetic.

The term "continuous", as used herein for the macroporous magnetic scaffold, indicates a material that is not a particulate assembly, i.e., is not constructed of particles or discrete objects assembled with each other to form a macroscopic structure. In contrast to a particulate assembly, the continuous structure is substantially seamless and uniform around macropores that periodically interrupt the seamless and uniform structure. The macropores in the continuous scaffold are, thus, not interstitial spaces between agglomerated particles. Nevertheless, the continuous scaffold can be constructed of an assembly or aggregation of smaller primary continuous scaffolds, as long as the assembly or aggregation of primary continuous scaffolds does not include macropores (e.g., greater than about 50 nm and up to about 100) formed by interstitial spaces between primary continuous scaffolds. Particularly in the case of inorganic materials such as ceramics or elemental materials, the continuous scaffold may or may not also include crystalline domains or phase boundaries.

The terms "percent immobilization yield" or "% immobilization yield" refer to the percent of an enzyme, measured by mass or activity, that is captured in an immobilizate or nanoparticle preparation when compared to an initial quantity of enzyme in a sample prior to immobilization.

In particular embodiments, the above mesoporous aggregates of magnetic nanoparticles (BNCs) are incorporated into a continuous macroporous scaffold to form a hierarchical catalyst assembly with first and second levels of assembly. The first level of assembly is found in the BNCs. The second level of assembly is found in the incorporation of the BNCs into the continuous macroporous scaffold. The overall hierarchical catalyst assembly is magnetic by at least the presence of the BNCs.

The macroporous scaffold contains macropores (i.e., pores of a macroscale size) having a size greater than 50 nm. In different embodiments, the macropores have a size of precisely, about, at least, above, up to, or less than, for example, 60 nm, 70 nm, 80 nm, 90 nm, 100 nm, 150 nm, 200 nm, 300 nm, 400 nm, 500 nm, 600 nm, 700 nm, 800 nm, 900 nm, 1 micron (1 µm), 1.2 µm, 1.5 µm, 2 µm, 3 µm, 4 µm, 5 µm, 10 µm, 20 µm, 30 µm, 40 µm, 50 µm, 60 µm, 70 µm, 80 µm, 90 µm, or 100 µm, or a size within a range bounded by any two of the foregoing exemplary sizes.

The macroporous scaffold can have any suitable size as long as it can accommodate macropores. In typical embodiments, the macroporous scaffold possesses at least one size dimension in the macroscale. The at least one macroscale dimension is above 50 nm, and can be any of the values provided above for the macropores, and in particular, a dimension of precisely, about, at least, above, up to, or less than, for example, 1 µm, 2 µm, 3 µm, 4 µm, 5 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 5 mm, or 1 cm, or a size within a range bounded by any two of the foregoing exemplary sizes. Where only one or two of the size dimensions are in the macroscale, the remaining one or two dimensions can be in the nanoscale, such as any of the values provided above for the magnetic nanoparticles (e.g., independently, precisely, about, at least, above, up to, or less than, for example, 1, 2, 3, 4, 5, 10, 20, 30, 40, 50, 60, 70, 80, 90, or 100 nm, or a value within a range bounded by any two of the foregoing values). In some embodiments, at least two or all of the size dimensions of the macroporous scaffold is in the macroscale.

In a first set of embodiments, the continuous macroporous scaffold in which the BNCs are incorporated is magnetic, i.e., even in the absence of the BNCs. The continuous macroporous scaffold can be magnetic by, for example, being composed of a magnetic polymer composition. An example of a magnetic polymer is PANiCNQ, which is a combination of tetracyanoquinodimethane (TCNQ) and the emeraldine-based form of polyaniline (PANi), as well known in the art. Alternatively, or in addition, the continuous macroporous scaffold can be magnetic by having embedded therein magnetic particles not belonging to the BNCs. The magnetic particles not belonging to the BNCs may be, for example, magnetic nano- or micro-particles not associated with an FRP enzyme or any enzyme. The magnetic microparticles may have a size or size distribution as provided above for the macropores, although independent of the macropore sizes. In particular embodiments, the magnetic microparticles have a size of about, precisely, or at least 20, 30, 40, 50, 60, 70, 80, 90, 100, 100, 200, 300, 400, 500, 600, 700, 800, 900, 1000 nm, or a size within a range bounded by any two of the foregoing exemplary sizes. In some embodiments, the continuous macroporous scaffold has embedded therein magnetic microparticles that are adsorbed to at least a portion of the BNCs, or wherein the magnetic microparticles are not associated with or adsorbed to the BNCs.

In a second set of embodiments, the continuous scaffold in which the BNCs are incorporated is non-magnetic. Nevertheless, the overall hierarchical catalyst assembly containing the non-magnetic scaffold remains magnetic by at least the presence of the BNCs incorporated therein.

In one embodiment, the continuous macroporous scaffold (or precursor thereof) has a polymeric composition. The polymeric composition can be any of the solid organic, inorganic, or hybrid organic-inorganic polymer compositions known in the art, and may be synthetic or a biopolymer that acts as a binder. Preferably, the polymeric macroporous scaffold does not dissolve or degrade in water or other medium in which the hierarchical catalyst is intended to be used. Some examples of synthetic organic polymers include the vinyl addition polymers (e.g., polyethylene, polypropylene, polystyrene, polyacrylic acid or polyacrylate salt, polymethacrylic acid or polymethacrylate salt, poly(methylmethacrylate), polyvinyl acetate, polyvinyl alcohol, and the like), fluoropolymers (e.g., polyvinylfluoride, polyvinylidenefluoride, polytetrafluoroethylene, and the like), the epoxides (e.g., phenolic resins, resorcinol-formaldehyde resins), the polyamides, the polyurethanes, the polyesters, the polyimides, the polybenzimidazoles, and copolymers thereof. Some examples of biopolymers include the polysaccharides (e.g., cellulose, hemicellulose, xylan, chitosan, inulin, dextran, agarose, and alginic acid), polylactic acid, and polyglycolic acid. In the particular case of cellulose, the cellulose may be microbial- or algae-derived cellulose. Some examples of inorganic or hybrid organic-inorganic polymers include the polysiloxanes (e.g., as prepared by sol gel synthesis, such as polydimethylsiloxane) and polyphosphazenes. In some embodiments, any one or more classes or specific types of polymer compositions provided above are excluded as macroporous scaffolds.

In another embodiment, the continuous macroporous scaffold (or precursor thereof) has a non-polymeric composition. The non-polymeric composition can have, for example, a ceramic or elemental composition. The ceramic composition may be crystalline, polycrystalline, or amorphous, and may have any of the compositions known in the art, including oxide compositions (e.g., alumina, beryllia, ceria, yttria, or zirconia) and non-oxide compositions (e.g., carbide, silicide, nitride, boride, or sulfide compositions). The elemental composition may also be crystalline, polycrystalline, or amorphous, and may have any suitable elemental composition, such as carbon, aluminum, or silicon.

In other embodiments, the BNCs reside in a non-continuous macroporous support containing (or constructed of) an assembly (i.e., aggregation) of Magnetic Microparticles (MMPs) that includes macropores as interstitial spaces between the magnetic microparticles. The magnetic microparticles are typically ferromagnetic and can be made of magnetite or other ferromagnetic materials. The BNCs are embedded in at least a portion of the macropores of the aggregation of magnetic microparticles, and may also reside on the surface of the magnetic microparticles. The BNCs can associate with the surface of the magnetic microparticles by magnetic interaction. The magnetic microparticles may or may not be coated with a metal oxide or noble metal coating layer. In some embodiments, the BNC-MMP assembly is incorporated (i.e., embedded) into a continuous macroporous scaffold, as described above, to provide a hierarchical catalyst assembly.

The individual magnetic nanoparticles or aggregates thereof or BNCs thereof possess any suitable degree of magnetism. For example, the magnetic nanoparticles, BNCs, or BNC scaffold assemblies can possess a saturated magnetization (Ms) of at least or up to about 5, 10, 15, 20, 25, 30, 40, 45, 50, 60, 70, 80, 90, or 100 emu/g. The magnetic nanoparticles, BNCs, or BNC-scaffold assemblies preferably possess a remanent magnetization (Mr) of no more than (i.e., up to) or less than 5 emu/g, and more preferably, up to or less than 4 emu/g, 3 emu/g, 2 emu/g, 1 emu/g, 0.5 emu/g, or 0.1 emu/g. The surface magnetic field of the magnetic nanoparticles, BNCs, or BNC-scaffold assemblies can be about or at least, for example, about 0.5, 1, 5, 10, 50, 100, 200, 300, 400, 500, 600, 700, 800, 900, or 1000 Gauss (G), or a magnetic field within a range bounded by any two of the foregoing values. If microparticles are included, the microparticles may also possess any of the above magnetic strengths.

The magnetic nanoparticles or aggregates thereof can be made to adsorb a suitable amount of enzyme, up to or below a saturation level, depending on the application, to produce the resulting BNC. In different embodiments, the magnetic nanoparticles or aggregates thereof may adsorb about, at least, up to, or less than, for example, 1, 5, 10, 15, 20, 25, or 30 μmol/m$^2$ of enzyme. Alternatively, the magnetic nanoparticles or aggregates thereof may adsorb an amount of enzyme that is about, at least, up to, or less than, for example, about 10%, 20%, 30%, 40%, 50%, 60%, 70%, 80%, 90%, or 100% of a saturation level.

The magnetic nanoparticles or aggregates thereof or BNCs thereof possess any suitable pore volume. For example, the magnetic nanoparticles or aggregates thereof can possess a pore volume of about, at least, up to, or less than, for example, about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm$^3$/g, or a pore volume within a range bounded by any two of the foregoing values. The magnetic nanoparticles or aggregates thereof or BNCs thereof possess any suitable specific surface area. For example, the magnetic nanoparticles or aggregates thereof can have a specific surface area of about, at least, up to, or less than, for example, about 50, 60, 70, 80, 90, 100, 110, 120, 130, 140, 150, 160, 170, 180, 190, or 200 m$^2$/g.

MNPs, their structures, organizations, suitable enzymes, and uses are described in WO2012122437, WO2014055853, and U.S. Provisional Application No. 62/163,032, incorporated by reference herein in their entirety.

Some embodiments of the invention comprise hydrolases. Hydrolases catalyze the hydrolysis of many types of chemical bonds by using water as a substrate. The substrates typically have hydrogen and hydroxyl groups at the site of the broken bonds. Hydrolases are classified as EC 3 in the EC number classification of enzymes. Hydrolases can be further classified into several subclasses, based upon the bonds they act upon. Exemplary hydrolases and the bonds they hydrolyze include EC 3.1: ester bonds (esterases: nucleases, phosphodiesterases, lipase, phosphatase), EC 3.2: sugars (DNA glycosylases, glycoside hydrolase), EC 3.3: ether bonds, EC 3.4: peptide bonds (Proteases/peptidases), EC 3.5: carbon-nitrogen bonds, other than peptide bonds, EC 3.6 acid anhydrides (acid anhydride hydrolases, including helicases and GTPase), EC 3.7 carbon-carbon bonds, EC 3.8 halide bonds, EC 3.9: phosphorus-nitrogen bonds, EC 3.10: sulphur-nitrogen bonds, EC 3.11: carbon-phosphorus bonds, EC 3.12: sulfur-sulfur bonds, and EC 3.13: carbon-sulfur bonds.

In some preferred embodiments, the hydrolase is a glycoside hydrolase. These enzymes have a variety of uses including degradation of plant materials (e.g. cellulases for degrading cellulose to glucose that are used for ethanol production), food manufacturing (e.g. sugar inversion, maltodextrin production), and paper production (removing hemicelluloses from paper pulp).

In some preferred embodiments, the hydrolase is lipolase 100 L (EC 3.1.1.3). It is used to synthesize pregabalin (marketed as by Pfizer as Lyrica®), an anticonvulsant drug used for neuropathic pain, anxiety disorders, and epilepsy. These conditions affect about 1% of the world's population. Lipolase 100 L was found to reduce the required starting material by 39% and cut the waste per unit by 80%.

In some preferred embodiments, the hydrolase is a gamma-lactamase (e.g. EC 3.1.5.49). It is used to make Vince lactam, an intermediate for abacavir production (an antiretroviral drug for treating HIV/AIDS). It was found that changing from a stoichiometric process to a catalytic flow process reduced the number of unit operations from 17 to 12 and reduced the waste by 35%. Additionally, the use of the toxic substance cyanogen chloride is minimized.

In some preferred embodiments, the hydrolase is a Lactase (e.g. EC 3.2.1.108). These enzymes break apart lactose in milk into simple sugars to produce lactose-free milk. This important product serves approximately 15% of the world population that is lactose intolerant.

In some preferred embodiments, the hydrolase is a penicillin amidase (e.g. EC 3.5.1.11). These enzymes split penicillin into a carboxylate and 6-aminopenicillanate (6-APA). 6-APA is the core structure in natural and synthetic penicillin derivatives. These enzymes are used to produce semisynthetic penicillins tailored to fight specific infections.

In some preferred embodiments, the hydrolase is a nitrilase (e.g. EC 3.5.5.1). These enzymes split nitriles into carboxyl groups and liberate ammonia. They are active on diverse aliphatic and aromatic nitrile compounds, some of whose corresponding carboxylic acids are of industrial significance. Gong et al., *Microbial Cell Factories* 11(1):142 (2012). Nitrilases are utilized to produce nicotinic acid, also known as vitamin B3, or niacin, from 3-cyanopyridine. Shaw et al., *Adv. Synth. and Catalysis* 345(4): 425-435 (2003). Nicotinic acid has application as a nutritional supplement in foods and as a pharmaceutical intermediate. For instance, a nitrilase is used to manufacture atorvastatin (marketed by Pfizer as Lipitor®). It catalyzes the reaction of meso-3-hydroxyglutaronitrile to ethyl (R)-4-cyano-3-hydroxybutyrate, the latter of which form the core of atorvastatin.

Hydrolases are discussed in the following references, incorporated herein by reference in their entirety: Anastas, P. T. *Handbook of Green Chemistry*. Wiley-VCH-Verlag, 2009; Dunn, Peter J., Andrew Wells, and Michael T. Williams, eds. *Green chemistry in the pharmaceutical industry*.

John Wiley & Sons, 2010.; Martinez et al., *Curr. Topics Med. Chem.* 13(12):1470-90 (2010); Wells et al., *Organic Process Res. Dev.* 16(12):1986-1993 (2012).

In some embodiments, the invention provides hydrogen peroxide producing (HPP) enzymes. In certain embodiments, the HPP enzymes are oxidases that may be of the EX 1.1.3 subgenus. In particular embodiments, the oxidase may be EC 1.1.3.3 (malate oxidase), EC 1.1.3.4 (glucose oxidase), EC 1.1.3.5 (hexose oxidase), EC 1.1.3.6 (cholesterol oxidase), EC 1.1.3.7 (aryl-alcohol oxidase), EC 1.1.3.8 (L-gulonolactone oxidase), EC 1.1.3.9 (galactose oxidase), EC 1.1.3.10 (pyranose oxidase), EC 1.1.3.11 (L-sorbose oxidase), EC 1.1.3.12 (pyridoxine 4-oxidase), EC 1.1.3.13 (alcohol oxidase), EC 1.1.3.14 (catechol oxidase), EC 1.1.3.15 (2-hydroxy acid oxidase), EC 1.1.3.16 (ecdysone oxidase), EC 1.1.3.17 (choline oxidase), EC 1.1.3.18 (secondary-alcohol oxidase), EC 1.1.3.19 (4-hydroxymandelate oxidase), EC 1.1.3.20 (long-chain alcohol oxidase), EC 1.1.3.21 (glycerol-3-phosphate oxidase), EC 1.1.3.22, EC 1.1.3.23 (thiamine oxidase), EC 1.1.3.24 (L-galactonolactone oxidase), EC 1.1.3.25, EC 1.1.3.26, EC 1.1.3.27 (hydroxyphytanate oxidase), EC 1.1.3.28 (nucleoside oxidase), EC 1.1.3.29 (Nacylhexosamine oxidase), EC 1.1.3.30 (polyvinyl alcohol oxidase), EC 1.1.3.31, EC 1.1.3.32, EC 1.1.3.33, EC 1.1.3.34, EC 1.1.3.35, EC 1.1.3.36, EC 1.1.3.37 D-arabinono-1,4-lactone oxidase), EC 1.1.3.38 (vanillyl alcohol oxidase), EC 1.1.3.39 (nucleoside oxidase, $H_2O_2$ forming), EC 1.1.3.40 (D-mannitol oxidase), or EC 1.1.3.41 (xylitol oxidase).

Some embodiments of the invention may comprise hydroxylases. Hydroxylation is a chemical process that introduces a hydroxyl group (—OH) into an organic compound. Hydroxylation is the first step in the oxidative degradation of organic compounds in air. Hydroxylation plays a role in detoxification by converting lipophilic compounds into hydrophilic products that are more readily excreted. Some drugs (e.g. steroids) are activated or deactivated by hydroxylation. Hydroxylases are well-known in the art. Exemplary hydroxylases include proline hydroxylases, lysine hydroxylases, and tyrosine hydroxylases.

Some embodiments of the invention comprise Nitrilases (NIT). They are hydrolyzing enzymes (EC 3.5.5.1) that catalyze the hydrolysis of nitriles into chiral carboxylic acids with high enantiopurity and ammonia. NIT activity may be measured by monitoring the conversion of mandelonitirile into a (R)-mandelic acid. This results in a pH drop that may be monitored spectrophotometrically.

Some embodiments of the invention comprise hydratases. They are enzymes that catalyze the addition or removal of the elements of water. Hydratases, also known as hydrolyases or hydrases, may catalyze the hydration or dehydration of C—O linkages.

Some embodiments of the invention comprise oxidoreductases. These enzymes catalyze the transfer of electrons from one molecule to another. This involves the transfer of H and O atoms or electrons from one substance to another. They typically utilize NADP or NAD+ as cofactors.

In some preferred embodiments of the invention, Oxidoreductases are used for the decomposition of pollutants such as polychlorinated biphenyls and phenolic compounds, the degradation of coal, and the enhancement of the fermentation of wood hydrolysates. The invention further includes their use in biosensors and disease diagnosis.

In some preferred embodiments, the oxidoreductase is a dehydrogenase (DHO). This group of oxidoreductases oxidizes a substrate by a reduction reaction that transfers one or more hydrides (H—) to an electron acceptor, usually NAD+/NADP+ or a flavin coenzyme such as FAD or FMN. Exemplary dehydrogenases include aldehyde dehydrogenase, acetaldehyde dehydrogenase, alcohol dehydrogenase, glutamate dehydrogenase, lactate dehydrogenase, pyruvate dehydrogenase, glucose-6-phosphate dehydrogenase, glyceraldehyde-3-phosphate dehydrogenase, sorbitol dehydrogenase, isocitrate dehydrogenase, alpha-ketoglutarate dehydrogenase, succinate dehydrogenase, and malate dehydrogenase.

In some preferred embodiments, the oxidoreductase is a ketoreductase (EC 1.1.1.184), an oxidoreductase used to make atorvastatin (marketed by Pfizer as Lipitor®). This biocatalytic process is commercially important because it substantially reduces starting materials, limits the use of organic solvents, and increases the biodegradability of the waste streams.

In some preferred embodiments, the oxidoreductase is a glucose dehydrogenase (e.g. EC 1.1.99.10). They are used by pharmaceutical companies to recycle cofactors used in drug production. They catalyze the transformation of glucose into gluconate. NADP+ is reduced to NADPH. This is used in Avastan production.

In some preferred embodiments, the oxidoreductase is P450 (EC 1.14.14.1). It is used in the pharmaceutical industry for difficult oxidations. P450 is used, in some embodiments, to produce chemical and drug metabolites. In preferred embodiments, the cost, consistency, and efficiency of p450s is improved when used in conjunction with a cofactor regenerating system (e.g., NADPH/NADP+) involving glucose dehydrogrennase (GDH) or formate dehydrogenase (FDH).

In some preferred embodiments, the oxidoreductase is a catalase such as EC 1.11.1.6. Catalase is observed in every eukaryotic organism and many prokaryotes. It serves an integral role in the regulation of peroxidative stress through the degradation of hydrogen peroxide into water and oxygen. Catalases are highly active tetramers with four identical subunits that each contains a heme-based active site. Gaetanit & Kirkman, *Proc. Natl. Acad. Sci. USA*. 81(14):4343-7 (1984). Catalase has numerous industrial applications for eliminating or regulating hydrogen peroxide. Examples include removing residual peroxide in textile bleaching, for producing acidity regulators such as gluconic acid, or preventing accumulation of inhibitory concentrations of peroxide in processes utilizing oxidases such as cheese production. Betancor et al., *Biotechnology Progress* 19(3):763-767 (2003).

In some preferred embodiments, the oxidoreductase is a glucose oxidase (e.g. Notatin, EC 1.1.3.4). Glucose oxidase catalyzes the oxidation of glucose to hydrogen peroxide and D-glucono-δ-lactone. It is used, for example, to generate hydrogen peroxide as an oxidizing agent for hydrogen peroxide consuming enzymes such as peroxidase.

In some embodiments, the invention encompasses Free Radical Producing (FRP) enzymes. In some embodiments, the FRP is a peroxidase. Peroxidases are widely found in biological systems and form a subset of oxidoreductases that reduce hydrogen peroxide ($H_2O_2$) to water in order to oxidize a large variety of aromatic compounds ranging from phenol to aromatic amines. Peroxidases are very potent enzymes yet notoriously difficult to deploy in industrial settings due to strong inhibition in presence of excess peroxide. The invention provides increased reaction turnover and reduced inhibition. Thus, enzymes such as Horseradish Peroxidase (HRP) may be used at industrial scales.

Peroxidases belong of the sub-genus EC 1.11.1. In certain embodiments, the EC 1.11.1 enzyme is The EC 1.11.1 enzyme can be more specifically, for example, EC 1.11.1.1 (NADH peroxidase), EC 1.11.1.2 (NADPH peroxidase), EC 1.11.1.3 (fatty acid peroxidase), EC 1.11.1.4, EC 1.11.1.5 (cytochrome-c peroxidase), EC 1.11.1.6 (catalase), EC 1.11.1.7 (peroxidase), EC 1.11.1.8 (iodide peroxidase), EC 1.11.1.9 (glutathione peroxidase), EC 1.11.1.10 (chloride peroxidase), EC 1.11.1.11 (L-ascorbate peroxidase), EC 1.11.1.12 (phospholipid-hydroperoxide glutathione peroxidase), EC 1.11.1.13 (manganese peroxidase), EC 1.11.1.14 (diarylpropane peroxidase), or EC 1.11.1.15 (peroxiredoxin).

In other embodiments, the peroxidase may also be further specified by function, e.g., a lignin peroxidase, manganese peroxidase, or versatile peroxidase. The peroxidase may also be specified as a fungal, microbial, animal, or plant peroxidase. The peroxidase may also be specified as a class I, class II, or class III peroxidase. The peroxidase may also be specified as a myeloperoxidase (MPO), eosinophil peroxidase (EPO), lactoperoxidase (LP), thyroid peroxidase (TPO), prostaglandin H synthase (PGHS), glutathione peroxidase, haloperoxidase, catalase, cytochrome c peroxidase, horseradish peroxidase, peanut peroxidase, soybean peroxidase, turnip peroxidase, tobacco peroxidase, tomato peroxidase, barley peroxidase, or peroxidasin. In particular embodiments, the peroxidase is horseradish peroxidase.

The lactoperoxidase/glucose oxidase (LP/GOX) antimicrobial system occurs naturally in bodily fluids such as milk, saliva, tears, and mucous (Bosch et al., *J. Applied Microbiol.*, 89(2), 215-24 (2000)). This system utilizes thiocyanate (SCN—) and iodide (I—), two naturally occurring compounds that are harmless to mammals and higher organisms (Welk et al. *Archives of Oral Biology*, 2587 (2011)). LP catalyzes the oxidation of thiocyanate and iodide ions into hypothiocyanite (OSCN—) and hypoiodite (OI—), respectively, in the presence of hydrogen peroxide ($H_2O_2$). The $H_2O_2$ in this system is provided by the activity of GOX on β-D-glucose in the presence of oxygen. These free radical compounds, in turn, oxidize sulfhydryl groups in the cell membranes of microbes (Purdy, Tenovuo et al. *Infection and Immunity*, 39(3), 1187 (1983); Bosch et al., *J. Applied Microbiol.*, 89(2), 215-24 (2000), leading to impairment of membrane permeability (Wan, Wang et al. *Biochemistry Journal*, 362, 355-362 (2001)) and ultimately microbial cell death.

Horseradish peroxidase (EC 1.11.1.7) is a heme-containing oxidoreductase enzyme found in the roots of the horseradish plant *A. rusticana*. It is commonly used as a biochemical signal amplifier and tracer, as it usually acts on a chromogenic substrate together with hydrogen peroxide to produce a brightly colored product complex, which improves spectrophotometric detectability of the target molecule(s). This characteristic of horseradish peroxidase (HRP) has been applied to permeability studies of rodent nervous system capillaries. More recently, HRP has been suggested as part of a possible remediation strategy of phenolic wastewaters due to its ability to degrade various aromatic compounds. Chau & Lu, *Anatomy and Embryology*, 194(3):259-269 (1996); Duan et al., *Chem Phys Chem.* 15(5):974-980 (2014).

Some embodiments of the invention comprise transferases. "Transferase" refers to a class of enzymes that transfer specific functional groups from one molecule to another. Examples of groups transferred include methyl groups and glycosyl groups. Transferases are used for treating substances such as chemical carcinogens and environmental pollutants. Additionally, they are used to fight or neutralize toxic chemicals and metabolites found in the human body.

In some preferred embodiments, the transferase is a transaminase. A transaminase or an aminotransferase catalyzes a reaction between an amino acid and an α-keto acid. They are important in the synthesis of amino acids. They are an important indicator of liver damage. In transamination, the $NH_2$ group on one molecule is exchanged with the =O from another group (e.g. a keto group) on the other molecule.

In more preferred embodiments, the transaminase is ω-transaminases (EC 2.6.1.18). It catalyzes the transfer of amino groups from amino donor molecules to the position of a carboxyl group on an amino acceptor Mathew & Yun, *ACS Catalysis* 2(6):993-1001 (2012). These enzymes are observed in every organism and have a significant role in amino acid synthesis and nitrogen metabolism. Due to their high stereoselectivity for substrates and stereospecificity for products, ω-transaminases are utilized to make unnatural amino acids and optically pure chiral amines or keto acids. ω-Transaminases also have applications in biocatalytic chiral resolution of active pharmaceutical intermediates, simplifying the process over conventional chemical methods. Schâtzle, et al., *Analytical Chemistry* 81(19):8244-8248 (2009). It is used, among other things, to synthesize sitagliptin (marketed by Merck and Co. as Januvia®, an antidiabetic drug). Engineered ω-transaminases were found to improve biocatalytic activity by, for example, 25,000 fold, resulting in a 13% overall increase in sitagliptin yield and 19% reduction in overall process waste.

In some preferred embodiments, the transferase is a thymidylate synthetase (e.g. EC 2.1.1.45). These enzymes are used for manufacturing sugar nucleotides and oligosaccharides. They catalyze, for example, the following reaction:

5,10-methylenetetrahydrofolate+dUMP⇌dihydrofolate+dTMP.

In some preferred embodiments, the transferase is a glutathione S-transferase (e.g. EC 2.5.1.18). These enzymes catalyze glutathione into other tripeptides. They are used in the food industry as oxidizing agents as well as in the pharmaceutical industry to make anti-aging drugs and skin formulations.

In some preferred embodiments, the transferase is a glucokinase (e.g. EC 2.7.1.2). These enzymes facilitate the phosphorylation of glucose to glucose-6-phosphate. They are used in the food industry to reduce the glucose concentration in their production streams and as in the pharmaceutical industry to make diabetes drugs.

In some preferred embodiments, the transferase is a riboflavin kinase (e.g. EC 2.7.1.26). In a more preferred embodiment, a riboflavin kinase is used to produce flavin mononucleotide (FMN) in the food industry. FMN is an orange-red food color additive and an agent that breaks down excess riboflavin (vitamin B2). Riboflavin kinase catalyzes, for example, the following reaction:

ATP+riboflavin⇌ADP+Flavin mononucleotide (FMN).

Some embodiments of the invention comprise ene reductases (EREDS). These enzymes catalyze alkene reduction in an NAD(P)H-dependent manner. Examples of ene-reductases include The FMN-containing Old Yellow Enzyme (OYE) family of oxidoreductases (EC 1.6.99), clostridial enoate reductases (EnoRs, C 1.3.1.31), flavin-independent medium chain dehydrogenase/reductases (MDR; EC 1.3.1), short chain dehydrogenase/reductases (SDR; EC 1.1.1.207-8), leukotriene B4 dehydrogenase (LTD), quinone (QOR), progesterone 5b-reductase, rat pulegone reductase (PGR), tobacco double bond reductase (NtDBR), Cyanobacterial OYEs, LacER from *Lactobacillus casei*, Achr-OYE4 from *Achromobacter* sp. JA81, and Yeast OYEs.

Some embodiments of the invention comprise imine reductases (IREDS). Imine reductases (IRED) catalyze the synthesis of optically pure secondary cyclic amines. They may convert a ketone or aldehyde substrate and a primary or secondary amine substrate to form a secondary or tertiary amine product compound. Exemplary IREDs are those from *Paenibacillus elgii* B69, *Streptomyces ipomoeae* 91-03, *Pseudomonas putida* KT2440, and *Acetobacterium woodii*. IREDs are discussed in detail in Int'l Pub. No. WO2013170050, incorporated by reference herein in its entirety.

In some embodiments of the invention, the enzymes are lyases. They catalyze elimination reactions in which a group of atoms is removed from a substrate by a process other than hydrolysis or oxidation. A new double bond or ring structure often results. Seven subclasses of lyases exist. In preferred embodiments, pectin lyase is used to degrade highly esterified pectins (e.g. in fruits) into small molecules. Other preferred embodiments of the invention comprise oxynitrilases (also referred to as mandelonitrile lyase or aliphatic (R)-hydroxynitrile lyase). They cleave mandelonitrile into hydrogen cyanide+benzaldehyde.

In a preferred embodiment, the lyase is a hydroxynitrile lyase (e.g. EC 4.1.2, a mutation of a *Prunus amygdalus* lyase). Hydroxynitrile lyases catalyze the formation of cyanohydrins which can serve as versatile building blocks for a broad range of chemical and enzymatic reactions. They are used to improve enzyme throughput and stability at a lower pH and can be used for producing clopidogrel (Plavix®). The reaction process is described in Glieder et al., *Chem. Int. Ed.* 42:4815 (2003), incorporated by reference herein in its entirety.

In another preferred embodiment, the lyase is 2-deoxy-D-ribose phosphate aldolase (DERA, EC 4.1.2.4). It is used for forming statin side chains, e.g. in Lipitor production.

In another preferred embodiment, the lyase is (R)-mandelonitrile lyase (HNL, EC 4.1.2.10). It is used to synthesize Threo-3-Aryl-2,3-dihydroxypropanoic acid, a precursor cyanohydrin used to produce Diltiazem. Diltiazem is a cardiac drug that treats high blood pressure and chest pain (angina). Lowering blood pressure reduces the risk of strokes and heart attacks. It is a calcium channel blocker. Ditiazem and its production are described in Dadashipour and Asano, *ACS Catal.* 1:1121-49 (2011) and Aehle W. 2008. *Enzymes in Industry, Weiley-VCH Verlag, GmbH Weinheim.* both of which are incorporated by reference in their entirety.

In another preferred embodiment, the lyase is nitrile hydratase (EC 4.2.1). It is used commercially to convert 3-cyanopyridine to nicotinamide (vitamin B3, niacinamide). It is also used in the preparation of levetiracetam, the active pharmaceutical ingredient in Keppra®.

In another preferred embodiment, the lyase is a Phenyl Phosphate Carboxylase. They are used, e.g., for phosphorylating phenol at room temperature and under sub-atmospheric $CO_2$ pressure. These enzymes catalyze the synthesis of 4-OH benzoic acid from phenol and $CO_2$ with 100% selectivity. 4-OH benzoic acid is used in the preparation of its esters. In more preferred embodiments, the enzymes are used for producing parabens that are used as preservatives in cosmetics and opthalmic solutions.

In some embodiments of the invention, the enzyme is a carbonic anhydrase. Carbonic Anhydrase (EC 4.2.1.1) is a ubiquitous metalloenzyme present in every organism. It is among the most efficient enzymes known (Lindskog & Silverman, *New Horizons* 7:175-95 (2000)) and serves multiple physiological roles including $CO_2$ exchange, pH regulation, and $HCO_3^-$ secretion (McCall, et al., *J. Nutrition* 130(5S Suppl):1437S-46S (2000)). Carbonic anhydrase also has potential industrial applications in $CO_2$ sequestration and calcite production (Boone et al., *Int'l J. Chem. Engin.* 2013:22-27 (2013)).

In some embodiments of the invention, the enzyme is an isomerase. Isomerases catalyze molecular isomerizations, i.e. reactions that convert one isomer to another. They can facilitate intramolecular rearrangements in which bonds are broken and formed or they can catalyze conformational changes. Isomerases are well known in the art.

In preferred embodiments, isomerases are used in sugar manufacturing. In more preferred embodiments, the isomerase is Glucose isomerase, EC 5.3.1.18. In other embodiments, the glucose isomerase is produced by *Actinoplanes missouriensis, Bacillus coagulans* or a *Streptomyces* species. Glucose isomerase converts D-xylose and D-glucose to D-xylulose and D-fructose, important reactions in the production of high-fructose corn syrup and in the biofuels sector.

Glucose isomerase (GIS) (EC5.3.1.5) is one of the most widely-used industrial enzymes. It is used to produce high-fructose corn syrup from glucose GIS catalyzes the reversible isomerization of D-(+)-fructose and D-(+)-glucose (Bhosale et al., *Microbiol. Rev.* 60(2):280-300(1996)).

In another preferred embodiment, the isomerase is Maleate cis-trans isomerase (EC 5.2.1.1). It catalyzes the conversion of maleic acid into fumaric acid. Fumaric acid is important for the biocatalytic production of L-aspartic acid, L-malic acid, polyester resins, food and beverage additives, and mordant for dyes.

In another preferred embodiment, the isomerase is linoleate cis-trans isomerase (EC 5.2.1.5). It catalyzes the isomerization of conjugated linoleic acid (CLA). CLA has been reported to have numerous potential health benefits for treating obesity, diabetes, cancer, inflammation, and atherogenesis. Different isomers of CLA may exert differential physiological effects. Thus, the enzyme is used to prepare single isomers.

In another preferred embodiment of the invention, the isomerase is triosephosphate isomerase (EC 5.3.1.1). It catalyzes the interconversion of D-glyceraldehyde 3-phosphate and dihydroxyacetone phosphate. In combination with transketolases or aldolases, triosephosphate isomerase is used in the stereoselective multienzyme synthesis of various sugars or sugar analogs. A preferred embodiment is the one-pot enzymatic preparation of D-xylulose 5-phosphate. This synthesis starts with the retro-aldol cleavage of fructose 1,6-biphosphate by D-fructose 1,6-biphosphate aldolase (EC 4.1.2.13). The following racemization, triosephosphate isomerase facilitates the generation of two equivalents of D-glyceraldehyde 3-phosphate that is converted into xylulose 5-phosphate by transketolase (EC 2.2.1.1).

In other embodiments of the invention, the enzyme is a Ligase. These enzymes catalyze the formation of covalent bonds joining two molecules together, coupled with the hydrolysis of a nucleoside-triphosphate. Ligases are well-known in the art and are commonly used for recombinant nucleic acid applications. In a preferred embodiment, the DNA ligase is EC 6.5.1.1.

In a preferred embodiment, the ligase is Acetyl-CoA Carboxylase (EC 6.4.1.2, ACC). ACC has a role at the junction of the lipid synthesis and oxidation pathways. It is used with the inventions disclosed herein for clinical purposes such as the production of antibiotics, diabetes therapies, obesity, and other manifestations of metabolic syndrome.

In another preferred embodiment, the ligase is Propionyl-CoA Carboxylase (PCC, EC 6.4.1.3). It catalyzes the biotin-dependent carboxylation of propionyl-CoA to produce D-methylmalonyl-CoA in the mitochondrial matrix. Methylmalyl-CoA is an important intermediate in the biosynthesis of many organic compounds as well as the process of carbon assimilation.

In some embodiments, Glutamine synthetase (GluS) (EC 6.3.1.2) is magnetically immobilized. It is found in various parts of the human body including the brain, liver, and kidneys. Glutamine synthetase uses ATP and $NH_3$ (ammonia) to form glutamine from glutamate. Glutamine is an important amino acid that is manufactured for use in pharmaceuticals and health foods. In 2001 the worldwide annual production of L-glutamine was ~2000 metric tons.] Newsholme et al., *Cell Biochem. and Function,* 21(April 2002): 1-9 (2003); Kusumoto, I., *J. Nutrition* 131:2552S-2555S (2001).

In some embodiments, the methods described herein use recombinant cells that express the enzymes used in the invention. Recombinant DNA technology is known in the art. In some embodiments, cells are transformed with expression vectors such as plasmids that express the enzymes. In other embodiments, the vectors have one or more genetic signals, e.g., for transcriptional initiation, transcriptional termination, translational initiation and translational termination. Here, nucleic acids encoding the enzymes may be cloned in a vector so that it is expressed when properly transformed into a suitable host organism. Suitable host cells may be derived from bacteria, fungi, plants, or animals as is well-known in the art.

The invention provides a process for the automated continuous production of BNCs. In some embodiments, machines provide continuous-flow production for enzyme immobilization. In further embodiments, the machines are used at industrial scales.

FIG. 1 shows an exemplary flow diagram for the process. The nanoparticles are ultrasonicated to achieve a monodisperse state. They are mixed with enzymes at controlled ratios and pH's. In some embodiments, after sonication, the nanoparticles are sent to a mixing loop into which the enzymes are separately pumped. In preferred embodiments, BNCs are produced within an incubation loop. Other preferred embodiments vary the flow rate, the length and the diameter of the tubing as known in the continuous flow manufacturing arts. In other embodiments, shortly after incubation, the BNCs are mixed with magnetic scaffolds to form stable level 2 structures that may be stored until their ultimate catalytic use. In preferred embodiments, the BNCs are mixed with the magnetic scaffolds under continuous stirring In some embodiments of the invention, the enzyme preparations are held in an enzyme container prior to mixing with monodispersed MNPs. It may be made of any material that allows for storage under the proper temperature and pH conditions. In some embodiments, the container discourages non-specific binding of the enzyme preparation to the wall of the container. Thus, it could be made of glass, stainless steel, certain plastics, and the like. Similarly, the magnetic nanoparticle (MNP) are held in any suitable container in conditions that prevent surface oxidation of the metal oxides. These conditions might include temperature, pressure or oxygen levels. In other embodiments, the container does not attract the MNPs magnetically.

In some embodiments of the invention, the machines of the invention comprise an enzyme pump. Enzyme pumps send the one or more enzyme preparations, combined, separated, or sequentially, to a BNC mixer via mechanical or gravitational force. Mechanical forces may include positive pressure, negative pressure (vacuum), stirring, and the like. Similarly, in some embodiments of the invention, the machines of the invention comprise an MNP pump that sends said MNP preparation to the MNP disruptor via mechanical or gravitational force. In preferred embodiments, the pumps described herein may function via positive or negative pressure exerted on the enzyme or MNP preparations.

The machines of the invention have an MNP disruptor that yields monodispersed homogenous suspensions of magnetic nanoparticles. In some embodiments, the MNP disruptor is a sonicator or an ultrasonicator. Sonicators that generate ultrasounds are well-known in the art. In preferred embodiments, the sonicator may comprise a sonication wand or extension that comes in contact with the MNP preparation. In more preferred embodiments, the sonicator comprises a sonicator coil and a sonication container or is an online-process sonicator. In yet more preferred embodiments, the machine comprises a cooling system for cooling the sonicator. In a most preferred embodiment, the cooling system uses water.

In other embodiments, the MNP disruptor may mechanically disrupt the MNPs by shaking, vigorous stirring, pressure, passing through a mesh or porous material, or spraying. In other embodiments, the MNP disruptor may chemically disrupt the MNPs by subjecting them to high pH (e.g. above 10) or by functionalizing the surface (e.g. with citrate or small linear polymers). In yet other embodiments, the MNPs are disrupted by altering a magnetic field applied to the MNP preparation. In yet other embodiments, the MNPs are disrupted thermally by applying heat, cooling or freezing. In more preferred embodiments, the MNPs are disrupted by a combination of the above-referenced techniques.

The machines of the invention comprise a BNC mixer. Persons of skill in the art would recognize that mixing may be accomplished in a variety of ways. In preferred embodiments, the BNC mixer comprises a mixing tee into which the enzyme and MNC preparations are fed and mixed. Alternatively, the mixing may be accomplished in a chamber where the BNCs are formed by increasing the perturbation of the flowing solutions to be mixed. In other embodiments, the BNC mixer comprises a mixing tee (T-shape tubing connector). In other embodiments, the BNC mixer is a tubing with inner ridges or pillars that increase perturbations.

In some embodiments, the machines of the invention further comprise a scaffolding assembly device for templating or concentrating the BNCs onto or into a level 2 scaffolding material. In preferred embodiments, the scaffolding is magnetic. The level 2 structures may be random or ordered. In other preferred embodiments, the machine contains a scaffolding container for mixing a scaffolding preparation with the BNCs to produce a level 2 assembly functionalized with BNCs. In yet other preferred embodiments, the scaffolding and BNCs are mixed mechanically or magnetically. In more preferred embodiments, the BNC's are placed immediately into a scaffolding to discourage the BNCs from over-aggregating and to promote homogenous immobilized enzyme structure formation.

Figure 2:
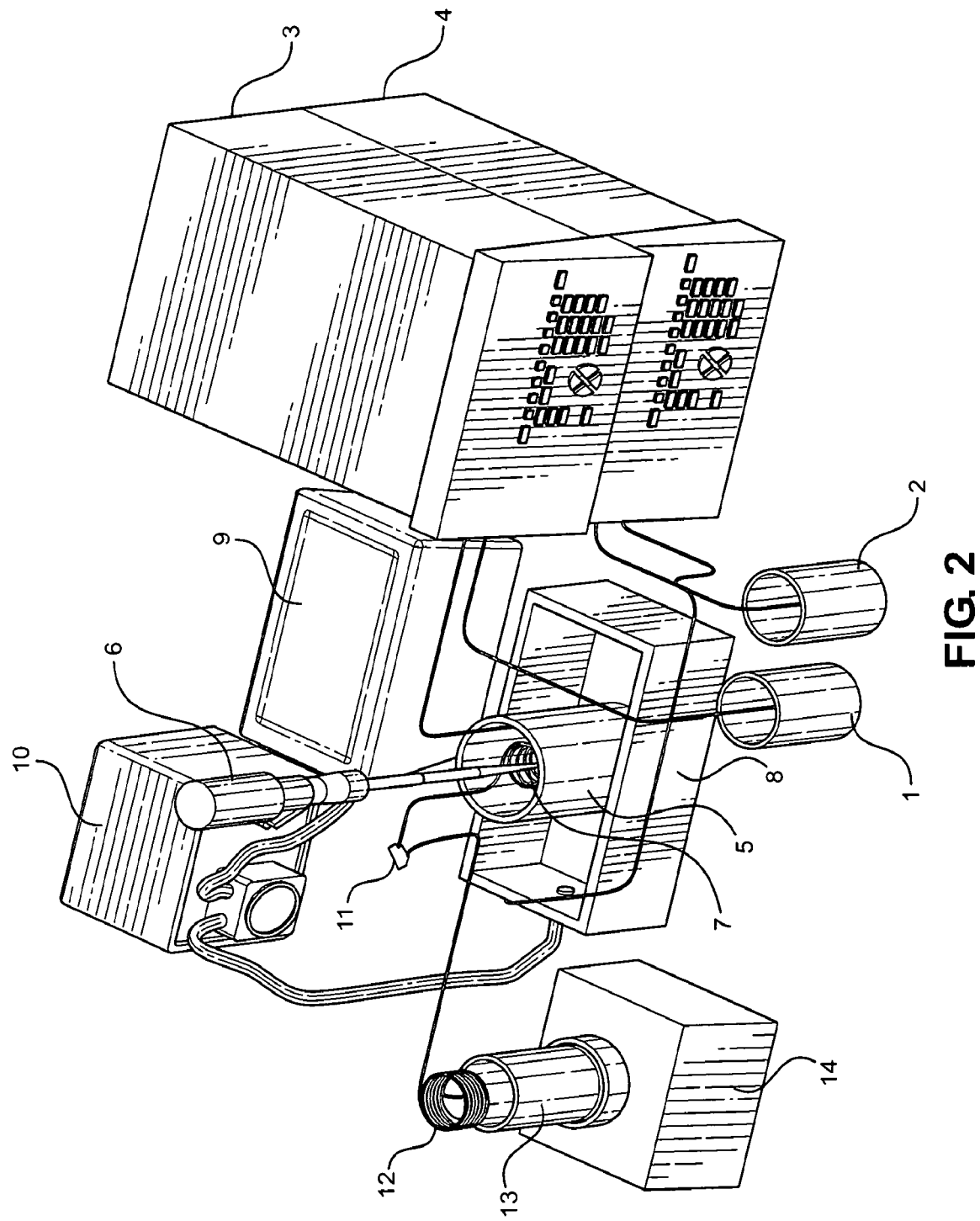
FIG. 2: A pictorial diagram of an exemplary machine for the automated production of BNCs

FIG. 2 provides an exemplary machine for producing BNCs. Enzymes are held in a container (1) and MNPs in another container (2). A pump (4) sends the MNPs to a sonication coil (7) comprised of tubing wrapped around the horn of a sonicator (6). The sonication coil is held within a stainless steel container (5) that ricochets the sonication forces around the coil (7). In other embodiments, the sonication coil is immersed in a sonication bath. In yet other embodiments, the sonication is performed in an online-fashion with an online sonicator.

The container (5) is held within a cooling water bath (8). Cool water is sent to the bath by a pump (10) that sends water from a cooling system (9). Sonicated MNPs are then pumped to a mixing tee (11) into which enzymes are sent using a pump (3). The enzymes and MNPs are mixed in a mixing coil (12) where BNCs are made. The BNCs are then sent to a shaker (14) into which magnetic scaffolding has been sent from a magnetic scaffold container (13) to produce BNCs in a level 2 assembly for catalytic use.

In some embodiments, in order to sufficiently break down the nanoparticles, the sonication time is calculated and controlled by the length and diameter of the tubing in the coil (7) as well as the pump (4) flow rate. The calculation is as follows:

$$L_S = \frac{T_S * F_A}{\pi * (D_A/2)^2}$$

where
$L_S$=length of sonication coil (m)
$T_S$=sonication time (min)
$F_A$=flow rate of MNP pump (ml/min)
$D_A$=MNP pump tubing inner diameter (mm)

In some embodiments, nanoparticles that were already subjected to sonication are sent to the mixing coil (12). In other embodiments, the tubes are kept at an adequate distance away from the sonicator to prevent unintentional sonication and denaturation of the enzymes.

In some embodiments, the enzyme and MNP tubes are connected using a mixing tee connection with a mixing loop. The amount of mixing time required is calculated as follows:

$$L_M = \frac{T_M * (F_A + F_B)}{\pi * (D_0/2)^2}$$

where
$L_M$=length of mixing tube (m)
$T_M$=mixing time (min)
$F_B$=flow rate of enzyme pump (ml/min)
$D_O$=output tubing inner diameter (mm)

In some embodiments, the tubes connected to the splitter are coiled to preserve space. In other embodiments, a splitter drops the MNP/enzyme mixture into the shaker (14) with magnetic scaffolds. The splitter allows the mix to fall over a larger surface area than just a single tube. The container is shaken to ensure that the BNCs are mixing thoroughly with the scaffolds.

In order that the invention described herein may be more fully understood, the following examples are set forth. It should be understood that these examples are for illustrative purposes only and are not to be construed as limiting this invention in any manner.

EXAMPLES

Example 1

Optimizing the Ratio of Enzymes with Iron Oxide Magnetic Nanoparticles

Enzyme loading is optimized for each enzyme by optimizing the ratio of enzyme to-MNPs at different pH values. The loading of enzymes immobilized into iron oxide magnetic nanoparticle clusters is determined, for example, indirectly utilizing a modified Bradford Protein Quantification assay to measure unbound enzymes.

A fixed concentration of superparamagnetic iron nanoparticles (500 µg/mL), adjusted to a pH of about 4 to 11 is combined with enzymes at concentrations of about 5-1000 µg/mL). After 1 to 12 h of contact time, the enzyme/nanoparticle clusters (Level 1) are immobilized on excess magnetite microparticles (20 g microparticles/1 g MNP) (Level 2) in suspension. The immobilized enzyme is separated from suspension by pelleting with a permanent magnet. Unbound protein that remains in the supernatant can be quantified with the Bradford Assay in microplates using a microplate UV/visible spectrophotometer by reading absorbance at 595 nm and a using standard curve. Coomassie Brilliant Blue G-250 dye in Bradford Reagent binds to basic amino acid residues to form a stable complex with UV absorbance at 595 nm (blue). This absorbance follows Beer's Law. By using a standard curve of protein concentration vs. $A_{595}$, the protein concentration in solution is determined. The amount of immobilized protein is calculated from the difference between total protein and unbound protein:

[E]Bound=[E]Total−[E]Unbound

[E]=enzyme concentration (µg/mL)

A binding isotherm is generated from the plot of $[E]_{Bound}$ vs. $[E]_{Total}$ and fit quadratic from of the Langmuir adsorption model. Enzyme loading capacity for level 1 immobilization is expressed as a percentage in terms of grams of protein bound per grams of nanoparticles. For example:

1% loading=(1 g bound protein)/(100 g nanoparticles)

After the optimal ratio of enzyme to nanoparticle is determined, the minimum contact-time for 100% capture of enzymes is determined with an immobilization kinetic curve (10 min, 1 hour, 5 hour and 18 hours). The enzyme immobilization procedure is as follows:

For quantification, standards are prepared comprising 2 mL dilutions of stock enzyme with MilliQ water: 0, 10, 50, 100, 250, 500, 750, 1000, 2000 µg/mL. Prepare 3 tubes of 5 mL 1000 µg/mL nanoparticles (MNP). Use 1 M HCl and 1 M NaOH to adjust the pH of MNP for one tube each of pH4, 5, 9, and 11. Sonicate MNP for 1 min at 20% amplitude.

Enzymes are immobilized as follows: Aliquot 500 µL of sonicated MNP into 9 microfuge tubes. Do this for each pH of MNP for a total of 27 tubes. Mix 500 µL of each enzyme dilution into MNP aliquots of each pH to create a total of 27 samples, 9 of each pH MNP with final protein concentrations 0, 5, 25, 50, 125, 250, 375, 500, and 1000 µg/mL and a final MNP concentration of 500 µg/mL. Vortex each sample, then agitate in a tumbler for 12 h at 4° C. to allow contact-time between enzyme and MNP.

Prepare 5 mL of 20 mg/mL magnetite microparticle suspension; 100 mg magnetite into 5 mL MilliQ water. Mix magnetite suspension by shaking vigorously. Disperse the microparticles by pipetting up and down 10 times. Add 500 µL of 20 mg/mL microparticle suspension to each of the 27 enzyme samples. Mix sample for 10 min using an orbital shaker to mount level 1 immobilized enzyme onto level 2 scaffold. Pellet the level 2 with a permanent rare earth magnet. Collect supernatant and dilute as necessary so maximum concentration (i.e. 0% loading) falls within 5-20 µg/mL range.

Perform Bradford Assay on diluted supernatants to determine the concentrations of diluted supernatants. Scale these concentrations by their appropriate dilution factors to find the concentration of unbound protein remaining after level 1 immobilization. Calculate bound protein from the difference between initial total protein and unbound protein:

[$E$]Bound=[$E$]Total−[$E$]Unbound

[$E$]=enzyme concentration (µg/mL)

The quantification of immobilization efficiency is calculated by plotting [E]$_{Bound}$/500 µg/mL MNP vs. [E]$_{Total}$/500 µg/mL. Modeling software is used to fit the Total, data to a Langmuir adsorption model. After optimization of the enzyme to MNPs, a satisfactory enzyme loading is 1-100% (g of enzyme per 100 g of material).

Example 2

Optimizing Enzyme Immobilization Time with Iron Oxide Magnetic Nanoparticles

Maximal Enzyme loading is first optimized for each enzyme for a fixed amount of MNPs and is determined as above in Example 1. After the optimal ratio of enzyme to nanoparticles is determined, the minimum contact-time for 100% capture of enzymes is determined with an immobilization kinetic curve (0 minutes, 5 minutes, 1 hour, 5 hours and 18 hours).

The enzyme immobilization procedure is as follows: From the binding isotherm, select the highest enzyme loading that results in 100% capture of enzyme ([E]$_{max}$). Prepare 6 mL of 1000 µg/mL MNP at the pH of selected enzyme loading conditions. Sonicate the MNP for 1 min at 20% amplitude. Make ten 500 µL aliquots of sonicated MNP in 1.5 mL tubes.

Prepare 6 mL of 2*[E]$_{max}$. Prepare 6 mL 20 mg/mL level 2 in MilliQ water. Add 500 µL of enzyme to eight of the MNP aliquots, resulting in a final enzyme concentration of [E]$_{max}$ and MNP concentration of 500 µg/mL.

At the following time points, add 500 µL of well mixed level 2 to an enzyme immobilizing aliquot to end the immobilization: 1 min, 5 min, 15 min, 30 min, 60 min, 90 min, 120 min, and 18 h (overnights). Follow the Bradford assay procedure above to determine the concentration of enzyme still in solution after a given time, using 1:1 MilliQ water and Bradford Reagent as a blank. The earliest time for 100% immobilization of the enzyme is when there is no enzyme in the supernatant.

The enzyme is immobilized within about 5 to 30 minutes at maximal loading capacity (g of enzyme per 100 g of material).

Example 3

Immobilization of an EC 1. Enzyme: Lipoxidase

Lipoxidase are oxidoreductases (EC 1.13.11.12) that catalyze the incorporation of molecular oxygen into fatty acids. Lipoxidase from the soybean strain *Glycine max* (LPO) has a high activity as measured by the conversion of ammonium linoleate into a mix of four regioisomeric hydroperoxyoctadecadienoic acids (HPODE), which are linoleic hyperoxides:13-(Z,E)-, 9-(E,Z)-, 13-(E,E)-, 9-(E,E)-HPODE. Each of these has a peak UV absorbance at 234 nm with an extinction coefficient (c) of 25,000 $M^{-1}cm^{-1}$. By reading the increase in absorbance at 234 nm, the conversion of ammonium linoleate to its hydroperoxides can be evaluated. See, Anthon et al., *J. Agri. Food Chem.* 49:32-37 (2001); Villaverde et al. *Industrial Crops and Products* 34(3):1474-1481 (2011). Villaverde et al., *Chemical Engineering Journal* 217:82-90 (2013). The foregoing are incorporated by reference herein in their entirety.

In one embodiment, lipoxidase immobilization is optimized and the resulting biocatalytic activity is measured with end-point kinetics as follows. The binding isotherm determines the basic conditions for the immobilization of LPO with MNP: optimal pH, minimum nanoparticle:enzyme ratio for complete immobilization, and minimum contact time for complete immobilization. Through the screening of nanoparticle concentrations for immobilizing LPO, the conversion of linoleic acid to HPODE is demonstrated by immobilized LPO and the best concentration of nanoparticles for immobilization. This immobilized LPO is optimized to equal or exceed the activity of free enzyme at 18 h conversion—an industrially relevant time scale—and with comparable V$_{max}$ as well.

The peak loading of LPO on superparamagnetic iron nanoparticles (NP) is determined as described above. Using the peak loading as a baseline for minimum nanoparticle concentration, pH, and contact time, immobilized LPO is screened for best LPO-to-NP ratio in terms of activity. Level 2 immobilized LPO activity is measured using the conversion of linoleate to its hydroperoxides (HPODE) by reading the increase in absorbance at 234 nm. Linoleate and dissolved oxygen are combined with level 2 immobilized LPO in 1 mL batch reactions. The reaction rate is determined by measuring the concentration of HPODE in a kinetic time course (1 min-18 h). Over only a short time, the hydroperoxides begins to oxidize. The optimized immobilized LPO is compared to free LPO for 18 h total conversion of substrate. After selecting the best conditions for immobilization, level 2 immobilized LPO is tested for reusability.

The binding isotherm for lipoxidase is determined as described in Examples 1-2 above. Determine the non-immobilized LPO Concentration ([E]$_{60\%}$) required for 60% conversion at 18 hours: Prepare a 30 mM linoleic acid stock solution in 1% Tween® 20 and 100 mM phosphate buffer pH 7. Always dilute with 100 mM phosphate buffer pH 7. For each of the following LPO concentrations, 250 µL will be dispensed into two 1.5 mL microfuge tube each: 4, 20, 40, 200, 400, 500, 1000, or 5000 nM as necessary. Dilute enzyme with MilliQ water. In one tube for each enzyme concentration above, substrates and buffer are combined in the following proportions:

TABLE 1

Reaction Mix for [E]60% Determination Assay

| Reagents | [Stock] | [Assay] | Volume |
|---|---|---|---|
| LPO | 4, 20, 40, 200, or 400 nM | 1, 5, 10, 50, 100 nM | 250 µL |
| Linoleic acid in 1% Tween ® 20 and Phosphate | 2.4 mM in 100 mM phosphate buffer | 0.6 mM in 100 mM phosphate buffer | 250 µL |

TABLE 1-continued

Reaction Mix for [E]60% Determination Assay

| Reagents | [Stock] | [Assay] | Volume |
|---|---|---|---|
| buffer pH 7 | | | |
| Phosphate buffer pH 7 | 200 mM | 100 nM | 500 µL |

*Blanks will be prepared using the other enzyme tubes with phosphate buffer and remaining substrate volume replaced by 250 µL MilliQ water.

The reaction and blank tubes will be sealed with Parafilm and agitated at room temperature in the dark using an orbital shaker. After 18 h of contact time, Centrifuge all reaction and enzyme blank tubes for 10 min at 12000 g. In triplicate, read the A234 of 250 µL from reaction sample and blank with enzyme blanks in microplates using a Bio-Tek Epoch plate reader. Use the extinction coefficient for HPODE at 234 nm to calculate the concentration of HPODE in the supernatant. Determine the lowest enzyme concentration required to complete the reaction to 60% conversion for screening immobilized LPO ($[E]_{60\%}$).

Immobilization of LPO for an MNP concentration screening assay is performed as follows: Using the optimized conditions for immobilization found with the ZYM Binding Isotherm Protocol, prepare 3 mL level 2 immobilized LPO with 20 g level 2 scaffold/1 g MNP. Also immobilize LPO using 5× and 10×MNP, all other conditions kept constant. Shake vigorously to mix before use. Prepare free enzyme to the same concentration as well. Prepare 3 mL of dilute level 2 immobilized LPO and free LPO to the concentration $4[E]_{60\%}$, which is equivalent to 4*(minimum concentration of LPO to convert 60% linoleic acid into HPODE in 18 h. For each concentration of MNP for LPO immobilization (1×, 5×, 10×) as well as free LPO, dispense 9×250 µL aliquots of well-mixed immobilized LPO for a total of 36 samples.

Kinetic Time Course: Label tubes for each MNP concentration blank, 1 min, 5 min, 15 min, 30 min, 60 min, 90 min, 120 min, and 10800 min (18 hours), where Ø is a protein and buffer blank, and mark them "1×", "5×", "10×", or "free" as appropriate. Prepare 12 mL 2.4 mM linoleic acid in 100 mM phosphate buffer pH 7 and 24 mL 200 mM phosphate buffer pH 8. Start the reactions by pipetting the 750 µL of Reaction Mix into each tube labeled 1 min-10800 min. This brings the enzyme concentration to $[E]_{60\%}$.

TABLE 2

Reaction Mix for Screening Assay

| Reagent | [Stock] | [Assay] | Volume |
|---|---|---|---|
| Linoleic acid in 1% Tween® 20 and Phosphate buffer pH 7 | 2.4 mM in 100 mM phosphate buffer | 0.6 mM in 100 mM phosphate buffer | 10 µL |
| Phosphate buffer pH 7 | 200 mM | 100 mM | 20 µL |

Seal tubes with Parafilm and agitate in an orbital shaker in the dark at room temperature. Fill each blank with 250 µL 200 mM phosphate buffer pH 8 and 500 µL MilliQ water for a final LPO and phosphate buffer concentrations of $[E]_{60\%}$ and 50 mM respectively. Stop at each of 1 min, 5 min, 15 min, 30 min, 60 min, 90 min, 120 min, and 18 Hours. Pellet one sample of immobilized enzyme for 1×, 5×, and 10× each using a permanent rare-earth magnet. In triplicate, read the A234 of 250 µL from each sample immediately after pelleting immobilized LPO, and blank readings with diluted enzyme blanks. Calculate the HPODE concentrations in reaction tubes using the extinction coefficient for 234 nm.

An optimized immobilized LPO is selected by plotting the amount of linoleic acid converted to HPODE against time and determining the Vmax's from the slopes of the kinetic graphs in the linear region.

The reusability of the magnetically-immobilized LPO is determined as follows: Select the 18 hour-immobilized LPO sample that has the highest Vmax (and which should also be able to complete the reaction by 18 h) as well as its blank. Pellet the immobilized LPO with a permanent rare-earth magnet. Remove the supernatant.

A kinetic time course is determined as follows: Prepare 300 µL of 2.4 mM linoleic acid in 100 mM phosphate buffer pH 7 and 600 µL 200 mM phosphate buffer pH 7. Start the reaction by pipetting the 750 µL of Reaction Mix into the reaction tube. This brings the enzyme concentration to $[E]_{60\%}$

TABLE 3

Reaction Mix for Recycling Assay

| Reagent | [Stock] | [Assay] | Volume |
|---|---|---|---|
| Linoleic acid in 1% Tween® 20 and Phosphate buffer pH 7 | 2.4 mM in 100 mM phosphate buffer | 0.6 mM in 100 mM phosphate buffer | 300 µL |
| Phosphate buffer pH 7 | 200 mM | 100 mM | 600 µL |

Seal tubes with Parafilm and agitate in an orbital shaker in the dark at room temperature. Fill the blank with 250 µL 200 mM phosphate buffer pH 8 and 500 µL MilliQ water for a final LPO and phosphate buffer concentrations of $[E]_{60\%}$ and 50 mM respectively. Determine the amount of linoleic acid converted to HPODE during this immobilized LPO recycling test.

Example 4

Immobilization of an EC 3. Enzyme—Nitrilase

Nitrilase (NIT) activity is measured by the conversion of mandelonitirile into a (R)-mandelic acid. The formation of mandelic acid results in a drop in pH. It is monitored spectrophotometrically with dyes such as bromothymol blue (BB) in microplates using a plate reader as a decrease in $A_{616}$ with the extinction coefficient 15703.79 $M^{-1}cm^{-1}$ (Banerjee et al., *J. Biomolecular Screening* 8(5):559-65 (2003)).

The peak loading of NIT on superparamagnetic iron nanoparticles (NP) is determined using a binding isotherm protocol. Using the peak loading as a baseline for minimum nanoparticle concentration, pH, and contact time. Immobilized NIT activity is screened for the best NIT-to-NP ratio. Level 2 immobilized NIT conversion of mandelonitrile to mandelic acid is measured using the change in color of a bromothymol blue from blue to yellow by reading the decrease in absorbance at 616 nm. Mandelonitrile and bromothymol blue are combined with level 2 immobilized NIT in 1 mL batch reactions. The reaction rate will be determined by measuring the pH change of the solution colorimetrically in a kinetic time course (1 min-18 h). The concentration of nitrilase required to achieve complete conversion of substrate in 18 h will be determined.

The immobilized NIT is then optimized to equal or exceed the activity of the free NIT at 18 h for total conversion of substrate. After selecting the best conditions for immobilization, level 2 immobilized NIT is tested for reusability in successive assays. A binding isotherm is then determined using the methods described in Examples 1 and 2.

In one embodiment, the immobilization of a nitrilase is optimized and the resulting biocatalytic activity is measured with end-point kinetics using a colorimetric assay. First, the free NIT concentration (reference) necessary for full conversion of the substrate in 18 hours ($[E]_{18h}$) is determined as follows:

Prepare 12 mL 50 mM mandelonitrile stock solution in 10% ethanol and MilliQ water, 12 mL 0.04% BB in MilliQ water, and 12 mL 40 mM phosphate buffer pH 7.2. For each of the following NIT concentrations, 250 μL is dispensed into two 1.5 mL microfuge tube each: 4, 20, 40, 200, 400, 500, 1000, 5000 nM as necessary. Dilute enzyme with MilliQ water. In one tube for each enzyme concentration above, substrates and buffer are combined in the following proportions:

TABLE 4

Reaction Mix for $[E]_{18h}$ Determination Assay

| Reagents | [Stock] | [Assay] | Volume |
|---|---|---|---|
| NIT | 4, 20, 40, 200, or 400 nM | 1, 5, 10, 50, 100 nM | 250 μL |
| Mandelonitrile | 50 mM in 10% ethanol | 12.5 mM in 2.5% ethanol | 250 μL |
| Phosphate buffer pH 7.2 | 40 mM | 10 mM | 250 μL |
| Bromothymol Blue | 0.04% | 0.01% | 250 μL |

*Blanks are prepared using the other enzyme tubes with phosphate buffer and remaining substrate volume replaced by 250 μL MilliQ water.

The reaction and blank tubes will be sealed with Parafilm and agitated at room temperature in the dark using an orbital shaker. After 18 h of contact time, centrifuge all reaction and enzyme blank tubes for 10 min at 12000 g. In triplicate, read the A616 from reaction sample and blank with enzyme blanks in microplates using a Bio-Tek® Epoch plate reader.

Make a standard curve of mandelic acid with a dilution series starting with 12.5 mM mandelic acid in 2.5% ethanol, 10 mM phosphate buffer pH 7.2, and 0.01% bromothymol blue. Dilute using 10 mM phosphate buffer pH 7.2 and 0.01% BB. Calculate the concentration of mandelic acid formed using the standard curve. If all concentrations of enzyme complete the reaction to 100% conversion, select the lowest concentration of enzyme as the one used for screening immobilized NIT ($[E]_{18h}$).

Second, the NIT is immobilized into BNCs and the immobilization is optimized using a standard Optimization Assay: Using the optimized conditions for immobilization found with the isotherm protocol in Example 1, prepare 3 mL level 2 immobilized NIT with 20 g level 2 scaffold/1 g MNP. Also immobilize NIT using 5× and 10×MNP, all other conditions kept constant. Shake vigorously to mix before use. Prepare free enzyme to the same concentration as well. Prepare 3 mL of dilute level 2 immobilized NIT and free NIT to the concentration 4*$[E]_{18h}$, which is equivalent to 4*(minimum concentration of NIT to convert 100% mandelonitirile into mandelic acid in 18 h). For each concentration of MNP for NIT immobilization (1×, 5×, 10×) as well as free NIT, dispense 9×250 μL aliquots of well-mixed immobilized NIT for a total of 36 samples.

Kinetic Time Course: Label tubes for each MNP concentration blank, 1 min, 5 min, 15 min, 30 min, 60 min, 90 min, 120 min, and 10800 min (18 hours), where the blank is a protein and buffer blank, and mark them "1×", "5×", "10×", or "free" as appropriate. Prepare 12 mL 50 mM mandelonitrile stock solution in 10% ethanol and MilliQ water, 12 mL 0.04% BB in MilliQ water, and 12 mL 40 mM phosphate buffer pH 7.2. Start the reactions by pipetting the 750 μL of Reaction Mix into each tube labeled 1 min-10800 min. This brings the enzyme concentration to $[E]_{18h}$.

TABLE 5

Reaction Mix for Screening Assay

| Reagent | [Stock] | [Assay] | Volume |
|---|---|---|---|
| Mandelonitrile | 50 mM in 10% ethanol | 12.5 mM in 2.5% ethanol | 10 mL |
| Phosphate buffer pH 7.2 | 40 mM | 10 mM | 10 mL |
| Bromothymol Blue | 0.04% | 0.01% | 10 mL |

Seal tubes with Parafilm and agitate in an orbital shaker in the dark at room temperature. Fill each blank with 250 μL 40 mM phosphate buffer pH 7.2, 250 μL 0.01% BB, and 250 μL MilliQ water for a final NIT concentration of $[E]_{18h}$. Stop at each of 1 min, 5 min, 15 min, 30 min, 60 min, 90 min, 120 min, and 18 hours. Pellet 1 sample of immobilized enzyme for 1×, 5×, and 10× each, using a permanent rare-earth magnet. In triplicate, read $A_{616}$ of 250 μL from each sample immediately after pelleting immobilized NIT, and blank readings with diluted enzyme blanks. Create a standard curve of mandelic acid with a dilution series starting with 12.5 mM mandelic acid in 2.5% ethanol, 10 mM phosphate buffer pH 7.2, and 0.01% bromothymol blue. Dilute using 10 mM phosphate buffer pH 7.2 and 0.01% BB. Calculate the concentration of mandelic acid formed using the standard curve.

Optimized immobilized NIT is selected by plotting the amount of mandelonitrile converted to mandelic acid against time and determining the $V_{max}$ from the slope of the kinetic graph in the linear region. The reusability is assayed for multiple cycles: Select the 18 hour immobilized NIT sample that has the highest Vmax (and which may also be able to complete the reaction by 18 h) as well as its blank. Pellet the immobilized NIT with a permanent rare-earth magnet. Remove the supernatant.

Kinetic Time Course: Prepare 300 μL each of 50 mM mandelonitirile in 10% ethanol, 40 mM phosphate buffer pH 7.2, and 0.04% BB. Start the reaction by pipetting the 750 μL of Reaction Mix into the reaction tube. This brings the enzyme concentration to $[E]_{18h}$.

TABLE 6

Reaction Mix for Recycling Assay

| Reagent | [Stock] | [Assay] | Volume |
|---|---|---|---|
| Mandelonitrile | 50 mM in 10% ethanol | 12.5 mM in 2.5% ethanol | 300 μL |
| Phosphate buffer pH 7.2 | 40 mM | 10 mM | 300 μL |
| Bromothymol Blue | 0.04% | 0.01% | 300 μL |

Seal tubes with Parafilm and agitate in an orbital shaker in the dark at room temperature. Fill the blank with 250 μL 40 mM phosphate buffer pH 7.2, 250 μL 0.01% BB and 2504 μL MilliQ water for a final NIT concentration of $[E]_{18h}$. The recycling is demonstrated by repeating the protocol and recovering the material and using it for subsequent cycles.

The binding isotherm is used to determine the basic conditions for the immobilization of NIT with MNP: optimal pH, minimum nanoparticle:enzyme ratio, and minimum contact time for complete immobilization. Through the screening of nanoparticle concentrations for immobilizing NIT, the conversion of mandelonitrile to mandelic acid is demonstrated by immobilized NIT. The best concentration of nanoparticles for immobilization is thus determined. Optimized NIT may at least match free enzyme for 18 hour conversions at industrially relevant time scales and $V_{max}$. The optimized NIT is used again to determine the reusability of immobilized NIT without loss for 18 hours of activity over 5 cycles.

Example 5

Immobilization of a Cytochrome Oxidase (EC 1.9.3.1)

Cytochrome c oxidases ("CCO", EC 1.9.3.1) that participate in the electron transport chain in aerobic metabolism of animals, plants, yeast, and some bacteria. Errede et al., *PNAS* 73(1):113-117 (1976). It's activity is measured by the oxidation of ferrocytrochrome c to ferricytochrome c. (See, e.g. Cytochrome c Oxidase Assay Kit, Sigma-Aldrich 2014: 1-4.) The foregoing are incorporated by reference herein in their entirety. The formation of ferricytochrome c is monitored spectrophotometrically as the decrease in absorbance at 550 nm. The difference in ferrocytochrome's and ferricytochrome's extinction coefficients is 21.85 $mM^{-1}cm^{-1}$.

The maximal loading of CCO on superparamagnetic iron nanoparticles (NP) is determined using a binding isotherm protocol. Using the peak loading as a baseline for minimum nanoparticle concentration, pH, and contact time, immobilized CCOactivity is screened for the best CCO-to-NP ratio. Level 2 immobilized CCO oxidation of ferrocytrochrome c to ferricytochrome c is evaluated using the change in absorbance at 550 nm measured in a microplate using the Bio-Tek® Epoch plate reader. Cytochrome c is reduced by dithiothreitol (DTT) and is re-oxidized by level 2 immobilized CCO in 1 mL batch reactions. The reaction rate is measured by the decrease in $A_{550}$ in a kinetic time course (1 min-18 h).

In one embodiment, the optimization of CCO immobilization into BNCs and the subsequent measurement of its activity is performed with end-point kinetics using a colorimetric assay as follows: The immobilized CCO is optimized to equal or exceed the activity of free CCO for 18 hours of total conversion of substrate. After selecting the best conditions for immobilization, level 2 immobilized CCO is tested for reusability with five successive 18 hour reactions in 1 mL assays. The binding isotherm for CCO is determined as described above in Example 1.

The free CCO concentration (reference) required to fully convert the substrate at 18 hours ($[E]_{18h}$) is determined as follows: Prepare 12 mL 40 µM cytochrome c stock solution with 92 µM DTT and MilliQ water, and 24 mL 20 mM Tris-HCl pH 7 with 240 mM KCl. Allow the Cytrochrome c 20 minutes to be reduced by DTT, confirmed by an A550/A565 between 10 and 20. For each of the following CCO concentrations, 250 µL will be dispensed into two 1.5 mL microfuge tubes each: 4, 20, 40, 200, 400, 500, 1000, and 5000 nM as necessary. Dilute enzyme with MilliQ water. In one tube for each enzyme concentration above, substrates and buffer are combined in the following proportions:

TABLE 7

Reaction Mix for [E]18 h Determination Assay

| Reagents | [Stock] | [Assay] | Volume |
|---|---|---|---|
| CCO | 4, 20, 40, 200, or 400 nM | 1, 5, 10, 50, 100 nM | 250 µL |
| Cytochrome c with DTT | 40 µM in 92 µM DTT | 10 µM in 23 µM DTT | 250 µL |
| Tris-HCl pH 7 with KCl | 20 mM with 240 mM KCl | 10 mM with 120 mM KCl | 500 µL |

*Blanks will be prepared using the other enzyme tubes with phosphate buffer and remaining substrate volume replaced by 250 µL MilliQ water.

The reaction and blank tubes are sealed with Parafilm and agitated at room temperature in the dark using an orbital shaker. After 18 h of contact time, Centrifuge all reaction and enzyme blank tubes for 10 min at 12000 g. In triplicate, read the $A_{550}$ from reaction sample and blank with enzyme blanks in microplates using a Bio-Tek® Epoch plate reader. Create a standard curve of oxidized cytochrome c with a dilution series starting with 10 µM oxidized cytochrome c (let sit in room temp overnight) without DTT and 10 mM Tris-HCl pH 7 with 120 mM KCl. Dilute using 10 mM Tris-HCl pH 7 with 120 mM KCl. Calculate the concentration of Cytochrome C oxidized using the standard curve. If all concentrations of enzyme complete the reaction to 100% conversion, select the lowest concentration of enzyme as the one used for screening immobilized CCO ($[E]_{18h}$.

Immobilization of CCO for MNP Concentration Screening Assay: Using the optimized conditions for immobilization described in Example 1, prepare 3 mL level 2 immobilized CCO with 20 g level 2 scaffold/1 g MNP. Also immobilize CCO using 5× and 10×MNP, all other conditions are kept constant. Shake vigorously to mix before use. Prepare free enzyme to the same concentration as well. Prepare 3 mL of dilute level 2 immobilized CCO and free CCO to the concentration 4*$[E]_{18h}$, which is equivalent to 4*(minimum concentration of CCO to oxidize 100% cytochrome c in 18 h). For each concentration of MNP for CCO immobilization (1×, 5×, 10×) as well as free CCO, dispense 9×250 µL aliquots of well-mixed immobilized CCO for a total of 36 samples.

Kinetic Time Course: Label tubes for each MNP concentration blank, 1 min, 5 min, 15 min, 30 min, 60 min, 90 min, 120 min, and 10800 min (18 hours), where the blank is a protein and buffer blank, and mark them "1×", "5×", "10×", or "free" as appropriate. Prepare 12 mL 40 µM cytochrome c stock solution with 92 µM DTT and MilliQ water, and 24 mL 20 mM Tris-HCl pH 7 with 240 mM KCl. Allow the cytochrome c 20 min to be reduced by DTT, confirmed by an A550/A565 between 10 and 20. Start the reactions by pipetting the 750 µL of Reaction Mix into each tube labeled 1 min-10800 min. This brings the enzyme concentration to $[E]_{18h}$.

TABLE 8

Reaction Mix for Screening Assay

| Reagent | [Stock] | [Assay] | Volume |
|---|---|---|---|
| Cytochrome c with DTT | 40 µM in 92 µM DTT | 10 µM in 23 µM DTT | 10 mL |
| Tris-HCl pH 7 with KCl | 20 mM with 240 mM KCl | 10 mM with 120 mM KCl | 20 mL |

Seal tubes with Parafilm and agitate in an orbital shaker in the dark at room temperature. Fill each blank with 500 µL 20 mM Tris-HCl pH 7 with 240 mM KCl and 250 μL MilliQ water for a final CCO concentration of $[E]_{18h}$. Stop at each of 1 min, 5 min, 15 min, 30 min, 60 min, 90 min, 120 min, and 18 hours. Pellet 1 sample of immobilized enzyme for 1×, 5×, and 10× each, using a permanent rare-earth magnet. In triplicate, read the A550 of 250 μL from each sample immediately after pelleting immobilized CCO, and blank readings with diluted enzyme blanks.

Create a standard curve of oxidized cytochrome c with a dilution series starting with 10 μM oxidized cytochrome c (let sit in room temp overnight) without DTT and 10 mM Tris-HCl pH 7 with 120 mM KCl. Dilute using 10 mM Tris-HCl pH 7 with 120 mM KCl. Calculate the concentration of cytochrome c oxidized using the standard curve.

Optimized immobilized CCO is determined by plotting the amount of cytochrome c oxidized over time. The $V_{max}$ is determined from the slopes of the kinetic graphs in the linear region.

Reusability is assayed over 5 cycles as follows: Select the 18 hour-immobilized CCO sample that has the highest Vmax (and which should also be able to complete the reaction by 18 h) as well as its blank. Pellet the immobilized CCO with a permanent rare-earth magnet. Remove the supernatant. A kinetic time course is calculated as follows: Prepare 300 μL 40 μM cytochrome c with 92 μM DTT and 600 μL 20 mM Tris-HCl pH 7 with 240 mM KCl. Start the reaction by pipetting the 750 μL of Reaction Mix into the reaction tube. This brings the enzyme concentration to $[E]_{18h}$.

TABLE 9

Reaction Mix for Recycling Assay

| Reagent | [Stock] | [Assay] | Volume |
|---|---|---|---|
| Cytochrome c with DTT | 40 μM in 92 μM DTT | 10 μM in 23 μM DTT | 300 μL |
| Tris-HCl pH 7 with KCl | 20 mM with 240 mM KCl | 10 mM with 120 mM KCl | 600 μL |

Seal tubes with Parafilm and agitate in an orbital shaker in the dark at room temperature. Fill each blank with 500 μL 20 mM Tris-HCl pH 7 with 240 mM KCl and 250 μL MilliQ water for a final CCO concentration of $[E]_{18h}$. The procedure is repeated multiple times to demonstrate reusability.

The binding determines the basic conditions for the immobilization of CCO with MNP: optimal pH, minimum nanoparticle:enzyme ratio, and minimum contact time for complete immobilization. Through the screening of nanoparticle concentrations for immobilizing CCO, the conversion of ferrocytochrome to ferricytochrome is demonstrated by immobilized CCO and the best concentration of nanoparticles for immobilization is determined. This optimized CCO may at least match free enzyme for 18 hour conversions for industrially relevant time scales and may have comparable $V_{max's}$. Once an optimized CCO is found, it is used again to demonstrate the reusability of immobilized CCO.

Example 6

Immobilization of Glucose Isomerase

Glucose isomerase (EC 5.3.1.5) catalyzes the isomerization of β-D-glucose to fructose with high stereo-selectivity. Adams et al. *Archives Biochem. Biophys.* 91:230-234 (1960); Wilson and Turner, Biosensors & Bioelectronics 7:165-185 (1992), both of which are incorporated by reference in their entirety. Its immobilization is optimized for a high activity when compared to free enzyme. Activity is measured by the conversion of glucose into fructose. The disappearance of glucose is monitored spectrophotometrically using a glucose oxidase/horseradish peroxidase system (GOX/HRP). GOX converts glucose and dissolved oxygen into hydrogen peroxide that is then use by HRP to oxidize phenol. The phenol radical then binds to 4-antiaminopyrene (4-AAP), a colorimetric agent. The increased absorbance at 550 nm due to the formation of a phenol-4-AAP complex directly corresponds to the amount of remaining glucose in solution. Therefore, a lower absorbance at 550 nm indicates that more glucose has been converted to fructose by glucose isomerase.

The peak loading of GI on superparamagnetic iron nanoparticles (NP) is determined using an isotherm protocol. Using the peak loading as a baseline for minimum nanoparticle concentration, pH, and contact time, immobilized GI activity is screened for the best GI-to-NP ratio. Level 2 immobilized GI conversion of glucose to fructose is evaluated using the change in absorbance at 550 nm measured in a microplate using the Bio-Tek® Epoch plate reader. Glucose and level 2 immobilized GI react in 1 mL batch reactions. After a reaction is allowed to occur for the desired duration, the reaction supernatant is diluted in a GOX/HRP mix as well phenol, buffer, and 4-AAP dye for a final 1 mL volume to quantify the remaining glucose. The reaction rate will be determined by measuring increased $A_{550}$ in a kinetic time course (1 min-18 h).

In one embodiment, immobilization of glucose isomerase is optimized and the subsequent activity is measured with end-point kinetics using a colorimetric assay as follows: The optimized immobilized GI matches free GI for 18 h total conversion of substrate. After selecting the best conditions for immobilization, level 2 immobilized GI will be tested for reusability with five successive 18 h reactions in 1 mL volumes.

The binding isotherm for GI is determined as described above.

Determine Free GI Concentration ($[E]_{18h}$) for 18 h 100% Reaction Completion: Prepare 12 mL 200 mM glucose stock solution, 24 mL 200 mM phosphate buffer (PB) pH 6, 12 mL 40 nM GOX with 40 nM HRP, and 12 mL 7 mM 4-AAP with 80 mM phenol. For each of the following GI concentrations, 250₄ will be dispensed into two 1.5 mL microfuge tube each: 4, 20, 40, 200, 400, 500, 1000, and 5000 nM as necessary. Dilute enzyme with MilliQ water. In one tube for each enzyme concentration above, substrates and buffer are combined in the following proportions:

TABLE 10

Reaction Mix for $[E]_{18\,h}$ Determination Assay

| Reagents | [Stock] | [Assay] | Volume |
|---|---|---|---|
| GI | 4, 20, 40, 200, or 400 nM | 1, 5, 10, 50, 100 nM | 250 μL |
| β-D-glucose | 200 mM | 50 mM | 250 μL |
| Phosphate buffer pH 6 | 200 mM | 50 mM | 250 μL |
| MilliQ water | | | 250 μL |

*Blanks are prepared using the other enzyme tubes with phosphate buffer and remaining substrate volume replaced by 250 μL MilliQ water.

The reaction and blank tubes are sealed with Parafilm and agitated at room temperature in the dark using an orbital shaker. After 18 h of contact time, centrifuge all reaction and enzyme blank tubes for 10 min at 12000 g. Dilute all samples and blanks in the Glucose Resolution Reaction Mix.

Immobilization of GI for MNP Concentration Screening Assay: Using the optimized conditions for immobilization found with the ZYM Binding Isotherm Protocol, prepare 3 mL level 2 immobilized GI with 20 g level 2 scaffold/1 g MNP. Also immobilize GI using 5× and 10×MNP, all other conditions kept constant. Shake vigorously to mix before use. Prepare free enzyme to the same concentration as well.

Prepare 3 mL of dilute level 2 immobilized GI and free GI to the concentration $4[E]_{18h}$, which is equivalent to 4*(minimum concentration of GI to convert 100% glucose into fructose in 18 h). For each concentration of MNP for GI immobilization (1×, 5×, 10×) as well as free GI, dispense 9×2504 aliquots of well-mixed immobilized GI for a total of 36 samples.

A kinetic time course is determined as follows: Label tubes for each MNP concentration blank, 1 min, 5 min, 15 min, 30 min, 60 min, 90 min, 120 min, and 10800 min (18 hours), where Ø is a protein and buffer blank, and mark them "1×", "5×", "10×", or "free" as appropriate. Prepare 12 mL 200 mM glucose stock solution, 24 mL 200 mM phosphate buffer (PB) pH 6, 12 mL 40 nM GOX with 40 nM HRP, and 12 mL 7 mM 4-AAP with 80 mM phenol.

Start the reactions by pipetting the 750 µL of Reaction Mix into each tube labeled 1 min-10800 min. This brings the enzyme concentration to $[E]_{18h}$.

TABLE 11

Reaction Mix for Screening Assay

| Reagents | [Stock] | [Assay] | Volume |
|---|---|---|---|
| β-D-glucose | 200 mM | 50 mM | 10 mL |
| Phosphate buffer pH 6 | 200 mM | 50 mM | 10 mL |
| MilliQ water | | | 10 mL |

Seal the tubes with Parafilm and agitate in an orbital shaker in the dark at room temperature. Fill each blank with 250 µL 200 mM PB pH 6, 250 µL 200 mM glucose, and 250 µL MilliQ water for a final GI concentration of $[E]_{18h}$. Stop at each of 1 min, 5 min, 15 min, 30 min, 60 min, 90 min, 120 min, and 18 hours. Pellet 1 sample of immobilized enzyme for 1×, 5×, and 10× each, using a permanent rare-earth magnet. Dilute each samples and blank in the Glucose Resolution Reaction Mix. Optimized immobilized GI is selected by plotting the amount of fructose against time and determining the $V_{max}$ from the slope of the kinetic graph in the linear region.

Reusability is assayed for 5 cycles: Select the 18 hour immobilized GI sample that has the highest $V_{max}$ (and which should also be able to complete the reaction by 18 hours) as well as its blank. Pellet the immobilized GI with a permanent rare-earth magnet. Remove the supernatant.

A kinetic time course is determined as follows: Prepare 300 µL 200 mM glucose stock solution, 600 µL 200 mM phosphate buffer (PB) pH 6, 300 µL 40 nM GOX with 40 nM HRP, and 300 µL 7 mM 4-AAP with 80 mM phenol. Start the reaction by pipetting the 750 µL of Reaction Mix into the reaction tube. This brings the enzyme concentration to $[E]_{18h}$.

TABLE 12

Reaction Mix for Recycling Assay

| Reagents | [Stock] | [Assay] | Volume |
|---|---|---|---|
| β-D-glucose | 200 mM | 50 mM | 300 µL |
| Phosphate buffer pH 6 | 200 mM | 50 mM | 300 µL |
| MilliQ water | | | 300 µL |

Seal tubes with Parafilm and agitate in an orbital shaker in the dark at room temperature. Fill each blank with 250 µL 200 mM PB pH 6, 250 µL 200 mM glucose, and 250 µL MilliQ water for a final GI concentration of $[E]_{18h}$. Dilute each samples and blank in the Glucose Resolution Reaction Mix.

The binding isotherm determines the basic conditions for the immobilization of GI with MNP: optimal pH, minimum nanoparticle:enzyme ratio, and minimum contact time for complete immobilization. Through the screening of nanoparticle concentrations for immobilizing GI, conversion of glucose into fructose is demonstrated by immobilized GI. The best concentration of nanoparticles for immobilization is determined.

In some embodiments, the magnetically immobilized GI is used in with a high substrate concentration at 55-60° C. and the pH is adjusted to 7.5-8.0 with sodium carbonate. Magnesium sulphate is added to maintain enzyme activity (since $Mg^{2+}$ is a cofactor). $Co^{2+}$ may also be used as a cofactor. This optimized GI may at least match free enzyme for 18 h conversions for industrially relevant time scales and may have comparable $V_{max's}$.

Example 7

Immobilization of a Transaminase

Omega-transaminases are transferases (EC 2.6.1.18) that catalyze the transfer of amine-groups to form chiral amines or ketones. An ω-transaminase, or amine-transaminase (ATA) is immobilized for high activity when comparared to free enzyme. It is measured by the transfer of an amine- from α-methyl benzylamine (MBA) to pyruvate to form acetophenone and alinine. Formation of acetophenone (AP) is read via increased UV absorbance at 245 nm. The extinction coefficient for AP is 12 $M^{-1}cm^{-1}$ (See Karim Engelmark Cassimjee Doctoral Thesis, KTH Royal Institute of Technology, School of Biotechnology, Stockholm (2012); Watson Neto, Ph.D. Thesis, Center for Process Engineering and Technology, Dept. of Chemical and Biochemical Engineering, Technical University of Denmark.) The foregoing are incorporated by reference herein in their entirety.

The peak loading of ATA on superparamagnetic iron nanoparticles (NP) is determined using the binding isotherm method described above. Using the peak loading as a baseline for minimum nanoparticle concentration, pH, and contact time, immobilized ATA is screened for best ATA-to-NP ratio in terms of enzyme activity. Level 2 immobilized ATA activity is evaluated using the conversion of MBA to acetophenone read by the increase in absorbance at 245 nm. MBA and co-substrate pyruvate are combined with level 2 ATA in 1 mL batch reactions. The reaction rate is determined by measuring the concentration of acetophenone in a kinetic time course (1 min-18 h).

In one embodiment, immobilization of ATA is optimized and the subsequent activity is measured with end-point kinetics using a colorimetric assay as follows: The immobilized ATA is optimized for the greatest $V_{max}$ and to match the activity of free ATA for an 18 h total conversion of substrate. After selecting the best conditions for immobilization, level 2 immobilized ATA is tested for reusability.

Immobilization of ATA for MNP Concentration Screening Assay: Using the optimized conditions for immobilization shown in Example 1, prepare 3 mL of level 2 immobilized ATA with 20 g level 2 scaffold/1 g MNP. Also immobilize ATA using 5× and 10×MNP, all other conditions kept constant. Shake vigorously to mix before use. Prepare free enzyme to the same concentration as well.

Prepare 3 mL of dilute level 2 immobilized ATA and free ATA to the concentration $[E]_{18h}$, which is equivalent to 4 times the minimum ATA concentration required to convert 100% MBA to AP in 18 h. For each concentration of MNP for ATA immobilization (1×, 5×, 10×) as well as free ATA, dispense 9×250 µL aliquots of well-mixed immobilized ATA for a total of 36 samples.

A Kinetic Time Course is determined as follows: Label tubes for each MNP concentration blank, 1 min, 5 min, 15 min, 30 min, 60 min, 90 min, 120 min, and 18 hours, where the blank is a protein and buffer blank, and mark them "1×", "5×", "10×", or "free" as appropriate. Prepare 4 mL 6 M HCl. Prepare 12 mL each of 10 mM MBA in 1% DMSO, 10 mM sodium pyruvate, and 200 mM phosphate buffer pH 8. Start the reactions by pipetting the 750४ of Reaction Mix into each tube. This brings the enzyme concentration to $[E]_{18h}$.

TABLE 13

Reaction Mix for Screening Assay

| Reagent | [Stock] | [Assay] | Volume |
| --- | --- | --- | --- |
| MBA | 10 mM in 1% DMSO | 2.5 mM in 0.25% DSMO | 10 mL |
| Sodium pyruvate | 10 mM | 2.5 mM | 10 mL |
| Phosphate buffer pH 8 | 200 mM | 50 mM | 10 mL |

Seal tubes with Parafilm and agitate in an orbital shaker in the dark at room temperature. Stop at each of 1 min, 5 min, 15 min, 30 min, 60 min, 90 min, 120 min, and 18 hours. Stop the reactions in appropriate tubes by heat denaturation (e.g. 5 minutes in boiling water). Fill each blank with 250 µL 200 mM phosphate buffer pH 8 and 500 µL MilliQ water for a final ATA and phosphate buffer concentrations of $[E]_{18h}$ and 50 mM respectively. Create a standard curve for Acetophenone concentration vs. A245 with a dilution series with 156.25 mM in 50 mM phosphate buffer pH 8 as the highest concentration. The diluent will be 50 mM phosphate buffer pH 8, as will be the blank for the standard curve.

Pellet all immobilized enzyme using a permanent rare-earth magnet. Dilute the supernatant from each tube: 62.5 µL into 937.5 µL MilliQ water. In triplicate, read the $A_{245}$ from each diluted reaction sample and blank with diluted enzyme blanks. Use the acetophenone standard to calculate the concentration of acetophenone in diluted supernatants. Calculate the final AP concentrations in reaction tubes by multiplying the AP concentration in supernatant by the dilution factor (1000/62.5).

Optimized immobilized ATA is selected by plotting the amount of MBA converted to acetophenone against time and determining the $V_{max}$ from the slope of the kinetic graph in the linear region.

Reusability is assayed over 5 cycles as follows: Select the 10800 min (18 h) immobilized ATA sample that has the highest Vmax (and which should also be able to complete the reaction by 18 h) as well as its blank. Pellet the immobilized ATA with a permanent rare-earth magnet. Remove the supernatant.

A kinetic time course is determined: Prepare 150 µL 6 M HCl. Prepare 300 µL each of 10 mM MBA in 1% DMSO, 10 mM sodium pyruvate, and 200 mM phosphate buffer pH 8. Start the reaction by pipetting the 750 µL of Reaction Mix into the reaction tube. This brings the enzyme concentration to $[E]_{18h}$.

TABLE 14

Reaction Mix for Screening Assay

| Reagent | [Stock] | [Assay] | Volume |
| --- | --- | --- | --- |
| MBA | 10 mM in 1% DMSO | 2.5 mM in 0.25% DSMO | 300 µL |
| Sodium pyruvate | 10 mM | 2.5 mM | 300 µL |
| Phosphate buffer pH 8 | 200 mM | 50 mM | 300 µL |

Seal tubes with Parafilm and agitate in an orbital shaker in the dark at room temperature. Stop after 18 hours with 100 µL 6 M HCl. Fill the blank with 250 µL 200 mM phosphate buffer pH 8 and 500 µL MilliQ water for a final ATA and phosphate buffer concentrations of $[E]_{18h}$ and 50 mM respectively. Determine the amount of MBA converted to acetophenone during this immobilized ATA recycling test. Test for reusability.

The binding isotherm determines the basic conditions for the immobilization of ATA with MNP: optimal pH, minimum nanoparticle:enzyme ratio, and minimum contact time for complete immobilization. Through the screening of nanoparticle concentrations for immobilizing ATA, the conversion of MBA to AP is demonstrated by immobilized ATA and the best concentration of nanoparticles for immobilization is determined. This optimized ATA may at least match free enzyme for 18 h conversions for industrially relevant time scale and may have a comparable $V_{max}$. Once an optimized ATA is found, it is retrieved and reused without loss in 18 hours of activity over 5 cycles.

Example 8

Automated Continuous-Flow Production of Magnetically-Immobilized Nanoparticles

A machine was constructed and used to magnetically immobilize an exemplary enzyme, HRP, in MNP clusters. More than 99% immobilization efficiency was demonstrated for up to 50% loading. The immobilized HRP had superior activity to free enzyme in the presence of inhibitory concentrations of $H_2O_2$.

The machine was constructed and used to immobilize horseradish peroxidase (HRP) in superparamagnetic iron nanoparticle (NP) clusters that showed continuous-flow enzyme immobilization. HRP was entrapped with MNP clusters to 25% and 50% loading with >99% immobilization efficiency. The activity of immobilized HRP was evaluated by the rate of formation of a quinoneimine dye, the complex of 4-aminoantipyrene (4-AAP) and phenol, measured by the increase in absorbance at 500 nm. With the reaction mixture of 0.5 mM phenol, 0.5 mM 4-AAP, 100 mM phosphate buffer pH 7.4, 2.5 mM $H_2O_2$, and 2 nM HRP, the 50% loading immobilized HRP achieve an initial reaction velocity (µM quinoneimine dye formed/minute) that was superior to that of free HRP by a factor of 5±0.1 under the conditions tested.

Phenol, 4-AAP, lyophilized HRP, and buffer salts was from Sigma-Aldrich. $H_2O_2$ (30%) was provided by Fisher Scientific. The HRP was dissolved in MilliQ water and stock solution concentration determined by its absorbance at 404 nm with the extinction coefficient 102 $mM^{-1}cm^{-1}$. All other solutions were prepared with MilliQ water as well.

Immobilization of HRP: HRP and MNP were combined in continuous-flow with flow rate controlled by a Perkin-Elmer Series 200 Micro Pump dual-pump HPLC system to entrap HRP in MNP clusters (level 1). Immobilized enzyme was prepared using equal volumes of 80 µg/mL MNP and 20 or 40 µg/mL HRP for final concentrations of 10 µg/mL HRP per 40 µg/mL MNP (25% loading) and 20 µg/mL HRP per 40 µg/mL MNP (50% loading). Before use, MNP suspension was brought to pH 5 using 1 M HCl and NaOH and sonicated for 1 min at 40% amplitude by the Fisher Scientific Sonic Dismembrator (FB-505). Both reagents were pumped through 0.762 mm inner diameter stainless steel tubing at a rate of 0.833 mL/min and combined in a T-mixer, resulting in a combined output of 1.67 mL/min. After the reagents reached the T-mixer, the output was flowed through 1.016 mm inner diameter stainless steel tubing. To ensure homogeneity and dispersal MNP, the MNP solution was passed through a coil of stainless steel tubing placed in cold water with the sonicator probe positioned at the coil's center, pulsing on and off in two second intervals at 40% amplitude. The MNP reservoir was also placed adjacent to the sonicator probe to maintain MNP dispersal. In this way, for each of 25% and 50% enzyme loadings, five 1 mL batches of level 1 were collected in microfuge tubes. Further immobilization of unbound enzyme outside of continuous-flow was stopped by collecting immobilized HRP directly onto 800 µg magnetite powder (level 2), then mixing level 1 and level 2 thoroughly for 10 min with an orbital shaker. The level 2 was pelleted with a permanent magnet and the supernatant collected for protein quantification. The pellets were then resuspended with 1 mL MilliQ water.

Quantification of immobilized enzyme: A modified Bradford Assay as described above was used to measure the quantity of immobilized HRP captured on level 2 and was compared to the total protein detected in level 1 solution.

Figure 3:
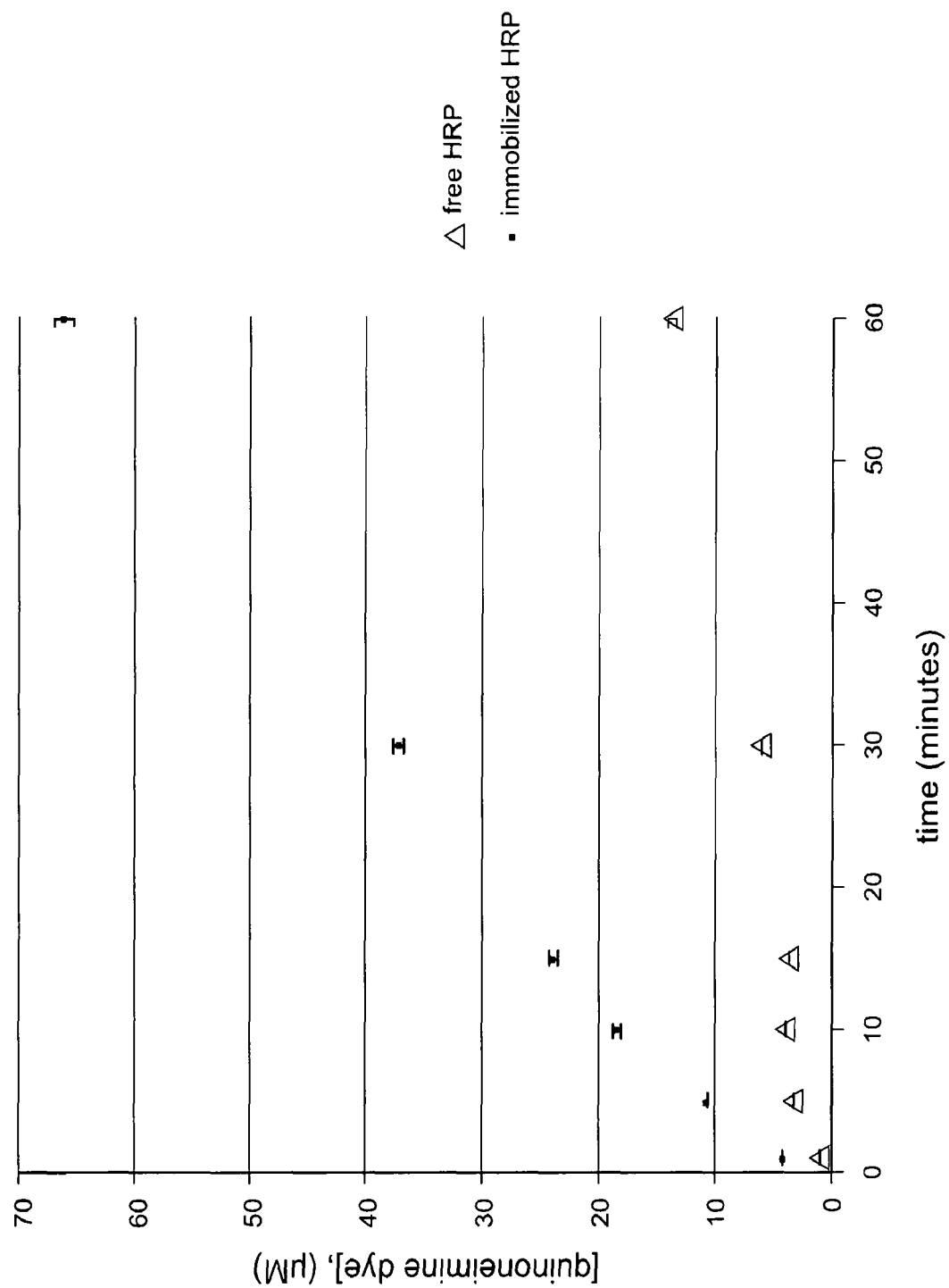
FIG. 3: The activity of immobilized HRP generated in an automated BNC production machine. The activity was measured by the increase in absorbance at 500 nm due to the formation of a pink quinoneimine dye.

HRP activity assay: The activity of immobilized HRP was determined using the increase in absorbance at 500 nm due to the formation of a pink quinoneimine dye (FIG. 3). The complex of phenol and 4-aminoantipyrene (4-AAP) has an extinction coefficient of 13.78 $mM^{-1}cm^{-1}$. The reaction mixture contained 0.5 mM phenol, 0.5 mM 4-AAP, 100 mM phosphate buffer pH 7.4, excess $H_2O_2$ (2.5 mM), and 2 nM HRP, and was carried out in microfuge tubes at room temperature while being agitated in an orbital shaker. Endpoint absorbance readings were made from 1-60 min of contact time, read in a UV transparent microplate using a Bio-Tek® Epoch plate-reader with pathlength correction to 1 cm. Activity of free HRP and 50% loaded immobilized HRP were assessed by comparison of their initial reaction velocity in terms of µM quinoneimine dye formed per minute.

Figure 4:
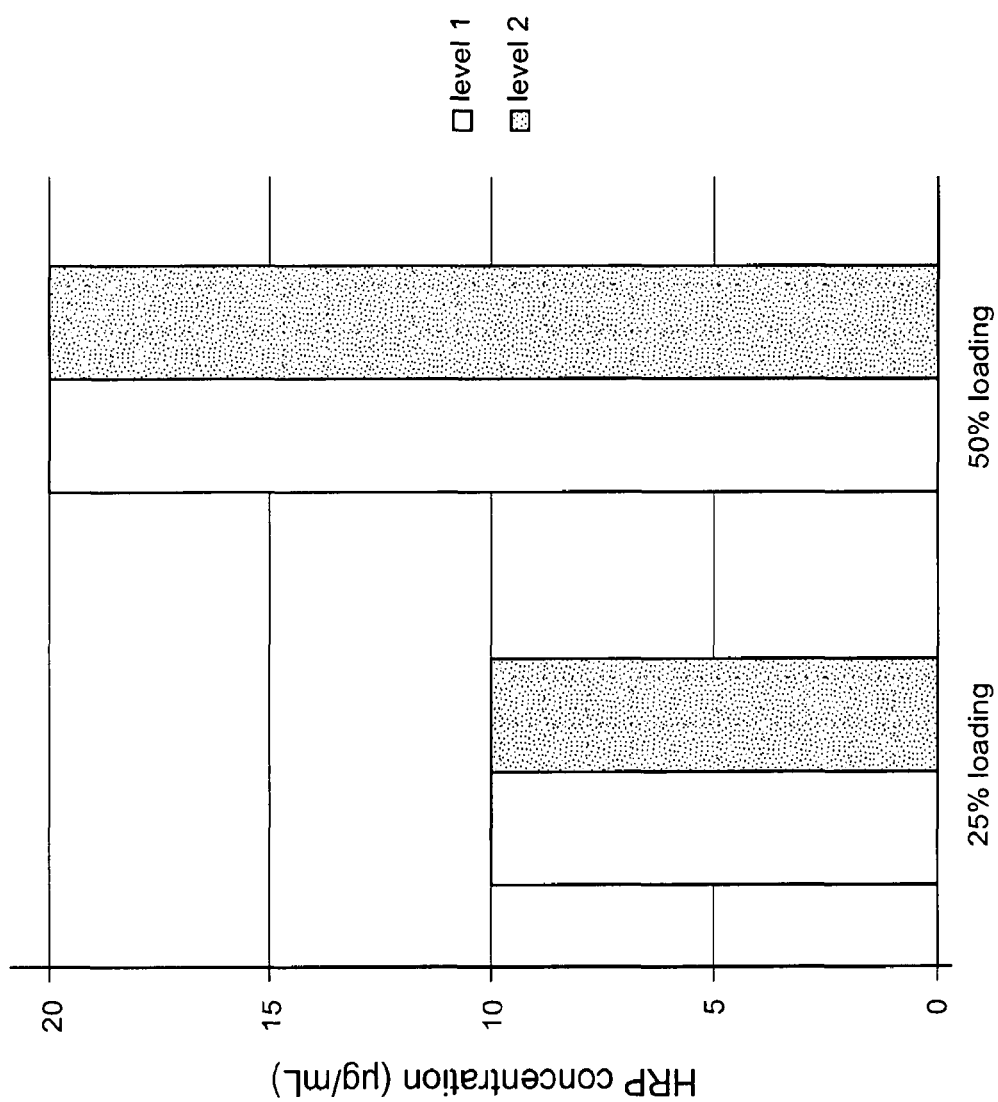
FIG. 4: The amount of enzyme loaded into BNCs using an automated BNC production machine. The graph shows the concentration of HRP protein immobilized into MNPs (level 1). It also shows the concentration of HRP protein in BNCs that are further contained in Magnetic Microparticles (MMP) (level 2).

Immobilization Efficiency: A Bradford Assay for HRP concentration revealed that more than 99% of the enzyme was entrapped by MNP in both 25% and 50% loaded samples. FIG. 4 shows the amount of protein measured in solution as level 1 immobilized HRP and the amount removed from solution, bound to level 2 immobilized HRP. The quantity of enzyme on level 2 was calculated as the difference in total protein and unbound protein in solution.

Activity of immobilized HRP: The initial velocity of the 4-AAP:phenol reaction catalyzed by level 2 immobilized HRP was determined by the slope of the linear region for the plot of concentration quinoneimine dye vs. time (FIG. 3). The immobilized HRP had an initial velocity of 1.58±0.03 µM/min. Compared to free HRP, which had an initial velocity of 0.31±0.04 µM/min, immobilized HRP had a 5-fold greater initial velocity. Peroxidases experience substrate inhibition by hydrogen peroxide, a sensitivity that was reduced by the protection conferred by entrapment in nanoparticles.

Example 9

Sonication and Flow Rate Optimization for Automated BNC Synthesis

The immobilization of Horse Radish Peroxidase within magnetite nanoparticle (MNP) clusters was optimized using a continuous flow assembly. The continuous flow system mixed the enzymes with monodisperse nanoparticles in very precise concentration ratios. The resulting BNCs were immediately templated onto magnetic materials. The assembly system comprised two HPLC pumps (Perkin-Elmer Series 200 Micro Pumps) outfitted with 0.0625 inch OD×0.043 inch ID 316 stainless steel tubing. The pumps, labeled A and B, transferred MNPs and enzymes, respectively, through separate segments of steel tubing (also designated A and B). They were combined downstream by a steel tee fitting that acted as a mixing chamber. To achieve a monodisperse suspension of MNP, tubing A was coiled three times into "sonication loops" 3.18 cm in diameter and placed inside a sonic water bath (Branson 1800). The tubing downstream from the tee fitting was also coiled ten times into 7.6 cm "incubation loops" to enhance MNP-enzyme mixing that terminated at the collection port.

Prior to the first run each day, the pumps were cleaned by running 35 mL of 1M HCl at 3.00 mL/min followed by 50 mL deionized water. Next, 5 mL horseradish peroxidase (HRP) and 5 mL MNP solutions, both prepared at the desired concentrations, were transferred to separate reservoirs. The MNPs were then sonicated at 25% amplitude continuously for 60 s (505 Sonic Dismembrator, Fisher-Scientific Model outfitted with a ¼ inch probe tip), which corresponds to a sonication power of approximately 12-14 W. The MNP tube was fixed in place in the Branson bath where 40 kHz sonication was maintained for the duration of the run. The plastic intake tubing for the two pumps were then affixed inside their respective sample reservoirs, as far beneath the surface of the liquids as possible to prevent air intake. Both pumps were then set at the desired flow rate (i.e. integral and fractional multiples of 0.83 mL/min), and Pump A initialized pumping. Twenty seconds after Pump A began, Pump B was started. At the collection port, the first 1 mL elution was collected when the MNPs in the elutions stopped aggregating. Collection continued until ten 1 mL sample fractions were obtained. The pumps were then purged with 50 mL deionized water in preparation for the next trial. This collection protocol was followed for flow rates 0.21 (¼×), 0.42 (½×), 0.83 (1×), 1.66 (2×), and 3.32 (4×) mL/min.

For each pump speed, five 1 ml samples were agitated continuously at room temperature to ensure excess time for the MNP to immobilize the enzyme. Eight samples were centrifuged at 15,000 g for 15 minutes. A Bradford assay was then conducted on the supernatant of each centrifuged sample.

The remaining 2 mL of each trial was used to measure the activity of immobilized HRP and was kept agitated at 25° C. until the assay was ready to be conducted. Hydrogen peroxide at 25 mM was used as the substrate for the assays. Phenol at 10 mM and 4-aminoantipyrine (4-AAP) at 10 mM, combined in 10 mL solution with phosphate-buffered saline at pH 7.4 and Milli-Q water, was used as the reaction mixture. All samples containing enzyme were diluted to 25 nM, then diluted further to 2.5 nM after the reaction mixture and peroxide were added to the reaction well.

Figure 5:
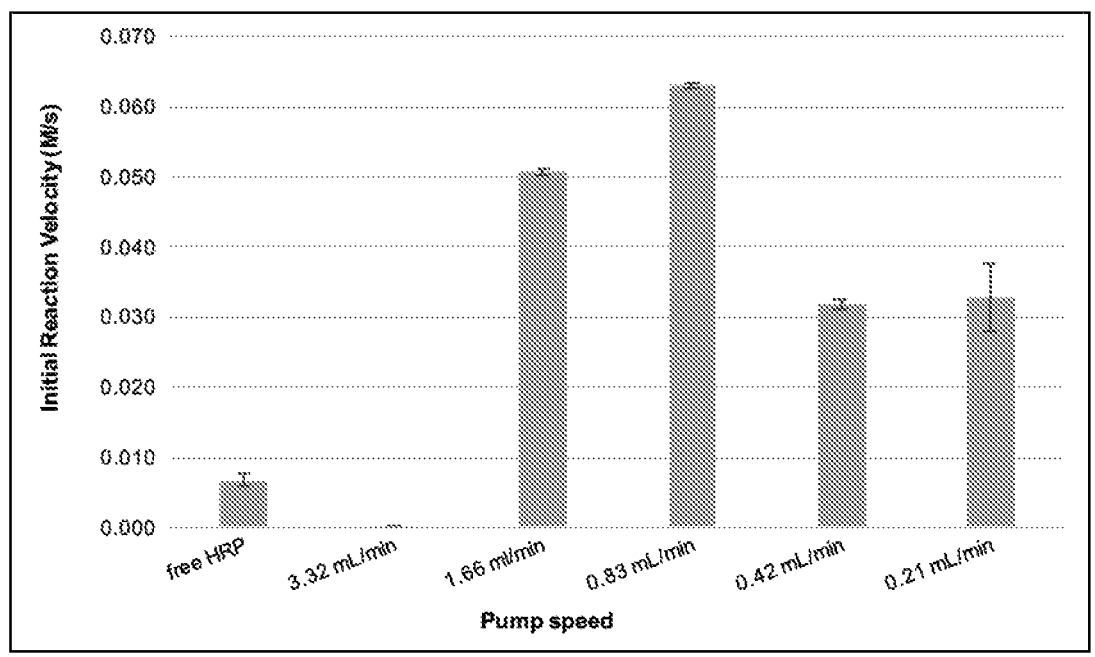
FIG. 5: Reaction velocities of eluted samples obtained from an automated BNC production machine at different pump speeds. The figure compares free and magnetically immobilized Horseradish peroxidase (HRP). Velocities shown are derived from the first 315 seconds of the reaction using 2.5 mM HRP.

Absorbance was determined in real time over 10 minutes as the HRP-peroxide reaction proceeded inside an Epoch Microplate Spectrophotometer scanning at 500 nm. FIG. 5 shows the initial reaction velocities of MNP-immobilized HRP at a 100:1 MNP:HRP concentration ratio for each pump speed tested compared to that of free HRP. The velocities are from the first 315 seconds of the reaction using HRP at a concentration of 2.5 nM. The assay concentration was obtained by diluting the original elutions that contained 25 μg/mL HRP and 2,500 μg/mL MNP. An extinction coefficient of $\varepsilon=13.78$ $mM^{-1}cm^{-1}$ and an average path length of 0.717 cm were assumed to calculate product formation.

MNP-immobilized HRP exhibited five to nine times higher enzymatic activity than HRP alone (FIG. 5). The only exception was the 3.32 mL/min sample. This likely eluted too quickly for the MNP and HRP to interact and form the desired clusters. Only water eluted upon collection. It is worth noting that at a pump speed of 0.83 mL/min, the highest activity was achieved (a nine-fold increase in reaction velocity compared to free HRP), but as the pump speed increased or decreased relative to this optimal point, activity decreased. Thus, the pump speed affects enzyme activity: higher flow rates improve mixing turbulence but also reduce MNP-enzyme contact time.

Example 10

Automated Nitrilase Immobilization on Magnetic Supports

Materials and Methods. BNCs containing nitrilase (14 identical subunits with MW=41 kDa, pI=8.1) and magnetite nanoparticles were prepared with 20% loading using an automated BNC assembly system, then templated onto fine magnetite powder (50-100 nm) scaffolds, resulting in biomicrocatalysts (BMCs) with 1% overall loading. The optimized immobilization condition resulted in >99% retained activity relative to the free enzyme for synthesis of nicotinic acid.

Recombinant nitrilase from expressed in *E. coli*, 3-cyanopyradine, o-phthaldialdehyde, 2-mercaptoethanol, BICINE-KOH, and ethanol were purchased from Sigma (St. Louis, Mo., USA). Hydrochloric acid, ammonium chloride, and potassium hydroxide were from Macron Fine Chemicals (Center Valley, Pa., USA). Quick Start™ Bradford Protein Assay was purchased from Bio-Rad (Hercules, Calif., USA). Magnetite nanoparticles and magnetic macroporous polymeric hybrid scaffolds were synthesized as previously described in WO2012122437 and WO2014055853, incorporated by reference herein in their entirety. Stock solutions were made in 18.2MΩ-cm water purified by Barnstead™ Nanopure™. Fluorescence intensity was measured in Coming Costar® 3925 black-bottom fluorescence microplates using a Biotek® Synergy™ H1 plate reader operated with Gen5™ software. A sonicator (FB-505) with a ⅛ inch probe was purchased from Fisher Scientific® (Waltham. Mass.). The automated BNC assembler used two linked NE-1000 syringe pumps by New Era Pump Systems Inc. (Farmingdale, N.Y.). Stainless-steel tubing, a mixing stainless-steel tee, and two PEEK seven-port radial manifolds all with 0.04 in internal diameters and 0.125 in outer diameters, along with necessary PEEK or stainless-steel fittings, were purchased from McMaster-Carr (Cleveland, Ohio).

Lyophilized nitrilase was dissolved in water. O-phthaldialdehyde (OPA) stock solution (75 mM) was prepared in 100% ethanol and kept on ice or stored at 4° C. 2-mercaptoethanol (2-ME) stock solution (72 mM) was also prepared in 100% ethanol immediately prior to use. Buffered OPA/ 2-ME reagent was prepared by adding 450 mL of the above solutions to 9.1 mL 200 mM pH 9.0 BICINE-KOH buffer. The buffered reagent was kept on ice until just before use when it was allowed to equilibrate to room temperature (21° C.).

A continuous-flow system for preparation of BNCs was used to improve consistency between immobilizations and to improve the mixing of free enzyme and MNPs to achieve a more homogenous product with controlled BNC diameter. The system comprised two syringe pumps, each with a 60 mL syringe acting as reservoirs for free enzyme or sonicated nanoparticles. The enzyme and MNPs flow through stainless-steel tubing with 0.04" interior diameter, meeting at a stainless-steel mixing tee. Preceding the tee, the MNP line was coiled and submerged in water. The sonic probe was positioned in the center of this coil and the probe was active at 40% amplitude while MNPs flowed through the tubing. This coil/sonicator arrangement served the purpose of in-line sonication. After the tee was an a seven-port PEEK manifold inline mixer that split the flow into six channels. Each of these channel fed into a second manifold wherein they were recombined with a single output. Finally, an additional length of tubing was placed after the second manifold to enable collection of BNCs.

Free nitrilase stock (250 μg/mL) was adjusted to pH 8.75 and a 5 mL 1250 μg/ml MNP stock was sonicated at the 40% amplitude for 1 min, equilibrated to room temperature using a water bath, then its pH was adjusted to 3. Free nitrilase (2 mL) was loaded into the enzyme pump syringe and an equal volume of MNP was loaded into the MNP pump. Both pumps were started simultaneously using Syringe Pump ProV1 pump control software, each set at 30 mL/min for an effective flow rate of 60 mL/min. Manually assembled nitrilase BNCs were prepared by adding 1 mL of sonicated MNP stock to 1 mL of nitrilase stock then pipette mixing 10 times. Nitrilase BMCs were prepared by adding 1 mL of automatically assembled or manually assembled BNCs to 594 μL 20 mg/mL magnetite powder and pipette mixing 10 times. These BMCs were gently mixed on a rotator for 1 hour then pelleted magnetically. Their supernatants were saved for quantification of immobilized nitrilase. These BMCs are referred to automated and manual BMCs respectively.

Nitrilase reaction and activity determination. Both the nitrilase reaction and activity determination methods are based on a modification of the methods described by Banerjee, *Biotechnol. and Appl. Biochem.* 37(3):289-293 (2003). Briefly, nitrilase catalyzed the hydrolysis of 3-cyanopyridine to nicotinic acid, liberating ammonia. Nitrilase reactions were run at 50° C. for 20 hours in 2 mL microcentrifuge tubes in a total reaction volume of 1 mL containing 50 mM 3-cyanopyridine, 87.5 mM BICINE-KOH, pH 9.0, and 218 nM free or immobilized nitrilase (NIT). The reaction was stopped by adding 13.35 μL 100 mM HCl to an equal volume of nitrilase reaction mix. Immobilized NIT was pelleted magnetically and the supernatant treated with HCl.

Enzyme activity was measured fluorometrically by detecting incorporation of ammonia into an isoindole fluorochrome. Buffered reagent (624 µL) was added to supernatant and was allowed to mix gently for 20 min at room temperature. After incubation, 150 µL 100 mM HCl was added to this solution to increase fluorescent signal. Fluorescence intensity was measured using 412 nm excitation, 467 nm emission with gain auto-adjusted relative to wells with highest intensity. Each fluorescence reading included an internal linear $NH_4Cl$ standard curve ($R^2>0.99$). A unit (U) of nitrilase activity was defined as 1 µmol $NH_3$ liberated per minute at 50° C. in 87.5 mM BICINE-KOH (pH 9.0).

Protein Quantification. BMCs were pelleted magnetically, and protein content in the supernatant was determined, including a linear nitrilase standard curve ($R^2>0.99$). Bradford, Analytical Biochem. 72(1-2):248-254 (1976).

Results

Controls showed that there was no uncatalyzed ammonia liberation. Automatically and manually prepared nitrilase BNCs were immobilized on magnetite powder (50-100 nm) scaffolds with >99% immobilization yield for an effective loading of 1% on BMC (Table 15). The activity automated nitrilase BMCs was largely retained (>99%) relative to free nitrilase, while manual nitrilase BMCs had lower activity (~38%).

TABLE 15

Enzyme Loading into BMCs

| Enzyme | Automatic Immobilization (%) | Manual Immobilization (%) |
|---|---|---|
| Nitrilase (NIT) | 1 | 1 |
| ω-transaminase (ωTA) | 1 | 1 |
| Carbonic anhydrase (CAN) | 9.5 | 9.5 |
| Catalase (CAT) | 0.79 | 0.7 |
| Glucose Isomerase (GIS) | 8.1 | 9.6 |
| Glutamine synthetase (GluS) | 1.0 | 0.94 |
| Horseradish peroxidase (HRP) | 5.6 | 5.6 |

Example 11

Transaminase Immobilization on Magnetic Supports for Biocatalysis

BNCs containing ω-transaminase (EC 2.6.1.18, MW=195 kDa) and magnetite nanoparticles were prepared with 20% loading using an automated BNC assembly system, then templated onto fine magnetite powder (50-100 nm) scaffolds, resulting in BMCs with 1% overall loading. The optimized immobilization condition resulted in >99% retained activity relative to the free enzyme for synthesis of acetophenone from (R)-(+)-α-methylbenzylamine.

Materials and Equipment. Recombinant ω-transaminase (ωTA) was from *Mycobacterium vanbaaleni* expressed in *E. coli*. (R)-(+)-α-methylbenzylamine (MBA), sodium pyruvate and acetophenone (AP) was from Sigma (St. Louis, Mo., USA). Dimethyl sulfoxide (DMSO) was purchased from Fisher Scientific (Fair Lawn, N.J., USA). Hydrochloric acid, sodium hydroxide, and phosphate buffer salts were from Macron Fine Chemicals (Center Valley, Pa., USA). Quick Start™ Bradford Protein Assay was purchased from Bio-Rad (Hercules, Calif., USA). Stock solutions were made with 18.2 MΩ-cm water purified by Barnstead™ Nanopure™ water. Absorbance was measured in triplicate in Costar™ 3635 UV-transparent microplates using Biotek Epoch™ plate reader operated with Gen5™ software. A sonicator (FB-505) with a ⅛ inch probe was from Fisher Scientific® (Waltham. Mass.). The automated BNC assembler used two linked NE-1000 syringe pumps by New Era Pump Systems Inc. (Farmingdale, N.Y.). Stainless-steel tubing, a mixing stainless-steel tee, and two PEEK seven-port radial manifolds all with 0.04 in internal diameters and 0.125 in outer diameters, along with necessary PEEK or stainless-steel fittings, were from McMaster-Carr (Cleveland, Ohio).

Reagents. Lyophilized ωTA was dissolved in water. (R)-(+)-α-methylbenzylamine (MBA) stock solution was prepared by dissolving 12.78 µL MBA in 100 µL DMSO, then bringing the total volume to 10 mL with water for a final concentration of 10 mM. A 45 mM stock of sodium pyruvate was prepared by dissolving sodium pyruvate powder in water. Acetophenone stock solution was prepared by dissolving 12 µL AP in water. All stock solutions were kept on ice. Dilutions were made just before use in assays and were allowed to equilibrate to room temperature (21° C.).

Automated BNC Assembly. A continuous-flow system for preparation of BNCs was constructed to improve consistency between immobilizations and to improve the mixing of free enzyme and MNPs to achieve a more homogenous product with controlled BNC diameter. The system comprised two syringe pumps, each with a 60 mL syringe acting as a reservoir for free enzyme or sonicated nanoparticles. The enzyme and MNPs flow through stainless-steel tubing with a 0.04 inch interior diameter and meeting at a stainless-steel mixing tee. Preceding the tee, the MNP line was coiled and submerged in water. The sonic probe was positioned in the center of this coil and the probe was active at 40% amplitude while MNPs flowed through the tubing. This coil/sonicator arrangement provided in-line sonication. Before the tee was an inline seven-port PEEK manifold mixer that split the flow into six channels. Each of these channel fed into a second manifold wherein they were recombined with a single output. Finally, an additional length of tubing was placed after the second manifold for collecting BNCs.

Immobilization. Free ωTA stock (250 µg/mL) was adjusted to pH 7.15 and a 5 mL 1250 µg/ml MNP stock was sonicated at the 40% amplitude for 1 min, equilibrated to room temperature using a water bath, then its pH was adjusted to 3. Free ωTA (2 mL) was loaded into the enzyme pump syringe and an equal volume of MNP was loaded into the MNP pump. Both pumps were started simultaneously using Syringe Pump ProV1 pump control software, each set at 30 mL/min for an effective flow rate of 60 mL/min. Manually assembled ωTA BNCs were prepared by adding 1 mL of sonicated MNP stock to 1 mL of ωTA stock, then pipette mixing 10 times. ωTA BMCs were prepared by adding 1 mL of automatically assembled or manually assembled BNCs to 594 µL 20 mg/mL magnetite powder and pipette mixing 10 times. These BMCs were gently mixed on a rotator for 1 hour then were pelleted magnetically. Their supernatants were saved for quantification of immobilized ωTA. These BMCs are referred to automated and manual BMCs respectively.

ω-Transaminase activity assay. ωTA activity determination methods were based on methods described by Schätzle et al., (2009), cited above, but adapted for microplates. Briefly, ωTA catalyzed the transfer of an amino-group from MBA (amine donor) to pyruvate forming AP and alanine respectively. Enzyme activity was measured by the increase in absorbance at 245 nm due to the formation of AP Mathew & Yun (2012), cited above. ωTA reactions were run at 21° C. for 1 h in 2 mL microcentrifuge tubes using with a total reaction volume of 1 mL containing 50 mM pH 8.0 phosphate buffered saline (PBS), 0.1 mM MBA, 1 mM pyruvate, and 349 nM w-transaminase. Immobilized ωTA was pelleted magnetically and its supernatant read for absorbance. AP was quantified using a linear standard curve containing 0-0.1 mM AP and 0-0.1 mM alanine ($R^2>0.99$). One unit (U) of w-transaminase activity was defined as 1 μmol AP generated per minute at 21° C. in 50 mM PBS (pH 8.0).

Protein quantification. BMCs were pelleted magnetically, and protein content in the supernatant was determined using the Bradford method, including a linear ωTA standard curve ($R^2>0.99$).

Results Controls showed that there was no uncatalyzed acetophenone formation. Automatically and manually prepared ωTA BNCs were immobilized on magnetite powder (50-100 nm) scaffolds with >99% immobilization yield for an effective loading of 1% on BMC (Table 15). The activity automated and manual ωTA BMCs was largely retained (>99%) relative to free nitrilase.

Example 12

Carbonic Anhydrase Immobilization on Magnetic Supports for Biocatalysis

BNCs containing bovine carbonic anhydrase II (CAN) (MW=30 kDa) and magnetite nanoparticles were created with 20% loading using an automated BNC assembly system then templated onto fine magnetite powder (50-100 nm) scaffolds forming BMCs with 9% overall loading. The optimized immobilization condition resulted in 95±8% retained activity relative to the free enzyme for dehydration of bicarbonate to carbon dioxide.

Materials and Equipment. Carbonic anhydrase II (CAN) from bovine erythrocytes, BICINE-KOH, HEPES-KOH, and 8-hydroxy-pyrene-1,3,6-trisulfonate (pyranine) were purchased from Sigma (St. Louis, Mo., USA). Hydrochloric acid, ammonium chloride, and potassium hydroxide were from Macron Fine Chemicals (Center Valley, Pa., USA). Quick Start™ Bradford Protein Assay was purchased from Bio-Rad (Hercules, Calif., USA). Magnetite nanoparticles were synthesized as in WO2012122437, WO2014055853 as well as magnetic macroporous polymeric hybrid scaffolds, as previously described. Stock solutions were made in 18.2MΩ-cm water purified by Barnstead™ Nanopure™. Fluorescence intensity was measured in Corning Costar® 3925 black-bottom fluorescence microplates using Biotek® Synergy™ H1 plate reader, with reagent injection system, operated with Gen5™ software. A sonicator (FB-505) with a ¼" probe was purchased from Fisher Scientific® (Waltham. Mass.). The automated BNC assembler used two linked NE-1000 syringe pumps by New Era Pump Systems Inc. (Farmingdale, N.Y.). Stainless-steel tubing, a mixing stainless-steel tee, and two PEEK seven-port radial manifolds all with 0.04 in internal diameters and 0.125 in outer diameters, along with necessary PEEK or stainless-steel fittings, were purchased from McMaster-Carr (Cleveland, Ohio).

Reagents. Lyophilized CAN was dissolved in water. Reagent A contained 2 mM $KHCO_3$ and 0.5 mM BICINE-KOH buffer, pH 8. Reagent B contained 500 pM Carbonic Anhydrase, 100 nM pyranine, and 0.5 mM HEPES-KOH buffer, pH 6.

Automated BNC Assembly. A continuous-flow system was used to prepare the BNCs. It comprised of two syringe pumps, each with a 60 mL syringe acting as a reservoir for free enzyme or sonicated nanoparticles. The enzyme and MNPs flow through stainless-steel tubing with 0.04 inch interior diameter, meeting at a stainless-steel mixing tee. Preceding the tee, the MNP line was coiled and submerged in water. The sonic probe was positioned in the center of this coil and the probe was active at 40% amplitude while MNPs flowed through the tubing. This coil/sonicator set up served the purpose of in-line sonication. Subsequent to the tee was an inline seven-port PEEK manifold mixer that split the flow into six channels. Each of these channel fed into a second manifold wherein they were recombined with a single output. Finally, an additional length of tubing was placed after the second manifold to enable collection of BNCs.

Immobilization. Free CAN stock (250 μg/mL) was adjusted to pH 6 and a 5 mL 1250 μg/mL MNP stock was sonicated at the 40% amplitude for 1 min, equilibrated to room temperature using a water bath, then its pH was adjusted to 11. Free CAN (2 mL) was loaded into the enzyme pump syringe and an equal volume of MNP was loaded into the MNP pump. Both pumps were started simultaneously using Syringe Pump ProV1 pump control software, each set at 30 mL/min for an effective flow rate of 60 mL/min. Manually assembled CAN BNCs were prepared by adding 1 mL of sonicated MNP stock to 1 mL of CAN stock, then pipette mixing 10 times. CAN BMCs were prepared by adding 1 mL of automatically assembled or manually assembled BNCs to 62.5 μL 20 mg/mL magnetite powder and pipette mixing 10 times. These BMCs were gently mixed on a rotator for 1 hour, then were pelleted magnetically. Their supernatants were saved for quantification of immobilized ωTA. These BMCs are referred to automated and manual BMCs respectively.

Carbonic Anhydrase Activity Assay: CAN reversibly catalyzes dehydration of carbonic acid:

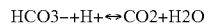

The standard carbonic anhydrase activity assay is the Wilbur-Anderson method. Wilbur & Anderson, *J. Biol. Chem.* 176:147-154 (1948). The rate of pH decrease in a buffered $CO_2$-saturated solution from 8.3 to 6.3 is measured. This is caused by the formation of bicarbonate from carbon dioxide. An alternative fluometric pH-based assay was used as previously described by Shingles & Moroney, *Analytical Biochemistry* 252(1):190-197 (1997). Briefly, pyranine is used as a fluorescent pH indicator. The increase in pH due to the dehydration of bicarbonate that is reflected by an increase in fluorescence intensity. The reaction was initiated by mixing equal volumes of reagents A and B. Reagent A was added to reagent B in a microplate well with a sample injection system and fluorescence reading were begun immediately. Due to high reaction velocities, all sample reads were performed one well at a time in triplicate. Fluorescence was measured using a pH sensitive ($F_s$) and insensitive ($F_{is}$) excitation wavelengths (466 nm and 413 nm respectively) with a 512 nm emission wavelength. Fluorescence intensity was converted to pH using a linear calibration curve of $F_s/F_{is}$ versus pH for buffered standards (pH 6-10) included on each plate. Shingles & McCarty, *Plant Physiol.* 106(2):731-737 (1994). One unit (U) of CAN activity was defined as the change in pH per second during the first 10 seconds of measurement under the conditions described above.

Protein quantification. BMCs were pelleted magnetically, and protein content in the supernatant was determined using the Bradford method, including a linear CAN standard curve ($R^2>0.99$), 2.5-10 μg/mL.

Results

Controls showed that there was no uncatalyzed pH change. CAN BNCs were immobilized automatically and manually on magnetite powder (50-100 nm) scaffold with 95% immobilization yield each for an effective loading of 9% on BMC (Table 15). The activity of carbonic anhydrase hybrid scaffold and magnetite powder BMCs were also largely retained (>95%) relative to free carbonic anhydrase Example 13

Catalase Immobilization on Magnetic Supports for Biocatalysis

BNCs containing catalase (MW=240 kDa) and magnetite nanoparticles were prepared with 30% loading using an automated BNC assembly system, then templated onto fine magnetite powder (50-100 nm) scaffolds, resulting in BMCs with 0.83% overall loading. The optimized immobilization condition resulted in >99% retained activity relative to the free enzyme.

Materials and Equipment. Bovine liver catalase (CAT) was purchased from Sigma (St. Louis, Mo., USA). Hydrogen peroxide, Hydrochloric acid, sodium hydroxide, and phosphate buffer salts were from Macron Fine Chemicals (Center Valley, Pa., USA). Quick Start™ Bradford Protein Assay was purchased from Bio-Rad (Hercules, Calif., USA). Stock solutions were made with 18.2 Me-cm water purified by Barnstead™ Nanopure™. Absorbance was measured in triplicate in Costar™ 3635 UV-transparent microplates using Biotek Epoch™ plate reader operated with Gen5™ software. A sonicator (FB-505) with a ⅛" probe was purchased from Fisher Scientific® (Waltham. Mass.). The automated BNC assembler used two linked NE-1000 syringe pumps by New Era Pump Systems Inc. (Farmingdale, N.Y.). Stainless-steel tubing, a mixing stainless-steel tee, and two PEEK seven-port radial manifolds all with 0.04 in internal diameters and 0.125 in outer diameters. along with necessary PEEK or stainless-steel fittings, were purchased from McMaster-Carr (Cleveland, Ohio).

Reagents. Lyophilized CAT was dissolved in water and quantified using the Bradford method with bovine serum albumin standards. All stock solutions were kept on ice. Dilutions were made just before use in assays and were allowed to equilibrate to room temperature (21° C.).

Automated BNC Assembly. A continuous-flow system was used to prepare BNCs. The system comprised two syringe pumps, each with a 60 mL syringe acting as a reservoir for free enzyme or sonicated nanoparticles. The enzyme and MNPs flow through stainless-steel tubing with a 0.04 inch interior diameter and meeting at a stainless-steel mixing tee. Preceding the tee, the MNP line was coiled and submerged in water. The sonic probe was positioned in the center of this coil and the probe was active at 40% amplitude while MNPs flowed through the tubing. This coil/sonicator set up served the purpose of in-line sonication. Subsequent to the tee was an inline seven-port PEEK manifold mixer that split the flow into six channels. Each of these channel fed into a second manifold wherein they were recombined with a single output. Finally, an additional length of tubing was placed after the second manifold to enable collection of BNCs.

Immobilization. Free CAT stock (300 µg/mL) was adjusted to pH 7 and a 5 mL 1000 µg/mL MNP stock was sonicated at the 40% amplitude for 1 min, equilibrated to room temperature using a water bath, then its pH was adjusted to 3. Free CAT (2 mL) was loaded into the enzyme pump syringe and an equal volume of MNP was loaded into the MNP pump. Both pumps were started simultaneously using Syringe Pump ProV1 pump control software, each set at 30 mL/min for an effective flow rate of 60 mL/min.

Manually assembled CAT BNCs were prepared by adding 1 mL of sonicated MNP stock to 1 mL of CAT stock, then pipette mixing 10 times. CAT BMCs were prepared by adding 1 mL of automatically assembled or manually assembled BNCs to 725 µL 20 mg/mL magnetite powder (50-100 nm) and pipette mixing 10 times. These BMCs were gently mixed on a rotator for 1 hour, then were pelleted magnetically. Their supernatants were saved for quantification of immobilized CAT. These BMCs are referred to automated and manual BMCs respectively.

Catalase Activity Assay. CAT catalyzes the degradation of hydrogen peroxide into water and oxygen. Enzyme activity was measured by the decrease in absorbance at 240 nm due to the decrease in peroxide Li & Schellhorn, *J. Biomolecular Techniques* 18(4):185-187 (2007). CAT reactions were run at 21° C. for 2 minutes in 2 mL microcentrifuge tubes with a total reaction volume of 1 mL containing 100 mM pH 7.0 phosphate buffered saline (PBS) and 5 nM catalase. Immobilized CAT was pelleted magnetically and its supernatant read for absorbance. Hydrogen peroxide was quantified using a linear standard curve containing 10-100 mM $H_2O_2$ ($R^2$>0.99). One unit (U) of catalase activity was defined as 1 µmol $H_2O_2$ degraded per minute at 21° C. in 50 mM PBS (pH 7.0).

Protein Quantification. BMCs were pelleted magnetically, and protein content in the supernatant was determined using the Bradford method, including a linear CAT standard curve ($R^2$>0.99).

Results

Controls showed that there was no uncatalyzed degradation of $H_2O_2$. Automatically prepared CAT BNCs were immobilized on magnetite powder (50-100 nm) scaffolds with 79% immobilization yield for an effective loading of 0.79% on BMC (Table 15). Manually prepared CAT BNCs were immobilized on the same type of scaffold with a 70% immobilization yield and an effective loading of 0.7%. The activity of CAT BMCs was largely retained relative to free catalase, 96% and 78% residual activity for automated and manual BMCs respectively Example 14:

Glucose Isomerase Immobilization on Magnetic Supports for Biocatalysis

Gensweet™ from DuPont, is a soluble GIS. It's activity was assessed using conversion of fructose to glucose. BNCs containing glucose isomerase (MW=173 kDa) and magnetite nanoparticles were prepared with 80% loading using an automated BNC assembly system, then templated onto fine magnetite powder (50-100 nm) scaffolds, resulting in BMCs with 8.1% overall loading. The optimized immobilization condition resulted in >121% retained activity relative to the free enzyme.

Materials and Equipment. Soluble glucose isomerase (GIS), Gensweet™ was provided by DuPont (Cedar Rapids, Iowa). Horseradish peroxidase from *A. rusticana* (HRP), glucose oxidase from *A. niger* (GOX), phenol, 4-aminoantipyrine (4-AAP), 50-100 nm magnetite powder, D-(+)-fructose, and D-(+)-glucose, were purchased from Sigma (St. Louis, Mo., USA). Magnesium sulfate, hydrochloric acid, sodium hydroxide, and phosphate buffer salts were from Macron Fine Chemicals (Center Valley, Pa., USA). Quick Start™ Bradford Protein Assay was purchased from Bio-Rad (Hercules, Calif., USA). Magnetite nanoparticles were synthesized in-house at ZYMtronix Catalytic Systems (Ithaca, N.Y., USA) (PCT1 and 2), as previously described.

Stock solutions were made with 18.2 Me-cm water purified by Barnstead™ Nanopure™. Absorbance was measured in triplicate in Costar™ 3635 UV-transparent microplates using Biotek Epoch™ plate reader operated with Gen5™ software. A sonicator (FB-505) with a ⅛ inch probe was purchased from Fisher Scientific® (Waltham. Mass.). The automated BNC assembler used two linked NE-1000 syringe pumps by New Era Pump Systems Inc. (Farmingdale, N.Y.). Stainless-steel tubing, a mixing stainless-steel tee, and two PEEK seven-port radial manifolds all with 0.04 in internal diameters and 0.125 in outer diameters. The PEEK and stainless-steel fittings, were purchased from McMaster-Carr (Cleveland, Ohio).

Reagents. Fructose stock solution (5 M) was prepared quantitatively with a volumetric flask. Phenol (10 mM), 4-aminoantipyrine (4-AAP, 10 mM), pH 7.4 PBS (500 mM), glucose (100 mM), and magnesium sulfate (1 M) were prepared and stored at 4° C. The reagents equilibrated to room temperature (21° C.) before use. GIS stock was in solution form while HRP and GOX solutions were prepared from lyophilized powders.

Glucose isomerase reaction and activity determination. The GIS isomerase activity was determined using a glucose reporting reaction. The primary reaction, GIS catalyzed isomerization of fructose to glucose, was run at 65° C. in a 2 mL microcentrifuge tube with a 1 mL reaction volume containing 390 mM fructose, 50 mM pH 7.8 PBS, and 1.27-1.45 µM GIS. The reaction was run for 30 min, gently mixed on a rotator, and stopped with 50 µL 0.1 M HCl. GIS BMCs were pelleted magnetically.

The secondary reporter reaction was used to correlate glucose concentration with a colorimetric indicator formed from the complexation of phenol radicals and 4-AAP, with the formation of phenol radicals catalyzed by HRP oxidation activity. Briefly, the reporter reaction was performed at room temperature in microplates with a total volume of 250 µL containing 0.25 mM phenol, 0.25 mM 4-AAP, 50 mM pH 7.4 PBS, 30 nM HRP, 30 nM GOX, and 25 µL of supernatant from the primary reaction diluted 100-fold. The reporter reaction was allowed to run for 30 min. Glucose concentration was calculated by linear regression ($R^2>0.99$) of absorbance due to dye formation vs. glucose concentration using 25 µL glucose standards (0.125-1.25 mM) in place of diluted primary reaction supernatant. One unit of GIS activity was defined as 1 µmol isomerization of fructose to glucose per min for a 30 min incubation at 65° C.

Protein quantification. BMCs were pelleted magnetically, and protein content in the supernatant was determined using the Bradford method, including a linear GIS standard curve ($R^2>0.99$).

Results

Controls showed that there was no detectable uncatalyzed glucose formed under reaction conditions. Automatically prepared GIS BNCs were immobilized on magnetite powder (50-100 nm) scaffolds with an effective loading of 8.1% on BMC (Table 15). Manually prepared GIS BNCs were immobilized on the same scaffold with an effective loading of 9.6%. The activity of manually immobilized GIS BMCs was reduced relative to free GIS with 65% residual activity. Automatically immobilized GIS BMCs showed an increase in activity with 121% residual activity Example 15

Glutamine Synthetase Immobilization on Magnetic Supports for Biocatalysis

BNCs containing glutamine synthetase (MW=588 kDa) and magnetite nanoparticles were prepared with 16% loading using an automated BNC assembly system. It was then templated onto fine magnetite powder (50-100 nm) scaffolds resulting in BMCs with 1% overall loading. The optimized immobilization condition resulted in >99% retained activity relative to the free enzyme.

Materials and Equipment. Glutamine synthetase (GluS), from *E. coli*, 50-100 nm magnetite powder, monosodium glutamate, adenosine 5'-triphosphate (ATP), phospho(enol) pyruvic acid (PEP), β-Nicotinamide adenine dinucleotide disodium hydrate (NADH), and pyruvate kinase/lactic dehydrogenase (PK/LDH) from rabbit muscle were purchased from Sigma (St. Louis, Mo., USA). Magnesium chloride, potassium chloride, ammonium chloride, hydrochloric acid, sodium hydroxide, and phosphate buffer salts were from Macron Fine Chemicals (Center Valley, Pa., USA). Quick Start™ Bradford Protein Assay was purchased from Bio-Rad (Hercules, Calif., USA). Magnetite nanoparticles and magnetic macroporous were synthesized as previously described in WO2012122437 and WO2014055853, incorporated by reference herein in their entirety._ Stock solutions were made with 18.2 Me-cm water purified by Barnstead™ Nanopure™. Absorbance was measured in triplicate in Costar™ 3635 UV-transparent microplates using Biotek Epoch™ plate reader operated with Gen5™ software. A sonicator (FB-505) with a ⅛ inch probe was purchased from Fisher Scientific® (Waltham. Mass.). The automated BNC assembler used two linked NE-1000 syringe pumps by New Era Pump Systems Inc. (Farmingdale, N.Y.). Stainless-steel tubing, a mixing stainless-steel tee, and two PEEK seven-port radial manifolds all with 0.04 in internal diameters and 0.125 in outer diameters, along with necessary PEEK or stainless-steel fittings, were purchased from McMaster-Carr (Cleveland, Ohio).

Reagents. Phosphate buffered saline (pH 7.1 PBS, 250 mM), glutamate (3M), ATP (90 mM), PEP (50 mM), magnesium chloride (1M), potassium chloride (500 mM), ammonium chloride (1 M), NADH (50 mM), and PK/LDH (6000/900 PK/LDH activity units (U) where one unit PK converts 1 µmol per minute of PEP to pyruvate at pH 7.6 at 37° C. and one unit of LDH reduces 1 µmol pyruvate to L-lactate per minute at pH 7.5 at 37° C.) stocks were prepared and stored at 4° C. The reagents equilibrated to room temperature (21° C.) before use. GluS stock was prepared from lyophilized powder.

Immobilization. Free GluS stock (200 µg/mL) was adjusted to pH 7.1 and 5 mL of a 1.25 mg/mL MNP stock was sonicated at the 40% amplitude for 1 min, equilibrated to room temperature using a water bath, then its pH was adjusted to 3. Free GluS (2 mL) was loaded into the enzyme pump syringe and an equal volume of MNP was loaded into the MNP pump. Both pumps were started simultaneously using Syringe Pump ProV1 pump control software, each set at 30 mL/min for an effective flow rate of 60 mL/min. Manually assembled GluS BNCs were prepared by adding 1 mL of sonicated MNP stock to 1 mL of GluS stock, then pipette mixing 10 times. GluS BMCs were prepared by adding 1 mL of automatically assembled or manually assembled BNCs to 438 µL 20 mg/mL magnetite powder (50-100 nm) and pipette mixing 10 times. These BMCs were gently mixed on a rotator for 1 hour, then were pelleted magnetically. Their supernatants were saved for quantification of immobilized GluS. These BMCs are referred to automated and manual BMCs respectively.

Glutamine synthetase reaction and activity determination. GluS activity was determined using an adenosine 5'-diphosphate (ADP) reporting reaction. GluS activated by ATP catalyzed L-glutamine synthesis from glutamate and ammonium. The reaction also yielded ADP and phosphate. ATP was regenerated in a PK catalyzed reaction converting PEP to pyruvate. Finally, pyruvate is converted to L-lactate by LDH with NADH as a cofactor, yielding NAD. Reaction progress was monitored by the decrease in absorbance at 340 nm due to the decrease in NADH concentration. The reaction was run at 37° C. in a 2 mL microcentrifuge tube with a 1 mL reaction volume containing 30 mM PBS pH 7.1, 100 mM glutamate, 10 mM ATP, 1 mM PEP, 60 mM $MgCl_2$, 20 mM KCl, 40 mM $NH_4Cl$, 300 µM NADH, 8/120 U PK/LDH, 81.7 nM GluS. The reaction was run for 60 min, gently mixed on a rotator, and stopped with 50 µL 0.1 M HCl. GluS BMCs were pelleted magnetically. NADH concentration was calculated by linear regression ($R^2$>0.99) of absorbance vs. concentration of NADH standards(3-300 µM). NADH consumption was stoichiometrically correlated to formation of L-glutamine. One unit of GluS activity was defined as 1 µmol of L-glutamine synthesized per min for a 60 min incubation at 37° C.

Protein quantification. BMCs were pelleted magnetically, and protein content in the supernatant was determined using the Bradford method including a linear GluS standard curve ($R^2$>0.99).

Results

Controls showed that there was no detectable uncatalyzed glucose formed under reaction conditions. Automatically prepared GluS BNCs were immobilized on magnetite powder (50-100 nm) scaffolds with an effective loading of 1% on BMC (Table 15). Manually prepared GluS BNCs were immobilized on the same type of scaffold with an effective loading of 0.94%. The activity of manually and automatically immobilized GluS BMCs was equivalent to that of the free enzyme (>99%).

Example 16

Horseradish Peroxidase Immobilization on Magnetic Supports

BNCs containing horseradish peroxidase (MW=44 kDa) and magnetite nanoparticles were prepared with 40% nominal loading, then templated onto pure magnetite powder (50-100 nm), forming BMCs with ~5.6% effective loading. The optimized immobilization conditions resulted in a threefold increase of activity relative to the free enzyme for the oxidation of phenol.

Materials and Equipment. Horseradish peroxidase (HRP) from *A. rusticana* root, phenol, and 4-aminoantipyrine (4-AAP) were purchased from Sigma (St. Louis, Mo., USA). Hydrogen peroxide, hydrochloric acid, sodium hydroxide, and phosphate buffer salts were from Macron Fine Chemicals (Center Valley, Pa., USA). Quick Start™ Bradford Protein Assay was purchased from Bio-Rad (Hercules, Calif., USA). Magnetite nanoparticles were synthesized as previously described in WO2012122437 and WO2014055853, incorporated by reference herein in their entirety. Stock solutions were made with 18.2 MΩ-cm water purified by Barnstead™ Nanopure™ Absorbance was measured in triplicate in Costar™ 3635 UV-transparent microplates using Biotek Epoch™ plate reader operated with Gen5™ software. A sonicator (FB-505) with ⅛" inch probe was purchased from Fisher Scientific® (Waltham. Mass.). The automated BNC assembler used two linked NE-1000 syringe pumps by New Era Pump Systems Inc. (Farmingdale, N.Y.). Stainless-steel tubing, a stainless-steel mixing tee, and two PEEK seven-port radial manifolds all with 0.04 in internal diameters and 0.125 in outer diameters, along with necessary PEEK or stainless-steel fittings, were purchased from McMaster-Carr (Cleveland, Ohio).

Reagents. Lyophilized HRP was dissolved in water to form stock solutions. Fresh HRP reagent was prepared immediately prior to use: 500 mM phosphate-buffered saline (PBS) buffer, pH 7.4, 10 mM phenol, and 10 mM 4-AAP in water. This solution was stored at 4° C. and was kept in darkness until immediately before use at which point it was equilibrated to room temperature.

Immobilization. Free HRP stock (500 µg/mL) was adjusted to pH 6 and a 5 mL 1.25 mg/mL MNP stock was sonicated at the 40% amplitude for 1 min, equilibrated to room temperature using a water bath, then its pH was adjusted to 11. Free HRP (2 mL) was loaded into the enzyme pump syringe and an equal volume of MNP was loaded into the MNP pump. Both pumps were started simultaneously using Syringe Pump ProV1 pump control software, each set at 30 mL/min for an effective flow rate of 60 mL/min. Additional immobilizations were performed using 10, 20, and 40 mL/min effective flow rates. Manually assembled HRP BNCs were prepared by adding 1 mL of sonicated MNP stock to 1 mL of HRP stock, then pipette mixing 10 times. HRP BMCs were prepared by adding 1 mL of automatically assembled or manually assembled BNCs to 31.3 µL 20 mg/mL magnetite powder (50-100 nm) and pipette mixing 10 times. These BMCs were gently mixed on a rotator for 1 hour, then were pelleted magnetically. Their supernatants were saved for quantification of immobilized HRP. These BMCs are referred to automated and manual BMCs respectively.

Horseradish peroxidase activity assay. HRP irreversibly catalyzes the oxidation of phenol to phenol radicals. Phenol oxidation is monitored via the formation of a colored complex composed of a phenol radical and 4-AAP. The resulting product is a bright pinkish-red quinoneimine dye with significant absorbance at λ=500 nm. The standard horseradish activity assay—a biocatalytic form of the Emerson-Trinder method correlates the rate of absorbance increase at λ=500 nm due to the phenolic dye product formed to the enzyme activity. Wukasch et al. 48$^G$ Purdue University Industrial Waste Conference Proceedings, 423-430 (1993). HRP batch reactions for both immobilized and free HRP were run at 21° C. for 30 min in 2 mL centrifuge tubes using a total reaction volume of 1 mL containing 50 mM pH 7.4 phosphate buffered saline (PBS), 0.25 mM phenol, 0.25 mM 4-AAP, 15 nM HRP, and 1 mM $H_2O_2$ initially to begin the reaction. The batch reactions were agitated gently. Immobilized enzyme was pelleted magnetically. Absorbance of the supernatant was read in microplates using triplicates of 250 µL for each sample. Blanks containing the corresponding amounts free enzyme were also prepared to subtract background absorbance. The product dye was quantified using extinction coefficient at 500 nm (12 $mM^{-1}cm^{-1}$). One unit (U) of HRP activity was defined as 1 mmol quinoneimine dye created per minute at 21° C. in 50 mM PBS (pH 7.4).

Protein quantification. BMCs were pelleted magnetically and protein content in the supernatant was determined using the Bradford method, including a linear HRP standard curve ($R^2$>0.99).

Figure 6:
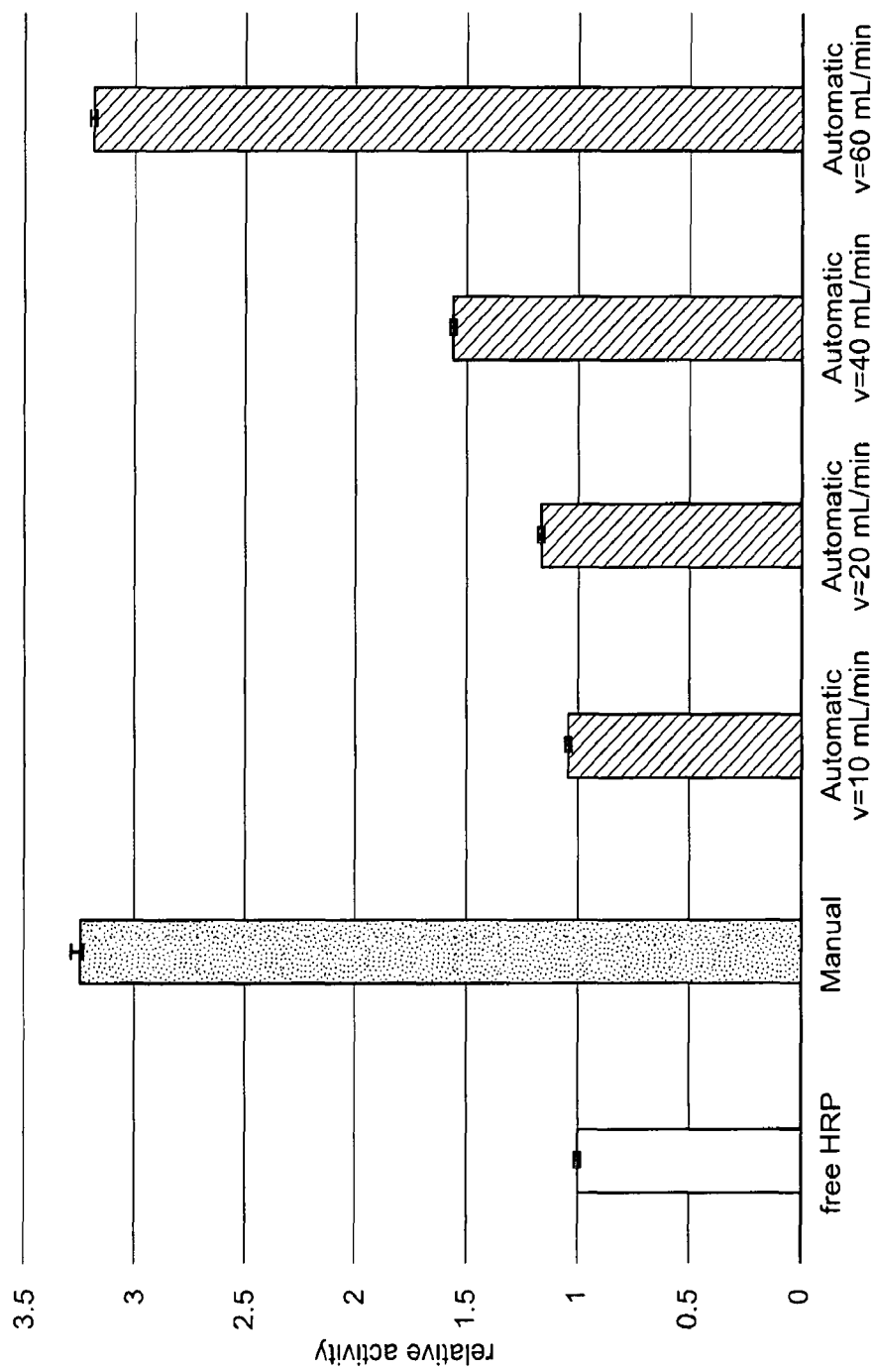
FIG. 6: Phenol oxidation activity of immobilized HRP measured spectrophotometrically by increased absorbance at 500 nm due to quinoneimine dye formation. Free HRP (white). Biomicrocatalysts (BMC) composed of magnetic microparticles (MMP) and bionanocatalysts (BNCs) made by automatically mixing HRP at pH 6 with magnetic nanoparticles (MNPs) at pH 11. BNCs had an enzyme loading of 40% (enzyme/MNP); the BMCs had an enzyme loading of 5.6% (enzyme/(MNP+MMP)). These "automatic" BMCs were assembled in continuous-flow using varied flow rates (10-60 mL/min, hatched). BMC composed of manually combined HRP at pH 6 with magnetite nanoparticle at pH11; manual BNCs had a 40% enzyme loading and templated onto MMP to form BMC at 5.6% enzyme loading (black).

Results. Controls showed that there was no uncatalyzed dye formation. HRP BNCs were templated on magnetite powder (50-100 nm) scaffolds. The resulting BMCs had ~5.6% effective loading for both the manually and automatically immobilized HRP BMCs (Table 15). The activity varied, however, with flow rate. The activities relative to free enzyme versus flow rates in automatic immobilization are as follows: 10 mL/min had 100% activity, 20 mL/min had 120% activity, 40 mL/min had 160% activity, and 60 mL/min had 320% activity, as did the manually immobilized BMCs. This improvement of activity is consistent with previous HRP immobilization in BNCs (FIG. 6).

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. An automated method of producing self-assembled bionanocatalysts (BNC), comprising combining an MNP preparation with an enzyme preparation in an automated machine, wherein said machine comprises an MNP disruptor and a BNC mixer, wherein said BNC mixer comprises a mixing tee or a mixing coil;
    wherein said automated machine performs the steps of
        (a) disrupting MNPs in said MNP preparation with said MNP disruptor; and
        (b) mixing said enzyme preparation with said disrupted MNP preparation using said BNC mixer;
    wherein said mixing step causes a plurality of enzymes from said enzyme preparation to become magnetically immobilized within said MNPs to form said BNCs; wherein said magnetically immobilized enzymes are operable to catalyze the conversion of a diffusible substrate to a diffusible product.

2. The method of claim 1, wherein said BNCs are produced in a volume of less than about 1 ml.

3. The method of claim 1, wherein said BNCs are produced in a volume of between about 1 ml and 10 ml.

4. The method of claim 1, wherein said BNCs are produced in a volume of between about 10 ml and 100 ml.

5. The method of claim 1, wherein said BNCs are produced in a volume of between about 100 ml and 1 liter.

6. The method of claim 1, wherein said BNCs are produced in a volume of between about 1 liter and 10 liters.

7. The method of claim 1, wherein said BNCs are produced in a volume of between about 10 liters and 100 liters.

8. The method of claim 1 wherein said BNCs are produced in a volume of between about 100 liters and 1000 liters.

9. The method of claim 1, wherein said BNCs are produced in a volume of between about 1 kiloliter and 10 kiloliters.

10. The method of claim 1, wherein said BNCs are produced in a volume of between about 10 kiloliters and 20 kiloliters.

11. The method of claim 1, wherein said BNCs are produced in a volume of between about 20 kiloliters and 50 kiloliters.

12. The method of claim 1, wherein said BNCs are produced in a volume of greater than about 50 kiloliters.

13. The method of claim 1, further comprising the step of templating said BNC into a stabilizing level 2 assembly.

14. The method of claim 1, wherein said machine further comprises:
    a) an enzyme container;
    b) a magnetic nanoparticle (MNP) container;
    c) an enzyme pump; and
    d) an MNP pump;
    wherein said enzyme container is operable to hold an enzyme preparation; wherein said MNP container is operable to hold an MNP preparation; wherein said MNP pump performs the step of sending said MNP preparation to said MNP disruptor; wherein said MNP pump performs the step of sending a plurality of disrupted MNPs from said MNP disruptor to said BNC mixer; wherein said enzyme pump performs the step of sending said enzyme preparation to said BNC mixer.

15. The method of claim 1, wherein said MNP disruptor is a sonicator.

16. The method of claim 15, wherein said sonicator further comprises a sonicator coil and a sonication container, wherein said sonicator coil is operable to sonicate said MNPs within said sonication container.

17. The method of claim 15, wherein the sonicator is an in-line sonicator.

18. The method of claim 15, further comprising a cooling system operable for cooling said sonicator.

19. The method of claim 18, wherein said cooling system is a water cooling system.

20. The method of claim 1, wherein said MNP disruptor is operable to mechanically disrupt said MNPs.

21. The method of claim 1, wherein said MNP disruptor is operable to magnetically disrupt said MNPs.

22. The method of claim 1, wherein said MNP disruptor is operable to thermally disrupt said MNPs.

23. The method of claim 15, wherein said enzyme pump sends said enzyme preparation to said BNC mixer via mechanical or gravitational force.

24. The method of claim 15, wherein said MNP pump sends said MNP preparation to said MNP disruptor via mechanical or gravitational force.

25. The method of claim 15, further comprising sending said BNCs to a container containing a magnetic scaffold preparation and mixing said magnetic scaffold preparation with said BNCs in said magnetic scaffold container to produce BNCs in a level 2 assembly.

26. The method of claim 25, wherein said magnetic scaffold container mixes said BNCS and said magnetic scaffold preparation mechanically.

27. The method of claim 25, wherein said magnetic scaffold container mixes said BNCS and said magnetic scaffold preparation magnetically.

28. The method of claim 25, wherein said magnetic level 2 assembly is a Magnetic Microparticle (MMP).

29. The method of claim 25, further comprising a templator that stabilizes said BNCs within said level 2 assembly.

30. The method of claim 25, wherein said level 2 assembly is magnetic.

31. The method of claim 1, further comprising the step of optimizing the chemical conditions, salts, or pH for BNC formation within said machine.

32. The method of claim 1, wherein said enzyme is an isomerase.

33. The method of claim 1, wherein said enzyme is selected from the group consisting of hydrolases, hydroxylases, nitrilases, hydratases, transaminases, ene reductases (EREDS), imine reductases (IREDS), and oxynitrilases.

34. The method of claim 1, wherein said MNPs comprise a ferrite.

35. The method of claim 34, wherein said ferrite comprises an iron oxide species.

36. The method of claim 1, wherein said MNPs comprise maghemite.

37. The method of claim 1, wherein said MNPs comprise magnetite.

* * * * *